(12) United States Patent
Huang et al.

(10) Patent No.: US 10,580,995 B2
(45) Date of Patent: Mar. 3, 2020

(54) COMPOUNDS FOR ORGANIC ELECTROLUMINESCENT COMPONENTS AND ORGANIC ELECTROLUMINESCENT DEVICES USING THE SAME

(71) Applicant: E-RAY OPTOELECTRONICS TECHNOLOGY CO., LTD., Taoyuan, Taiwan R.O.C (TW)

(72) Inventors: Heh-Lung Huang, Taoyuan (TW); Yi-Huan Fu, Taoyuan (TW); Huang-Ying Lin, Taoyuan (TW); Chi-Jen Lin, Taoyuan (TW)

(73) Assignee: E-RAY OPTOELECTRONICS TECHNOLOGY CO., LTD., Taoyuan (TW)

( * ) Notice: Subject to any disclaimer, the term of this patent is extended or adjusted under 35 U.S.C. 154(b) by 252 days.

(21) Appl. No.: 15/178,726

(22) Filed: Jun. 10, 2016

(65) Prior Publication Data

US 2017/0279054 A1     Sep. 28, 2017

(30) Foreign Application Priority Data

Mar. 25, 2016   (TW) .............................. 105109396 A

(51) Int. Cl.
*H01L 51/00*     (2006.01)
*C07D 401/04*    (2006.01)
(Continued)

(52) U.S. Cl.
CPC ........ *H01L 51/0067* (2013.01); *C07D 401/04* (2013.01); *C07D 401/14* (2013.01); *C07D 403/10* (2013.01); *C07D 405/14* (2013.01); *C07D 409/14* (2013.01); *C09K 11/06* (2013.01); *H01L 51/0052* (2013.01); *H01L 51/0058* (2013.01); *H01L 51/0059* (2013.01); *H01L 51/0072* (2013.01); *H01L 51/0073* (2013.01); *H01L 51/0074* (2013.01);
(Continued)

(58) Field of Classification Search
CPC .. C07D 401/04; C07D 401/14; C07D 403/10; C07D 405/14; C07D 409/14; C07D 405/10; C07D 409/10; C09K 11/06; C09K 2211/1007; C09K 2211/1011; C09K 2211/1014; C09K 2211/1029; C09K 2211/1044; C09K 2211/1088; C09K 2211/1092; C09K 11/025; H01L 2251/558; H01L 51/0052; H01L 51/0058; H01L 51/0059; H01L 51/0067; H01L 51/0072; H01L 51/0073; H01L 51/0074; H01L 51/5012; H01L 51/5016; H01L 51/5072; H01L 51/5076; H01L 51/0071; H01L 51/5004; H01L 2251/552; H01L 51/0054; H01L 51/0055; H01L 51/5092; H01L 51/5096; H01L 2251/305
See application file for complete search history.

(56) References Cited

U.S. PATENT DOCUMENTS

2009/0284134 A1* 11/2009 Iida ...................... C07D 209/86
                                                                313/504
2014/0073784 A1*  3/2014 Mizutani .............. C07D 405/14
                                                                544/216

* cited by examiner

*Primary Examiner* — Ling Siu Choi
*Assistant Examiner* — Gennadiy Mesh
(74) *Attorney, Agent, or Firm* — Amin, Turocy & Watson, LLP

(57) ABSTRACT

Compounds of formula (I) and organic electroluminescent devices containing a cathode, an anode, and an organic layer, wherein the organic layer containing the compounds of formula (I) are disclosed. The compounds of formula (I) are:

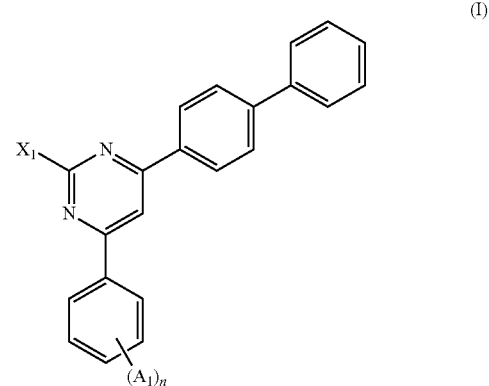

wherein $A_1$ represents a substituted or unsubstituted (C6-C30) aryl, or a substituted or unsubstituted 5- to 30-membered heteroaryl; n is an integer of 1 or 2, and $X_1$ is selected from the group of

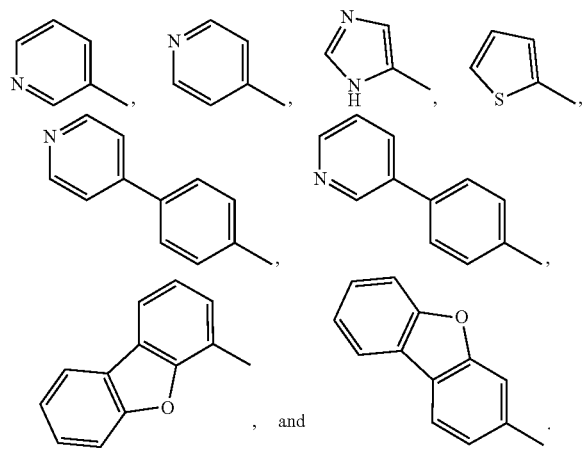

16 Claims, 4 Drawing Sheets

(51) Int. Cl.
*C07D 401/14* (2006.01)
*C07D 403/10* (2006.01)
*C07D 405/14* (2006.01)
*C07D 409/14* (2006.01)
*C09K 11/06* (2006.01)
*H01L 51/50* (2006.01)

(52) U.S. Cl.
CPC ............... *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1088* (2013.01); *C09K 2211/1092* (2013.01); *H01L 51/5012* (2013.01); *H01L 51/5016* (2013.01); *H01L 51/5072* (2013.01); *H01L 51/5076* (2013.01); *H01L 2251/558* (2013.01)

COMPOUNDS FOR ORGANIC ELECTROLUMINESCENT COMPONENTS AND ORGANIC ELECTROLUMINESCENT DEVICES USING THE SAME

BACKGROUND

1. Technical Field

The present disclosure relates to compounds for organic electroluminescent devices and organic electroluminescent devices using the same.

2. Description of Related Art

There has been an increasing interest in developing novel organic materials that cater to organic light emitting device (OLED) applications. Such devices are commercially attractive because they offer the cost-advantage in manufacturing high density pixel displays exhibiting brilliant luminance with long life times, high efficiency, low driving voltages and wide color range.

A typical OLED comprises at least one organic emissive layer sandwiched between an anode and a cathode. When a current is applied, the anode injects holes and the cathode injects electrons into the one or more organic emissive layer(s). The injected holes and electrons migrate individually toward the oppositely charged electrode. When an electron and a hole co-localize on the same molecule, an "exciton" is formed, which is a co-localized electron-hole pair having an excited energy state. Light is emitted when the exciton relaxes through a photo emissive mechanism. In order to improve the charge transport capabilities and the luminous efficiency of such devices, one or more additional layers around the emissive layer, such as an electron transport layer(s) and/or a hole transport layer(s), or an electron blocking layer(s) and/or a hole block layer(s) have been incorporated. Doping the host material with another material (i.e., guest) to enhance the performance of the device and to tune the chromaticity has been disclosed in U.S. Pat. Nos. 5,707,745 and 9,153,787, which are incorporated herein by reference in their entirety.

One of the reasons to manufacture an OLED with a multi-layered thin film structure is the stabilization of the interfaces between the electrodes and the organic layers. In addition, in organic materials, the mobility of the electrons is significantly different from that of holes. Thus, if appropriate hole transport layers and electron transport layers are used, holes and electrons can be efficiently transferred to the luminescent layer. Besides, if the densities of the holes and the electrons are balanced in the emitting layer, its luminous efficiency can be increased. Combining the organic layers described above properly can enhance the efficiency and lifetime of the device. However, it remains difficult to find an organic material that would satisfy all the practical requirements of a display.

Accordingly, there is an urgent need to develop a material for electron transportation in order to extend the lifetime of the devices and to improve the luminous efficiency and to keep low driving voltage.

SUMMARY

The present disclosure is to provide a material for OLED with high luminous efficiency, low driving voltage and longer lifetime.

The present disclosure provides a compound of formula (I) for OLED:

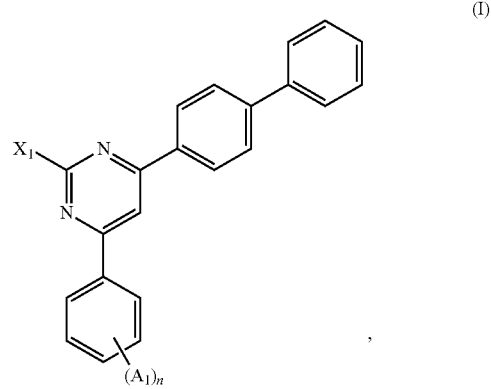

wherein $X_1$ represents

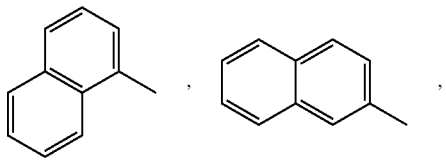

or a substituted or unsubstituted 5- to 30-membered heteroaryl;

$A^1$ represents a substituted or unsubstituted (C6-C30) aryl, or a substituted or unsubstituted 5- to 30-membered heteroaryl; and n is an integer of 1 or 2, and when $X_1$ is

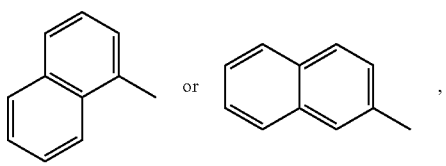

n is 1.

The present disclosure further provides an organic electroluminescent device, comprising a cathode; an anode; and an organic layer disposed between the cathode and the anode, wherein the organic layer comprises the compound of the above formula (I).

The organic layer of the organic electroluminescent device of the present disclosure may be an electron transport layer, an electron injection layer, an emitting layer, a hole block layer, or an electron block layer. Additionally, besides the organic layer, the organic electroluminescent device may further comprise at least one layer(s) selected from the group consisting of an electron transport layer, an electron injection layer, an emitting layer, a hole block layer, and an electron block layer other than the organic layer.

According to the present disclosure, using the compounds of formula (I) provided by the present disclosure can improve the stability of the device and lower the operational voltage.

DETAILED DESCRIPTION

Figure 1:
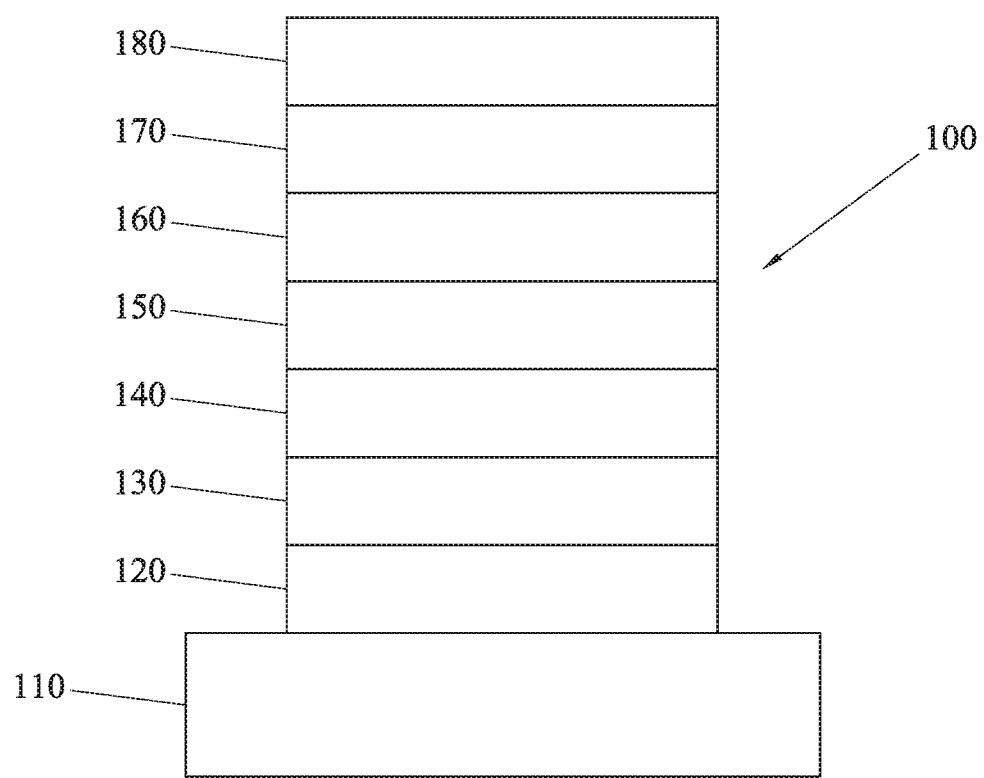
FIG. 1 is a cross-sectional view illustrating an organic electroluminescent device according to an embodiment of the present disclosure.

The following specific embodiments are provided to illustrate the disclosure of the present disclosure. These and other advantages and effects can be easily understood by those skilled in the art after reading the disclosure of this specification.

All the ranges and values disclosed herein can be included and incorporated. For example, when any value, such as an integer or a point, falls within the range described herein, the sub range can be deducted base on the point or the value as an upper limit or a lower limit. In addition, the groups listed herein, such as groups or substituents for $X_1$ and $A_1$, can be incorporated into formula (I) with other groups.

According to the present disclosure, the compound for OLED application is represented by formula (I):

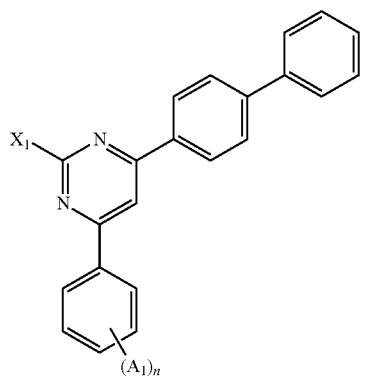

(I)

wherein $X_1$ represents

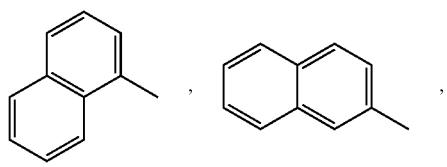

or a substituted or unsubstituted 5- to 30-membered heteroaryl;

$A^1$ represents a substituted or unsubstituted (C6-C30) aryl, or a substituted or unsubstituted 5- to 30-membered heteroaryl; and n is an integer of 1 or 2, and when $X_1$ is

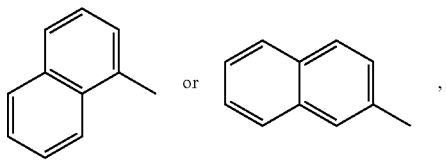

n is 1.

In an embodiment, $X_1$ and $A_1$ are the same.

In an embodiment, $X_1$ and $A_1$ are different from each other.

In an embodiment, when n is 2, each of $A_1$ is the same.

In an embodiment, when n is 2, each of $A_1$ is different from each other.

In an embodiment, $X_1$ and $A_1$ each independently represent a substituted or unsubstituted (C6-C20) aryl, a substituted or unsubstituted 5- to 20-membered heteroaryl, wherein the 5- to 20-membered heteroaryl comprises at least one hetero atom selected from the group consisting of N, O and S.

In an embodiment, $A_1$ in the above formula (I) represents compounds of formula (II) or (III):

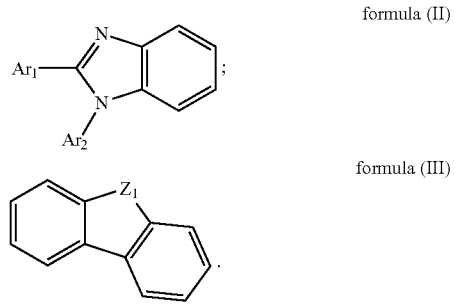

In formula (II), each of $Ar_1$ and $Ar_2$ independently represents unsubstituted (C6-C20) aryl(ene). The compound of formula (II) binds to the compound of formula (I) or forms a fused ring with the compound of formula (I) by $Ar_1$ or $Ar_2$; in formula (III), $Z_1$ represents N,

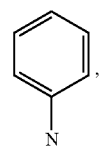

N, O, S, $CMe_2$ or $CH_2$, wherein when $Z_1$ is N, the compound of formula (III) binds to the compound of formula (I) by $Z_1$, and when $Z_1$ is

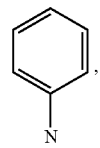

N, O, S, $CMe_2$ or $CH_2$, the compound of formula (III) binds to the compound of formula (I) by the phenyl group thereof.

In an embodiment, when n is 1, the compound of formula (I) is represented by formula (I-1) or (I-2):

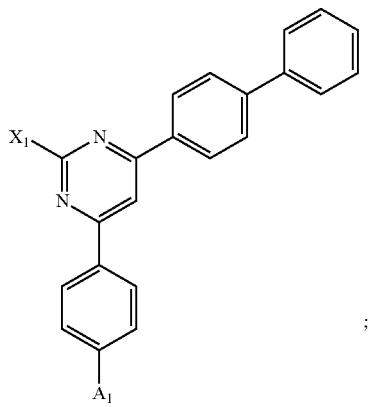
(I-1)

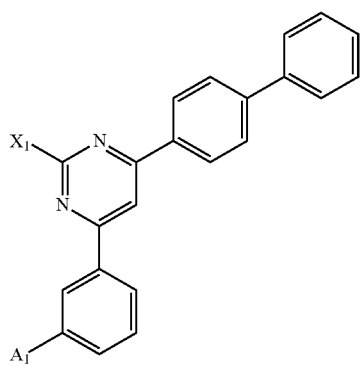
(I-2)

In an embodiment, when n is 2, the compound of formula (I) is represented by formula (I-3):

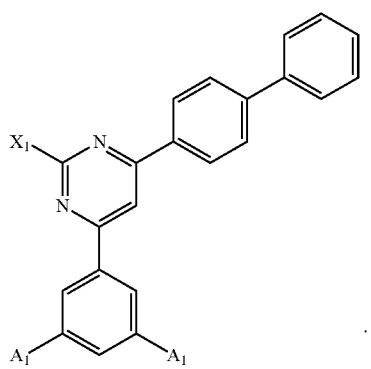
(I-3)

Herein, the term "substituted" in the phrase "substituted or unsubstituted" means that the H atom in certain functional group is replaced by another atom or group (i.e. substituents). Each of the substituents can be independently at least one selected from the group consisting of deuterium; halogen; (C1-C30) alkyl; (C1-C30) alkoxy; (C6-C30) aryl; 5- to 30-membered heteroaryl which can be substituted by (C6-C30) aryl; 5- to 30-membered heteroaryl substituted by (C6-C30) aryl; (C3-C30) cycloalkyl; 5- to 7-membered heterocycloalkyl; tri(C1-C30)alkylsilyl; tri(C1-C30)arylsilyl; di(C1-C30)alkyl(C6-C30)arylsilyl; (C1-C30)alkyldi (C6-C30)arylsilyl; (C2-C30)alkenyl; (C2-C30)alkynyl; cyano; di(C1-C30)alkylamine; di(C6-C30)arylamine; (C1-C30)alkyl(C6-C30)arylamine; di(C6-C30)arylboryl; di(C1-C30)alkylboryl; (C1-C30)alkyl(C6-C30)arylboryl; (C6-C30)aryl(C1-C30)alkyl; (C1-C30)alkyl(C6-C30)aryl; carboxyl; nitro; and hydroxyl.

In an embodiment, the (C6-C30)aryl and the 5- to 30-membered heteroaryl are each independently substituted by at least one substituent selected from the group consisting of (C1-C10) alkyl, (C6-C30)aryl and 5- to 30-membered heteroaryl substituted by (C6-C30)aryl.

In another embodiment, the (C6-C30)aryl and the 5- to 30-membered heteroaryl are each independently substituted by at least one substituent selected from the group consisting of (C1-C5)alkyl, (C6-C10)aryl and benzoimidazolyl substituted by (C6-C10)aryl.

Herein, "aryl(ene)" refers to aryl or aryl(ene). Aryl refers to monocyclic ring or fused ring derived from aromatic hydrocarbon, and comprises such as phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenyl phenanthrenyl, anthryl, indenyl, triphenylenyl, pyrenyl, naphthacenyl, pyrylo, chrysenyl, naphthonaphthyl, or fluoranthenyl.

Herein, "heteroaryl(ene)" represents heteroaryl or heteroaryl(ene). 5- to 30-membered heteroaryl is referring to an aryl whose main chain has 3 to 30 atoms comprising at least one hetero atom selected from the group consisting of B, N, O, S, P(=O), Si, and P; is a monocyclic ring, or a fused ring condensed with at least one benzene; is partially saturated; is formed by linked at least one hetero aryl or aryl to a heteroaryl through one or more single bond; and comprises monocyclic cyclic heteroaryl such as furyl, thienyl, pyrrolyl, imidazolyl, pyrazolyl, thiazolyl, thiadiazolyl, isothiazolyl, isooxazolyl, oxazolyl, oxadiazolyl, triazinyl, tetrazinyl, triazolyl, tetrazolyl, furazanyl, pyridyl, pyrazinyl, pyrimidinyl, pyridazinyl; and is a fused cyclic heteroaryl such as benzofuryl, benzothienyl, isobenzofuryl, dibenzofuryl, dibenzo thienyl, benzoimidazolyl, benzothiazolyl, benzoisothiazolyl, benzoisooxazolyl, benzooxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, dihydroacridinyl.

In an embodiment, $X_1$ is one selected from the group consisting of

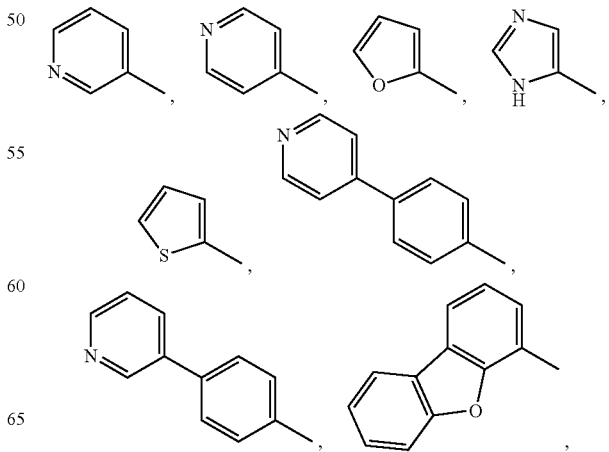

-continued

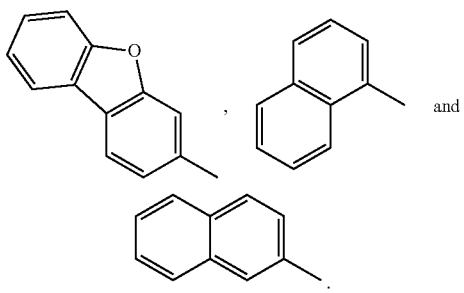

In an embodiment, $A_1$ is one selected from the group consisting of

The present disclosure further provides an organic electroluminescent device, comprising a cathode; an anode; and an organic layer disposed between an anode and a cathode, wherein the organic layer comprises the compound of the above formula (I).

The example of the compound of the above formula (I) may be selected from but not limited to the compounds below 1-1 to 1-10, 2-1 to 2-10, 3-1 to 3-10, 4-1 to 4-10, 5-1 to 5-10, 6-1 to 6-10, 7-1 to 7-10, 8-1 to 8-10, 9-1 to 9-10, 10-1 to 10-10, 11-1 to 11-10, 12-1 to 12-10, 13-1 to 13-10, 14-1 to 14-10, 15-1 to 15-10, 16-1 to 16-10, 17-1 to 17-10, 18-1 to 18-10, 19-1 to 19-10, 20-1 to 20-10, 21-1 to 21-10, 22-1 to 22-10, 23-1 to 23-10, 24-1 to 24-10, 25-1 to 25-10, 26-1 to 26-10, 27-1 to 27-10, 28-1 to 28-10, 29-1 to 29-10, 30-1 to 30-10, 31-1 to 31-10, 32-1 to 32-10, 33-1 to 33-10, 34-1 to 34-11, 35-1 to 35-11, 36-1 to 36-11.

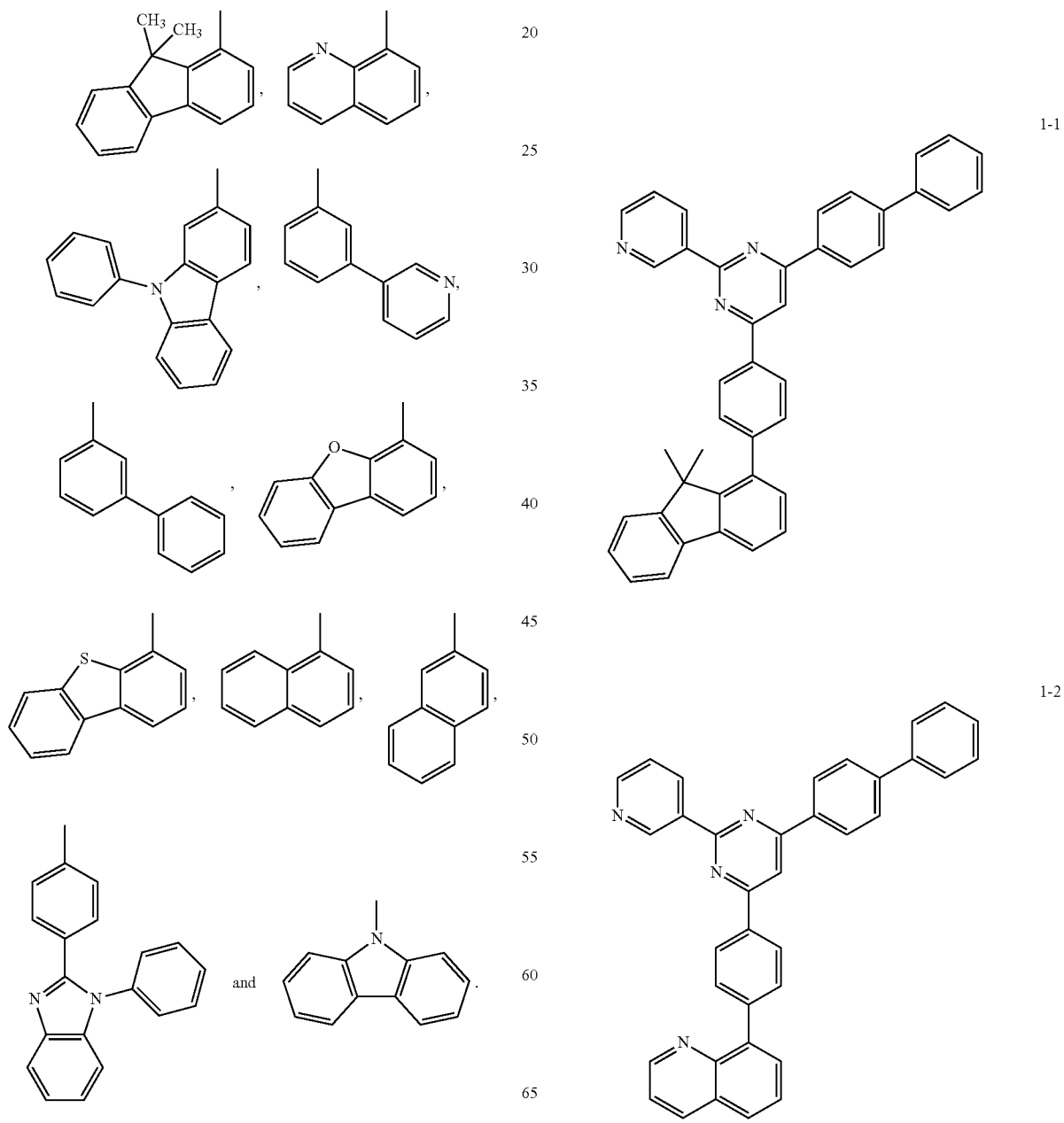

1-3
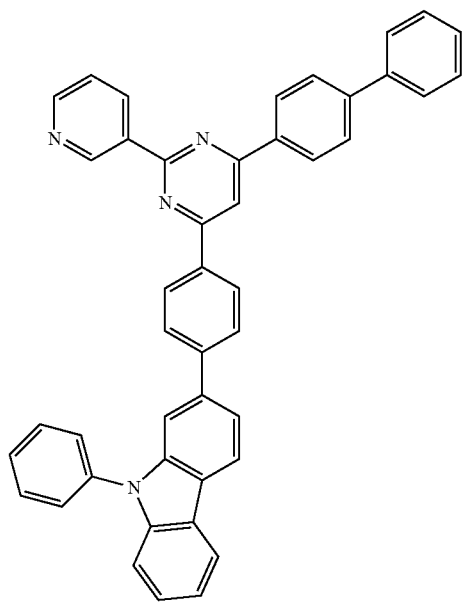
1-4
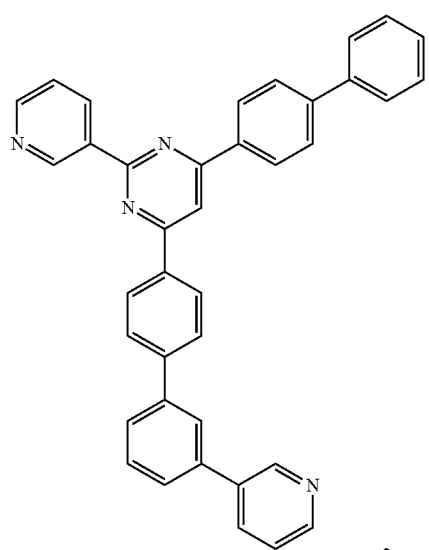
1-5
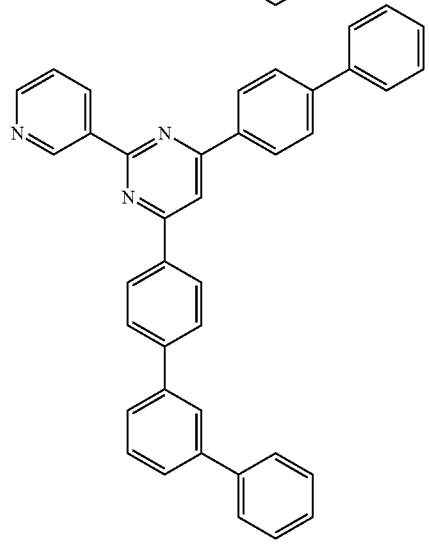
1-6
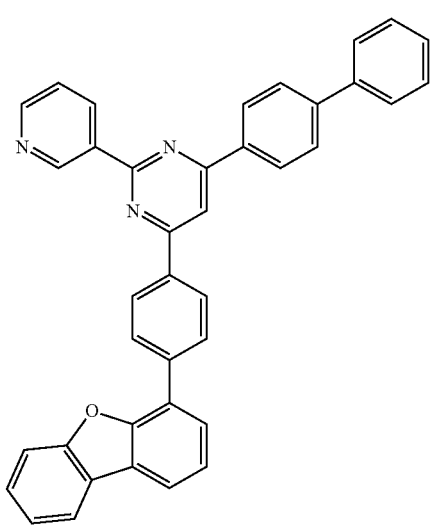
1-7
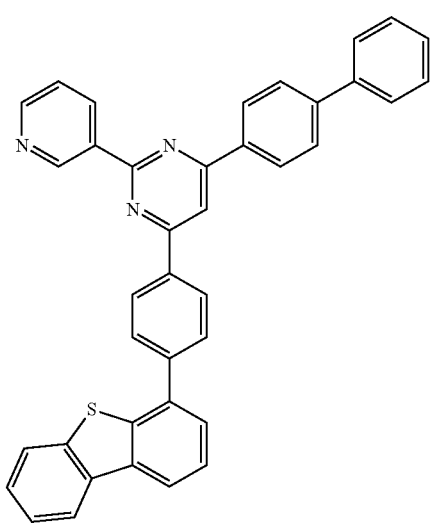
1-8
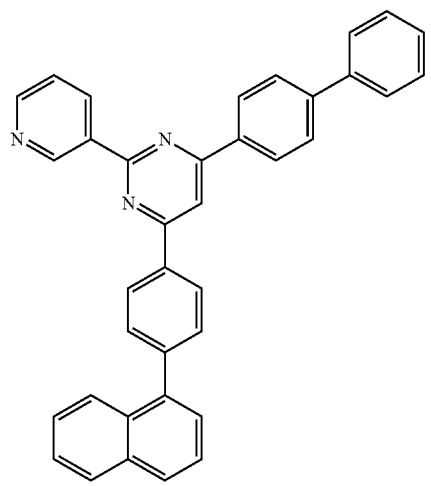

1-9
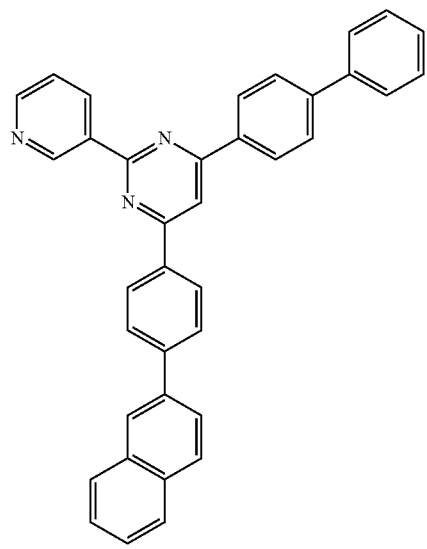
1-10
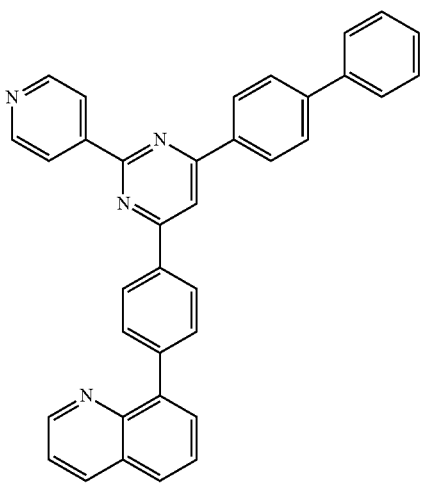
2-1
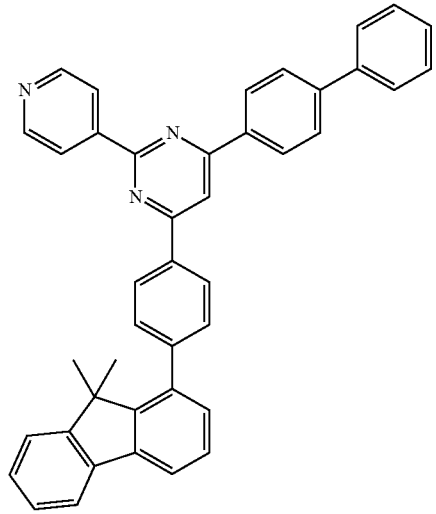
2-2
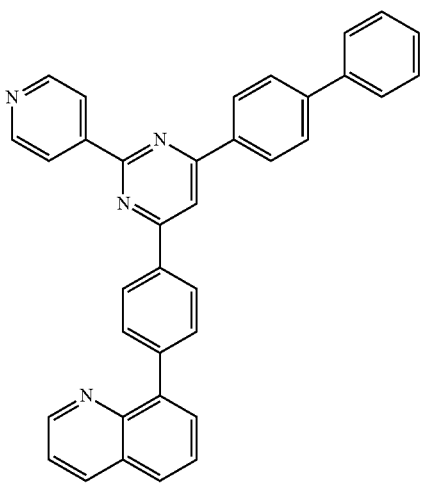
2-3
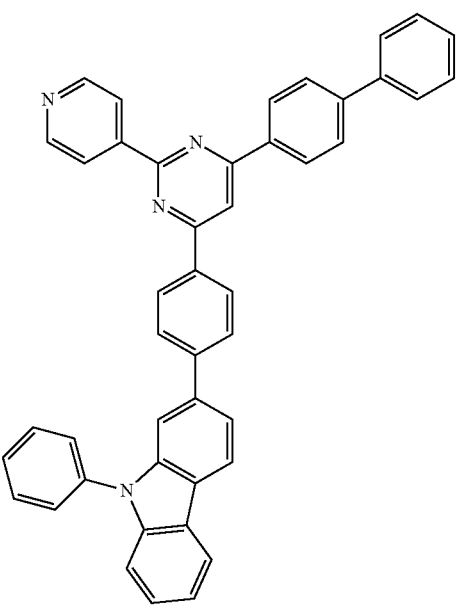
2-4
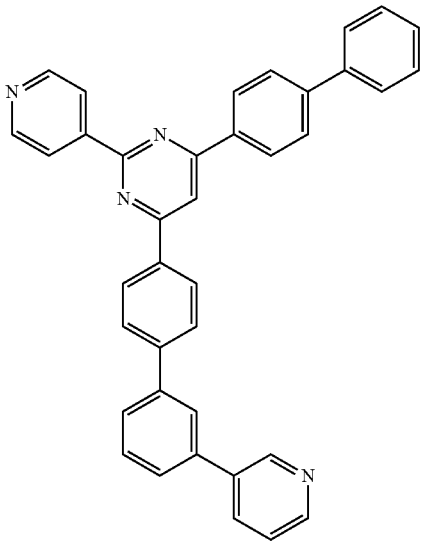

2-5
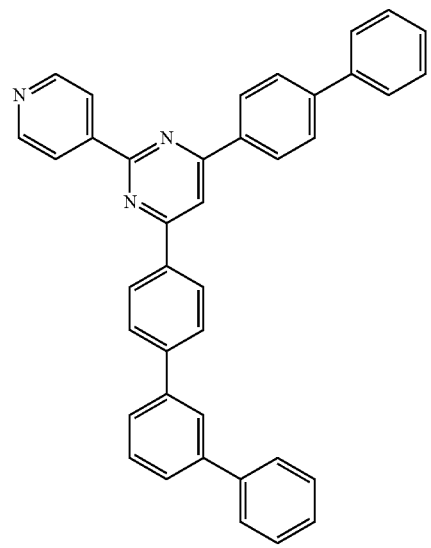
2-6
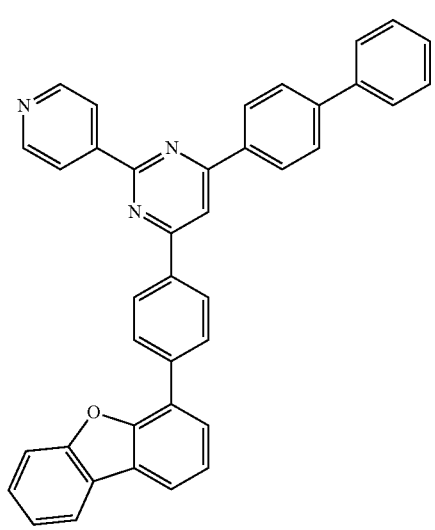
2-7
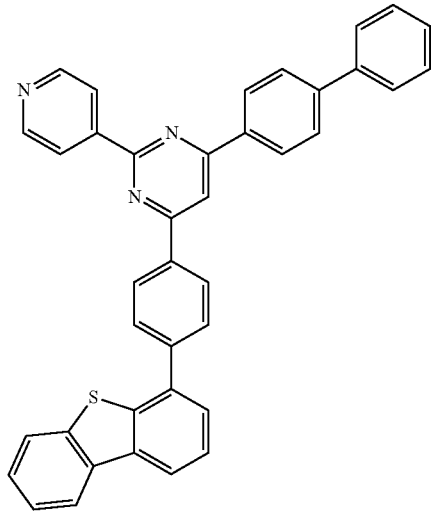
2-8
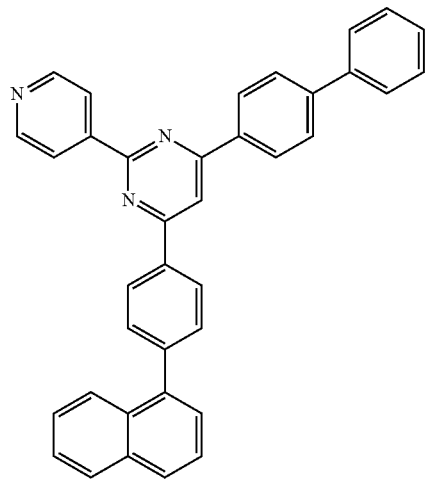
2-9
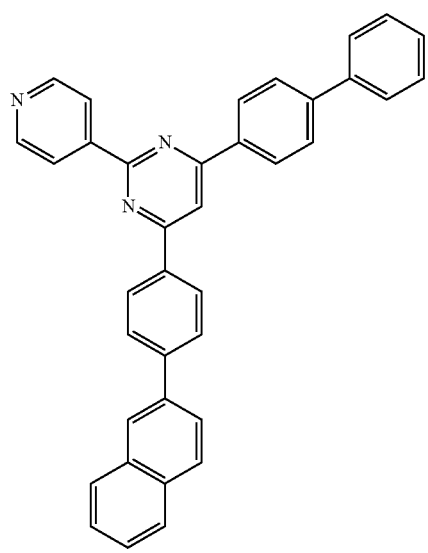
2-10
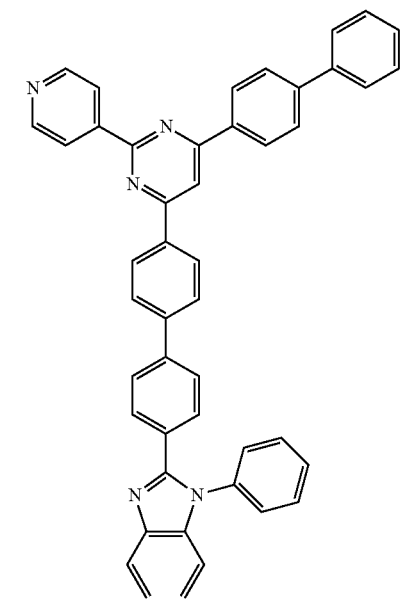

3-1
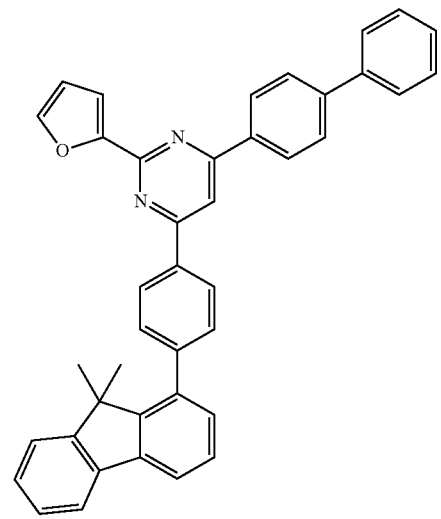
3-2
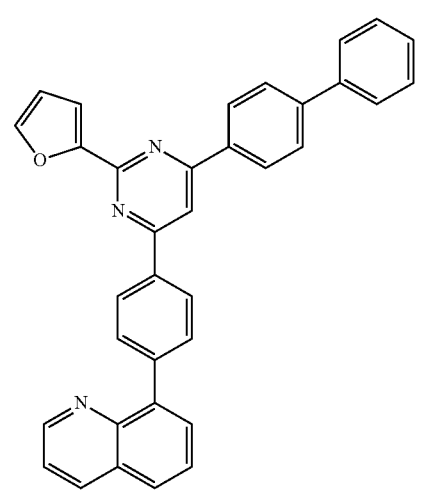
3-3
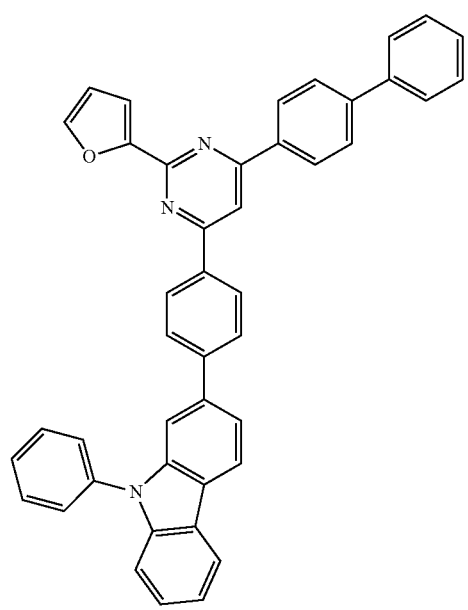
3-4
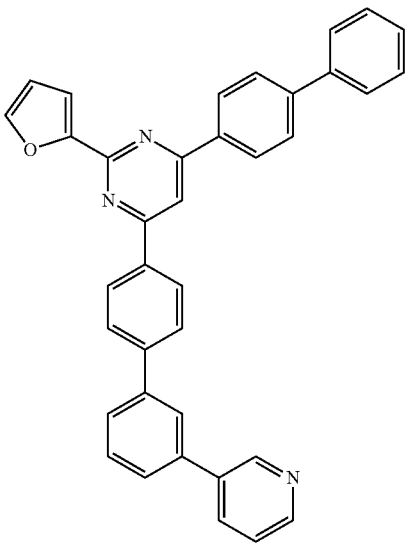
3-5
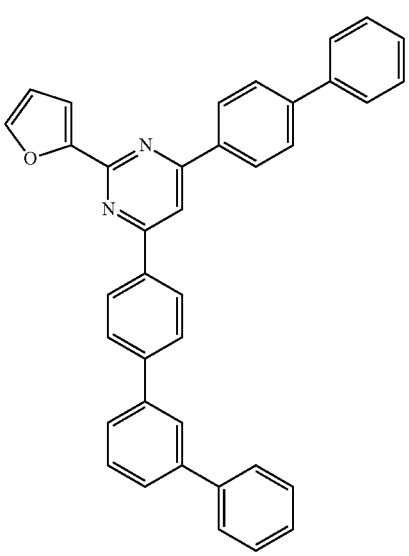
3-6
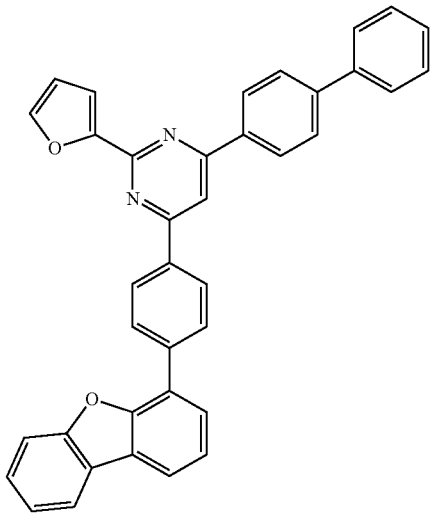

3-7
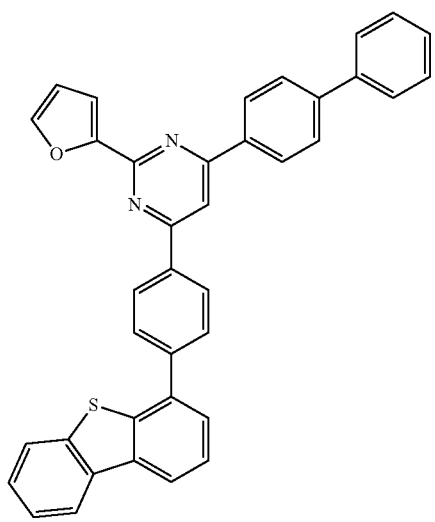
3-10
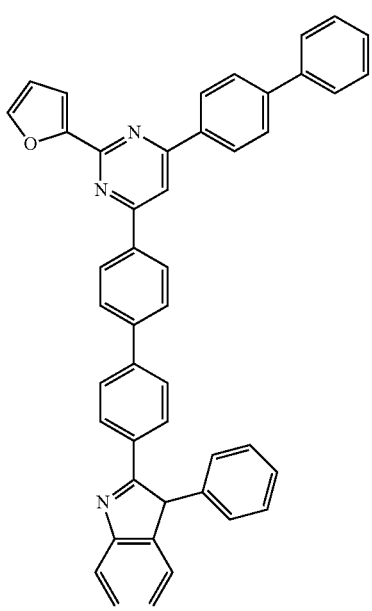
3-8
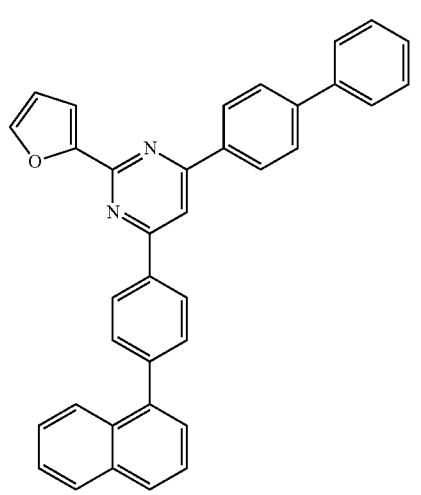
4-1
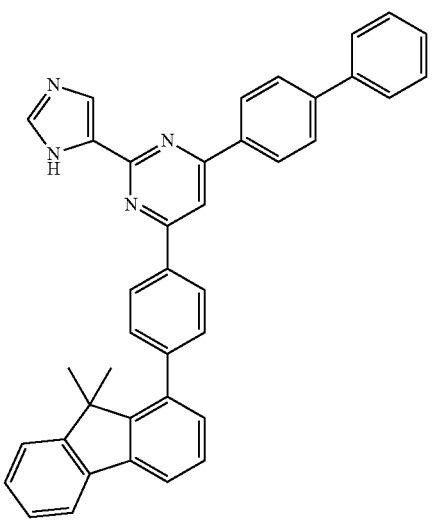
3-9
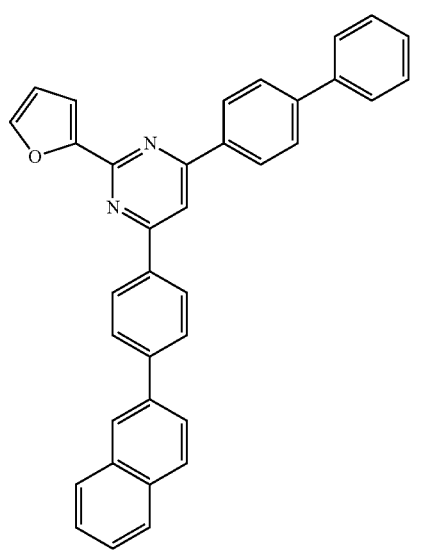
4-2
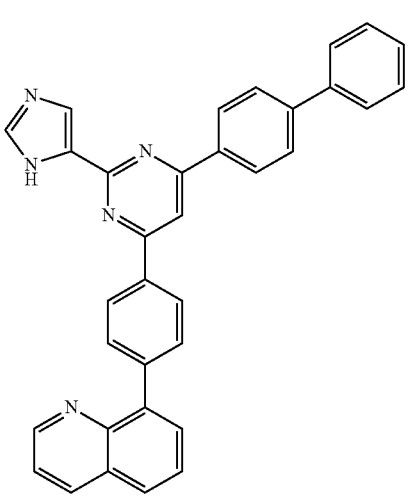

4-3
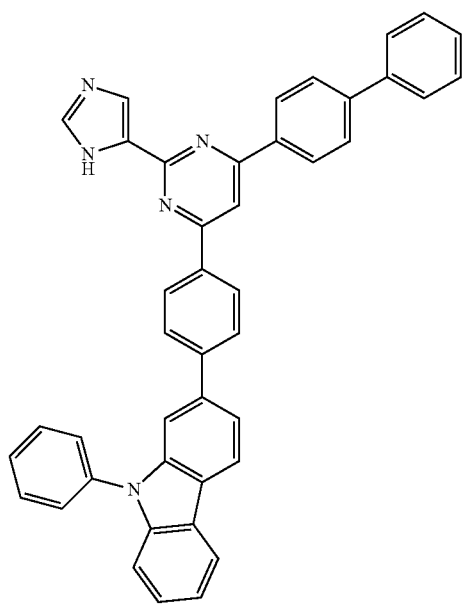
4-4
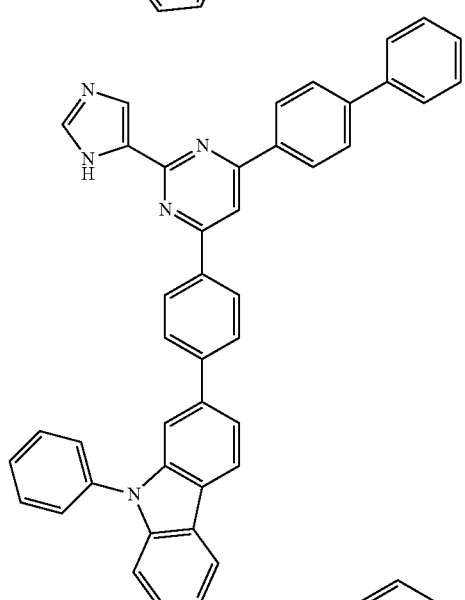
4-5
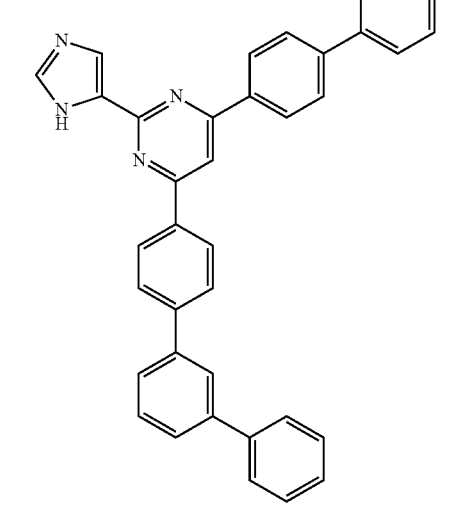
4-6
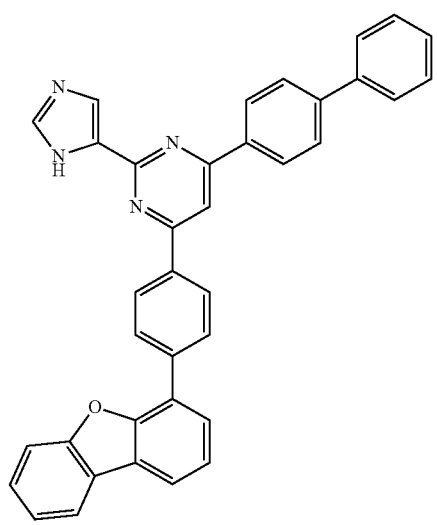
4-7
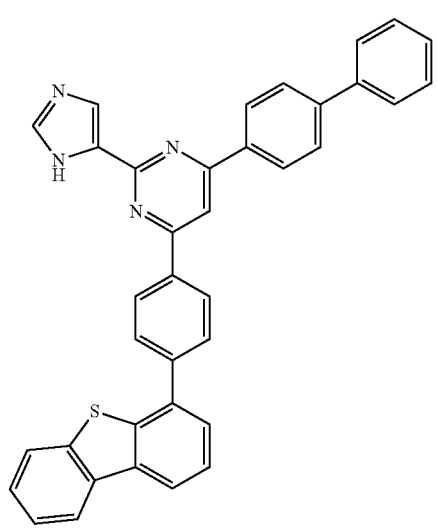
4-8
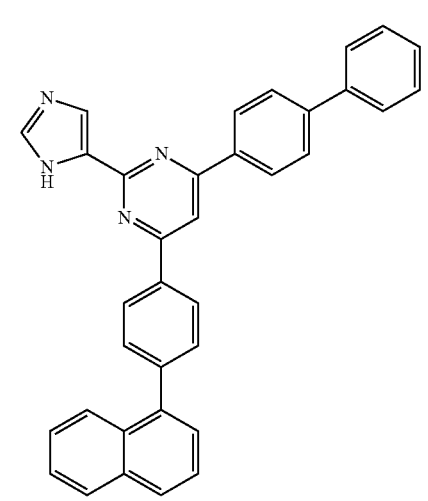

-continued
4-9
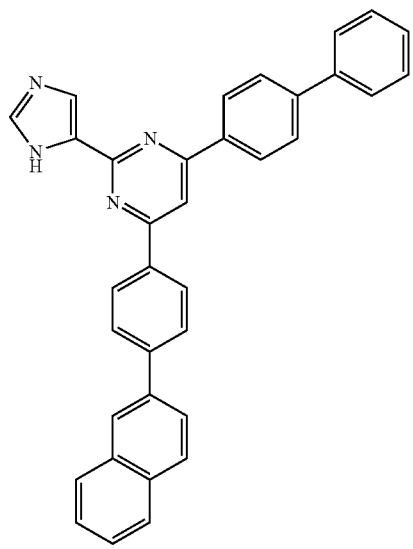
4-10
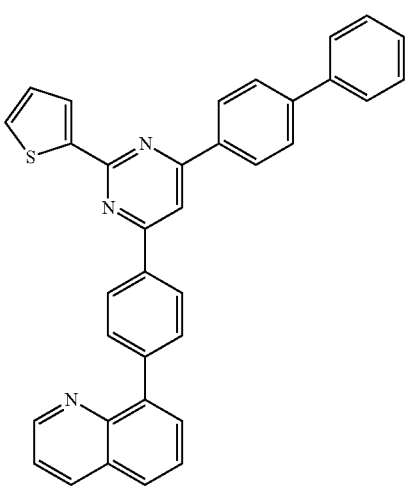
5-1
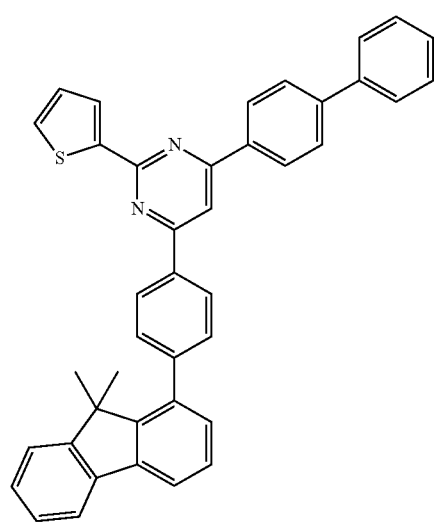
-continued
5-2
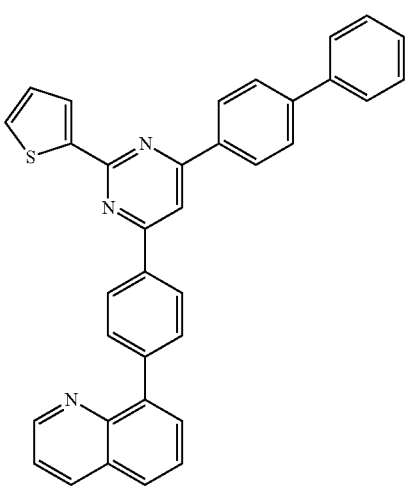
5-3
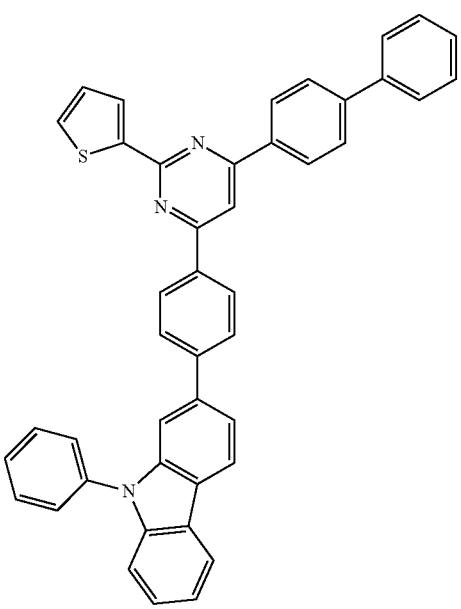
5-4
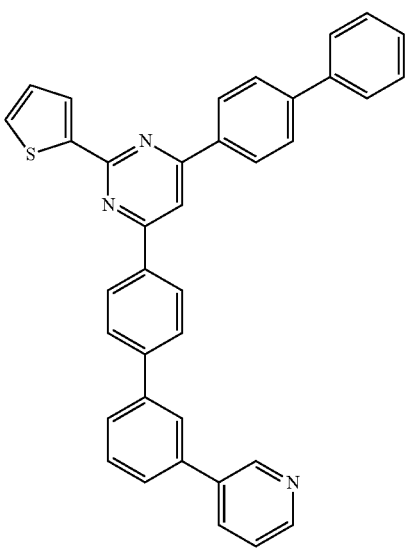

5-5
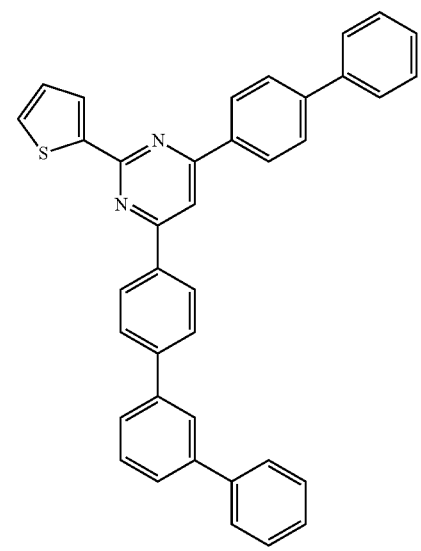
5-6
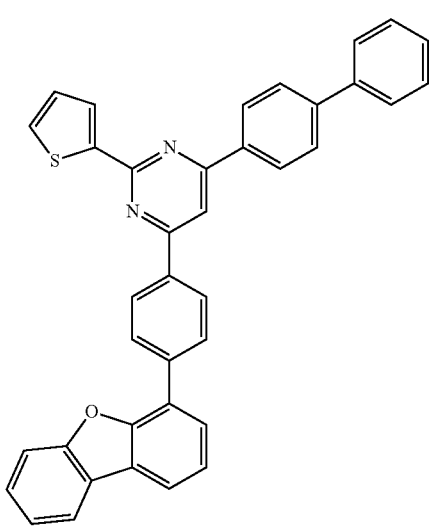
5-7
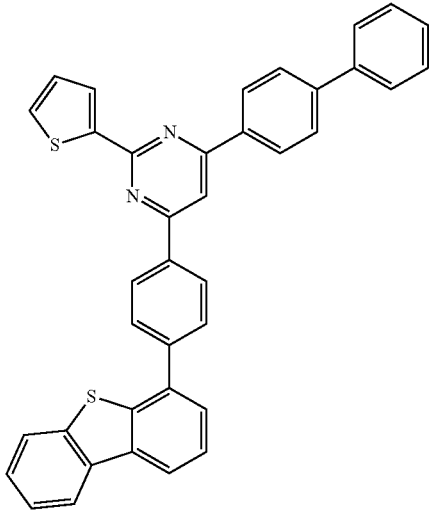
5-8
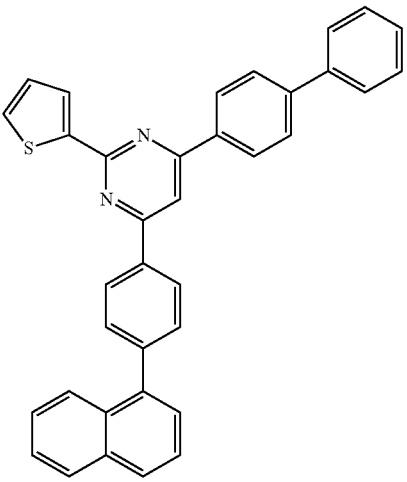
5-9
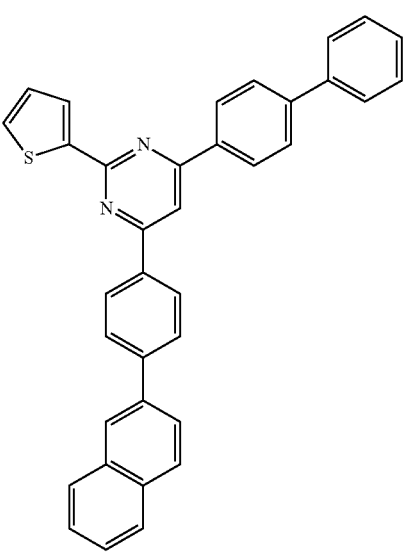
5-10
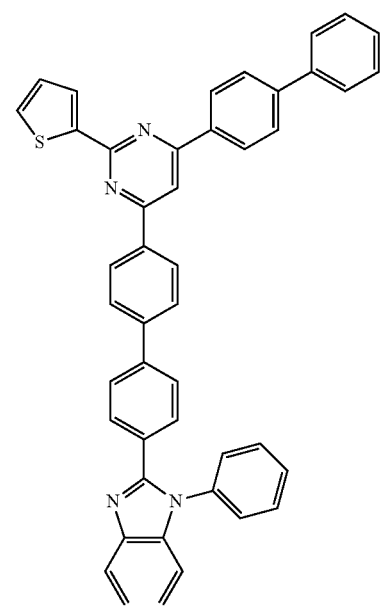

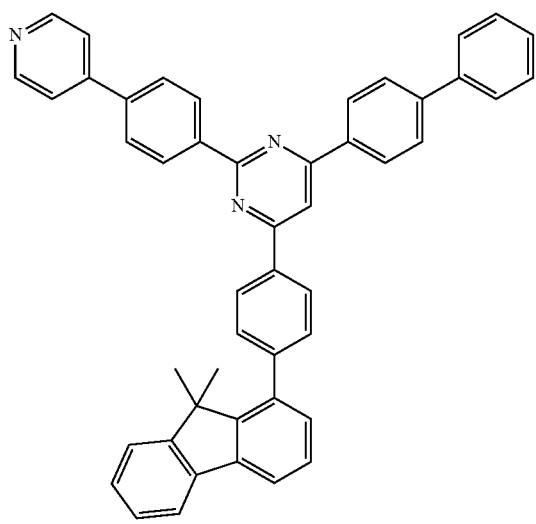
6-1
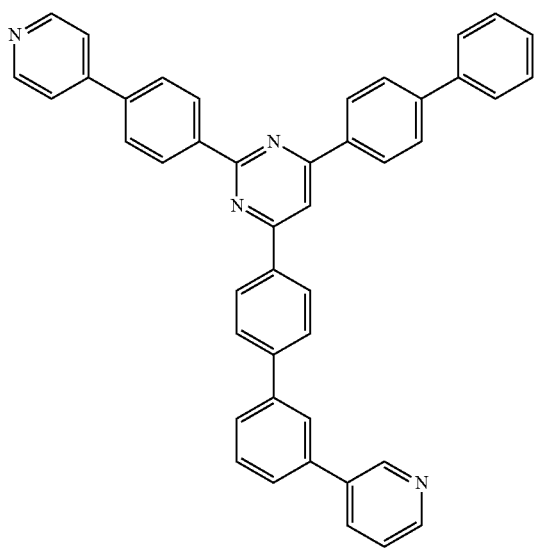
6-4
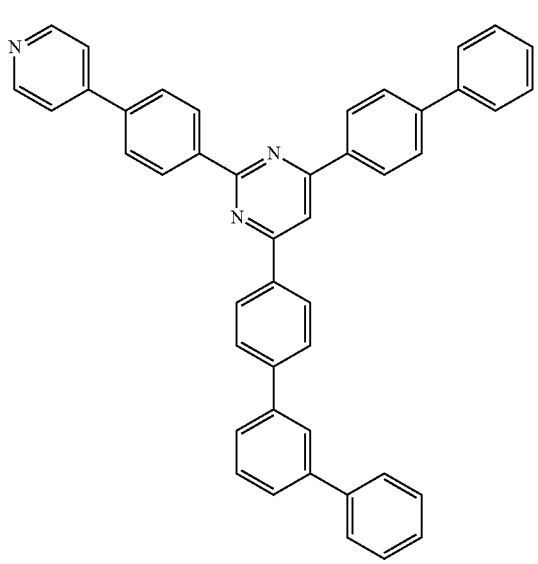
6-5
6-2
6-3
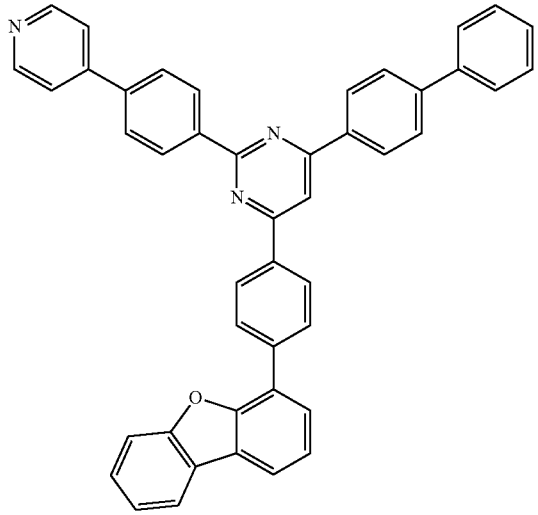
6-6

6-7
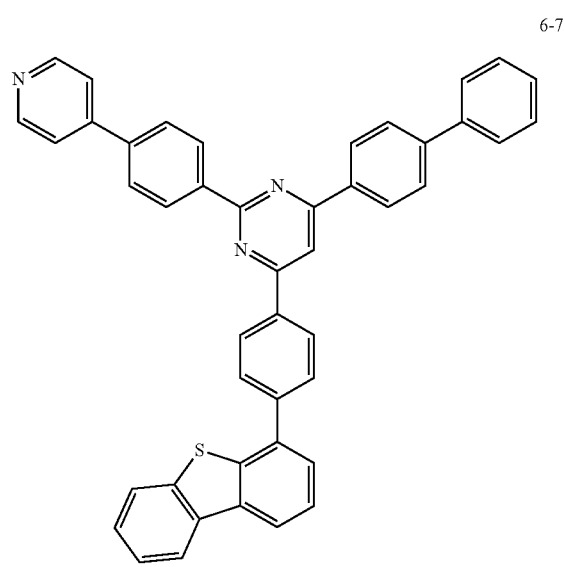
6-8
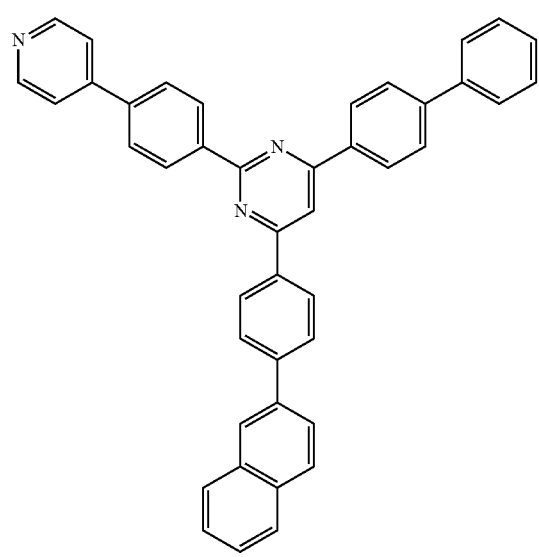
6-9
6-10
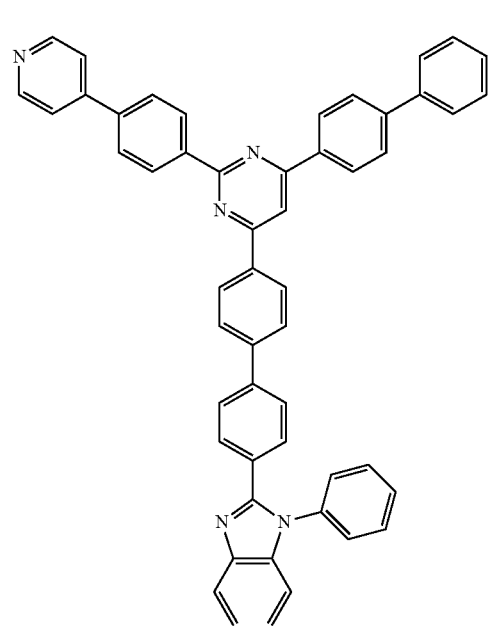
7-1
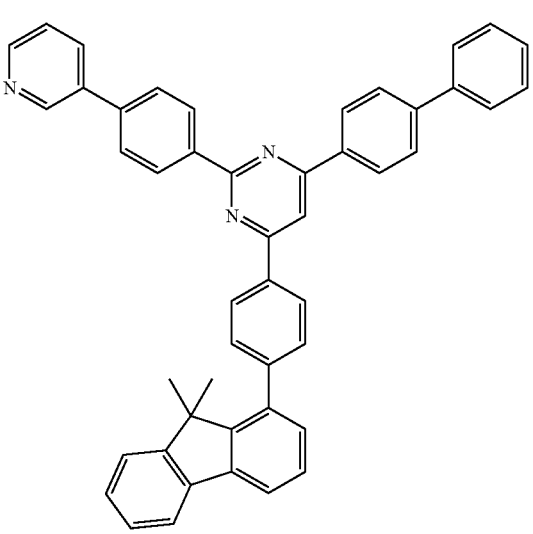
7-2
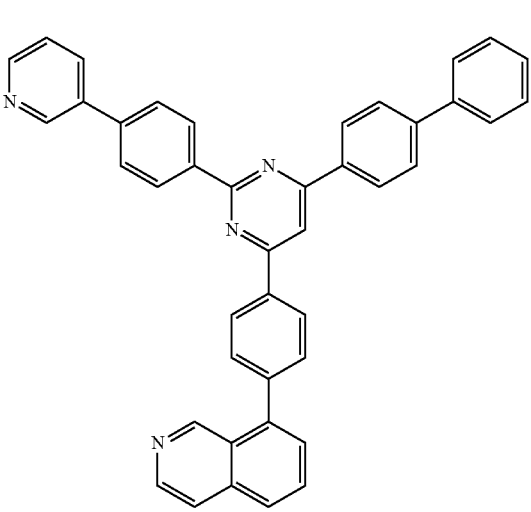

7-3
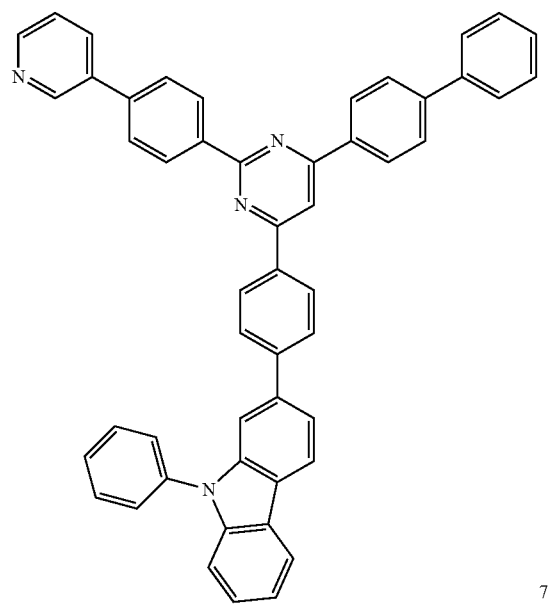
7-4
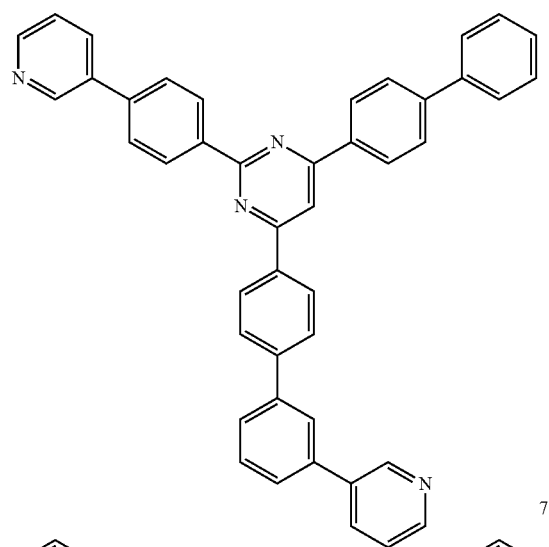
7-5
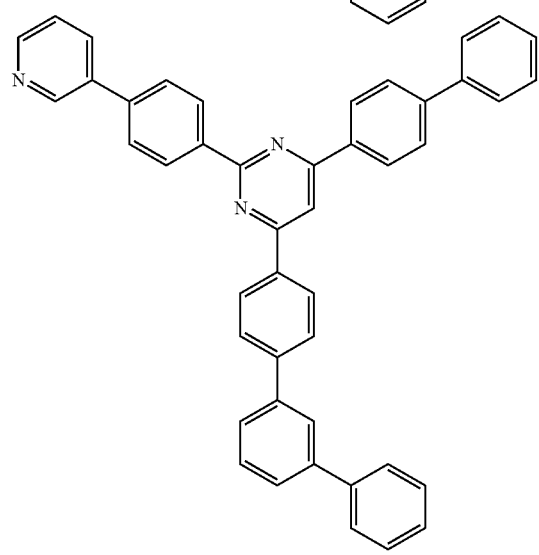
7-6
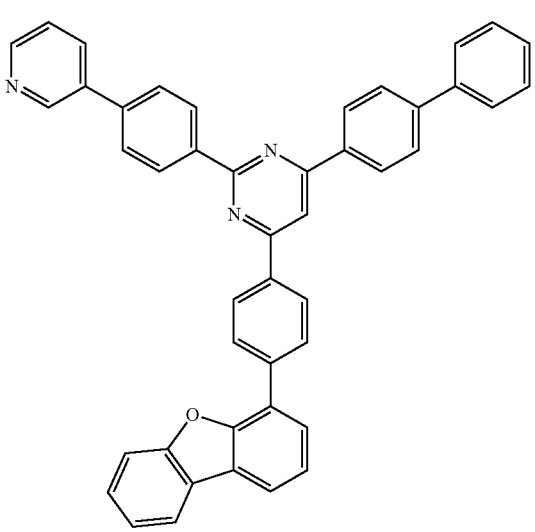
7-7
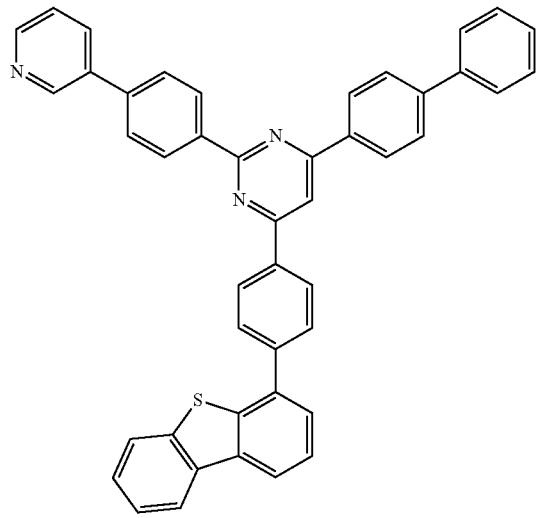
7-8
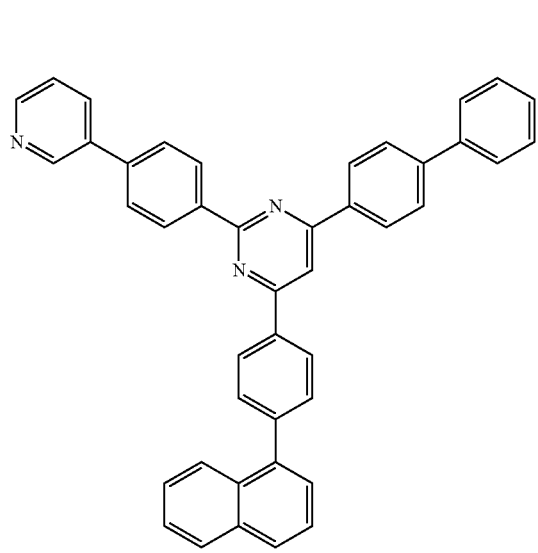

-continued
7-9
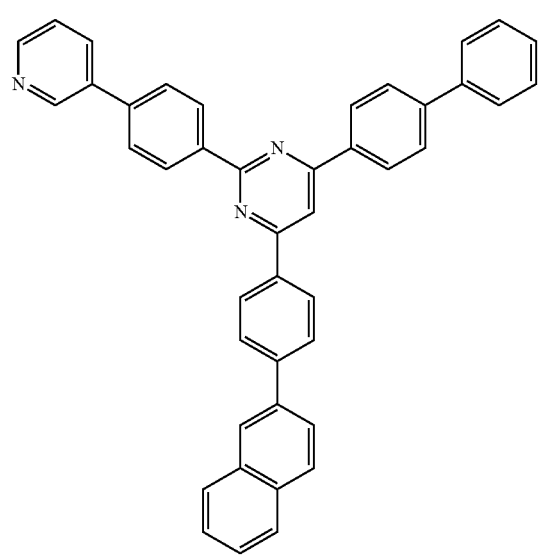
7-10
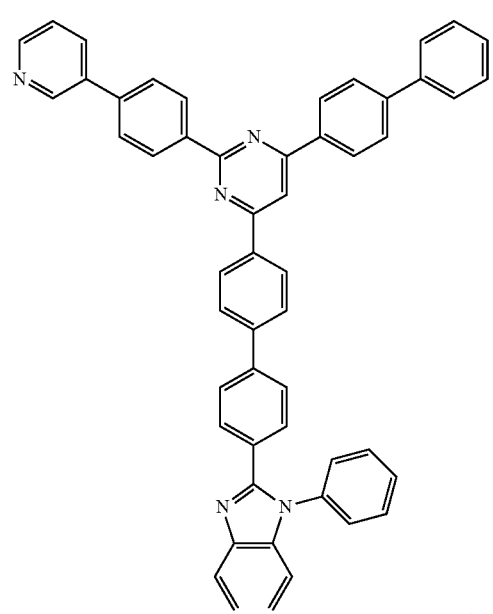
8-1
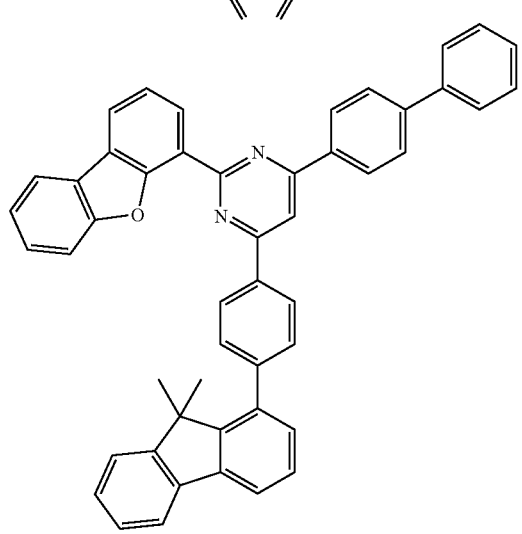
-continued
8-2
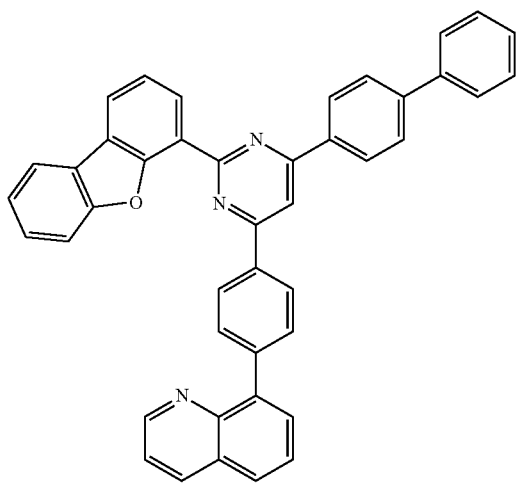
8-3
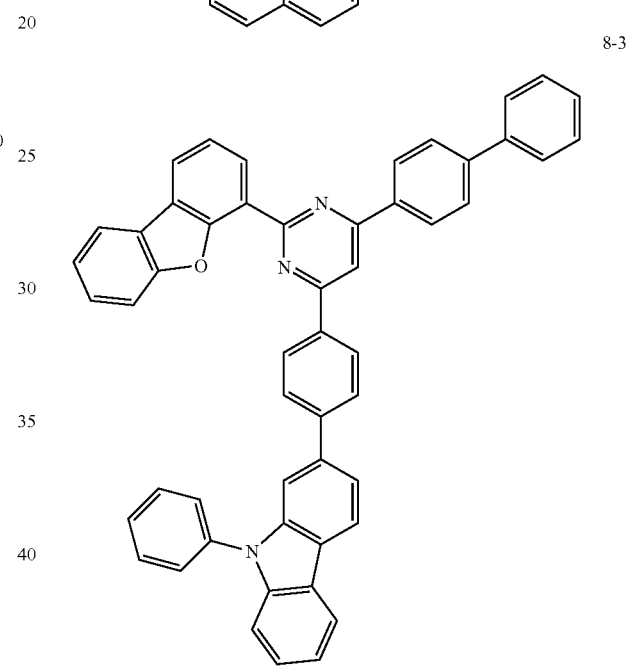
8-4
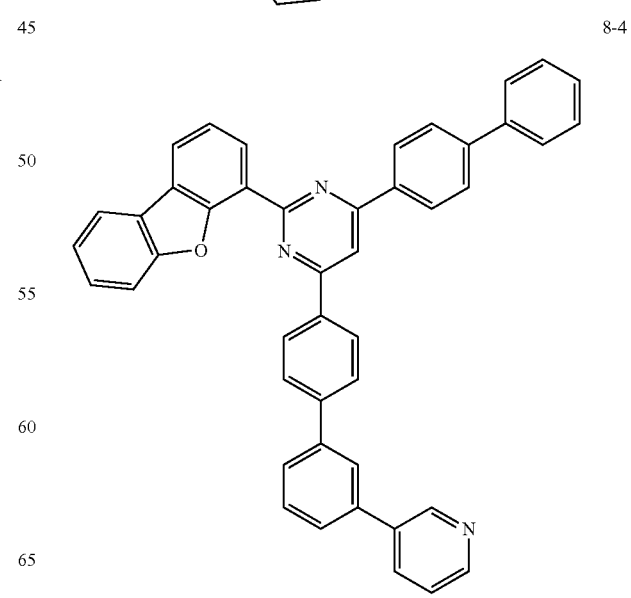

-continued
8-5
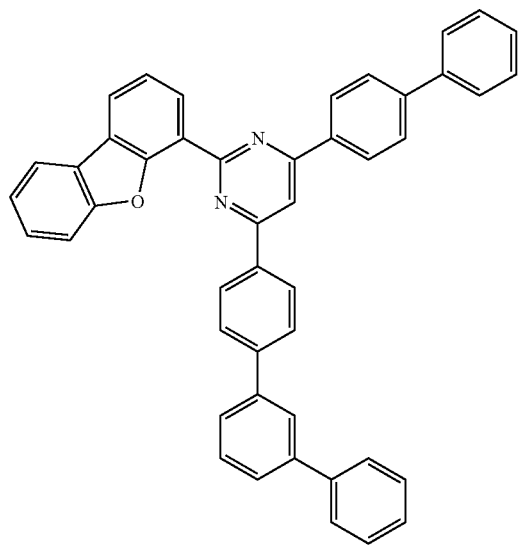
8-6
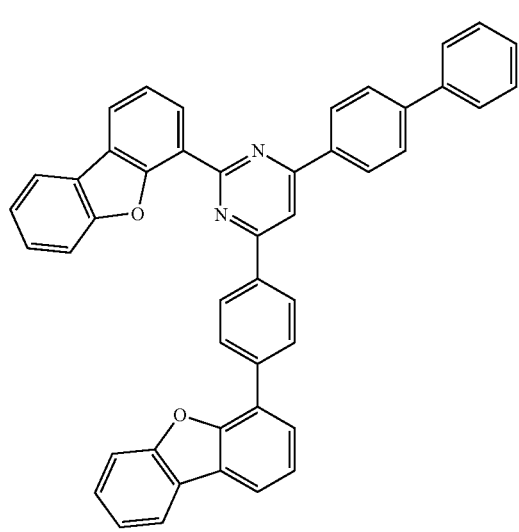
8-7
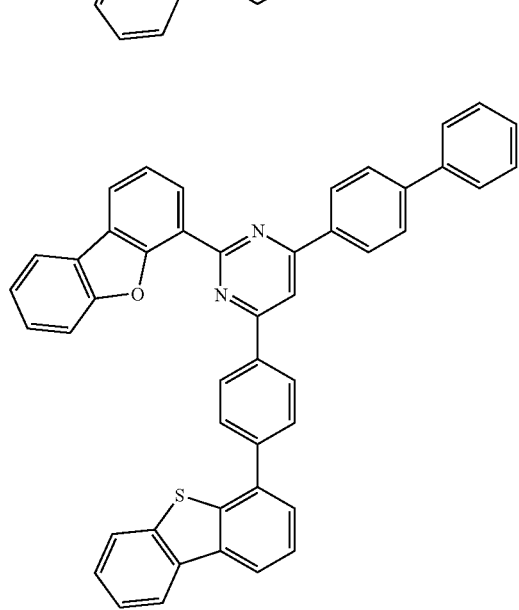
-continued
8-8
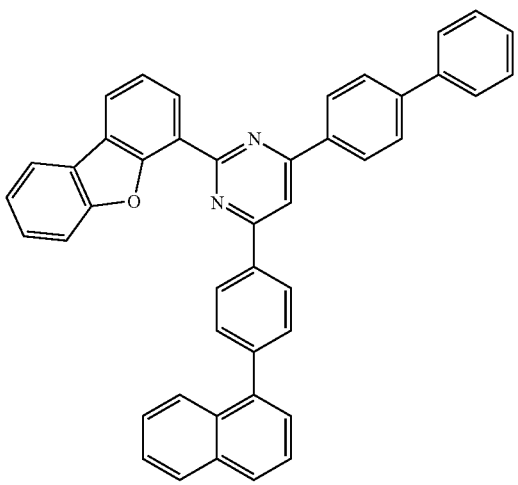
8-9
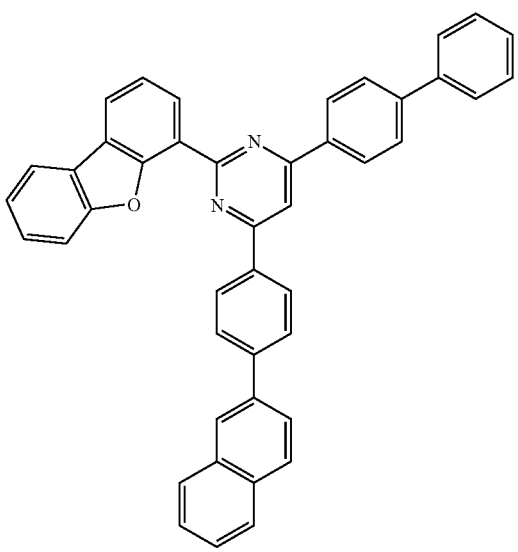
8-10
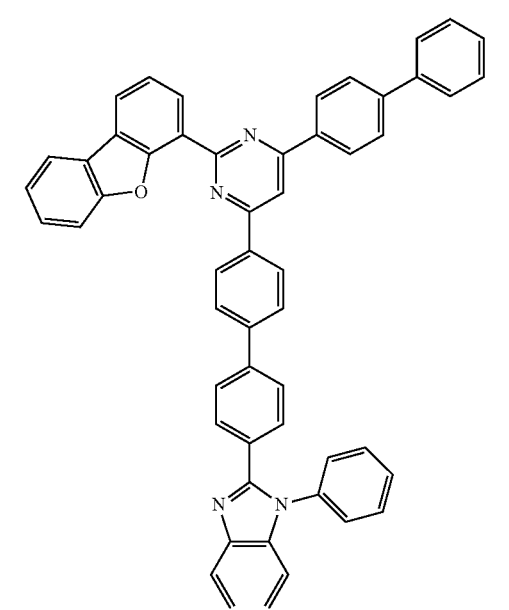

9-1
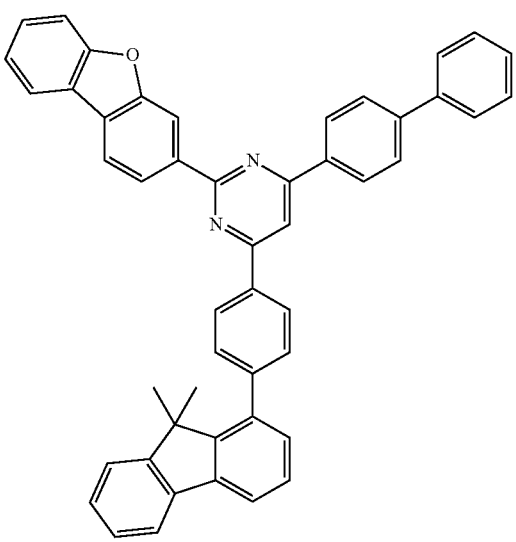
9-2
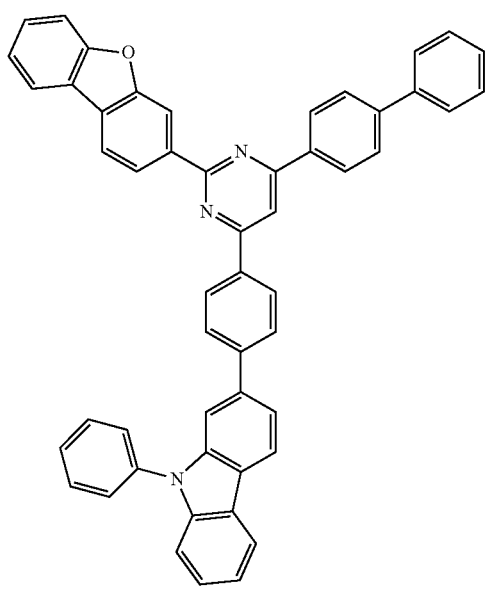
9-4
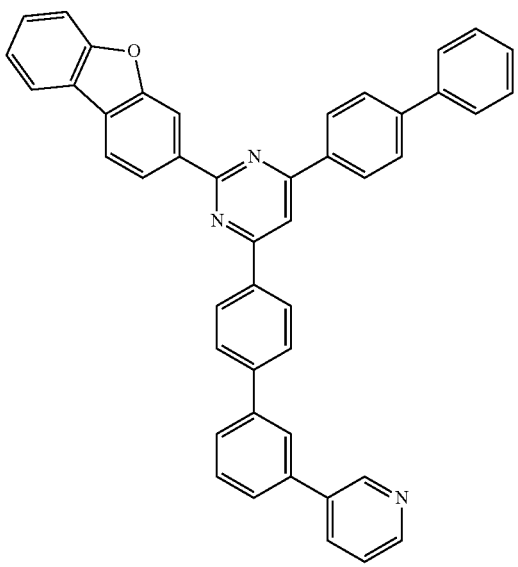
9-5
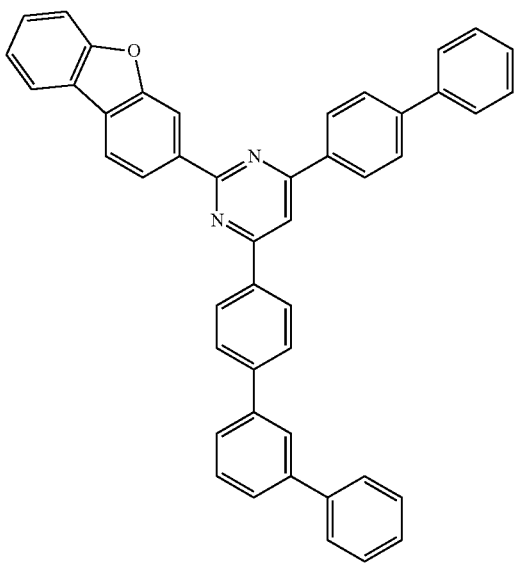
9-6
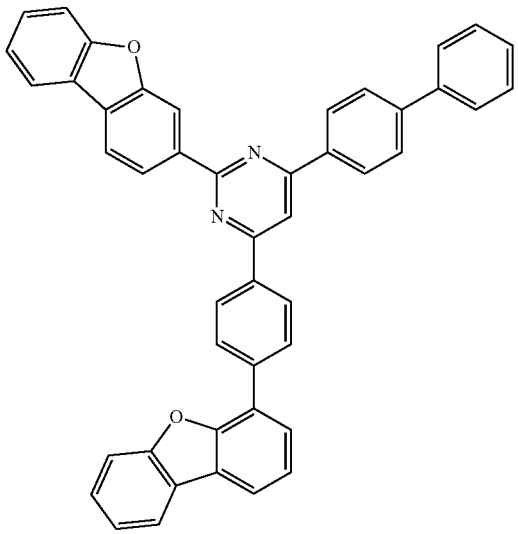
9-3

9-7
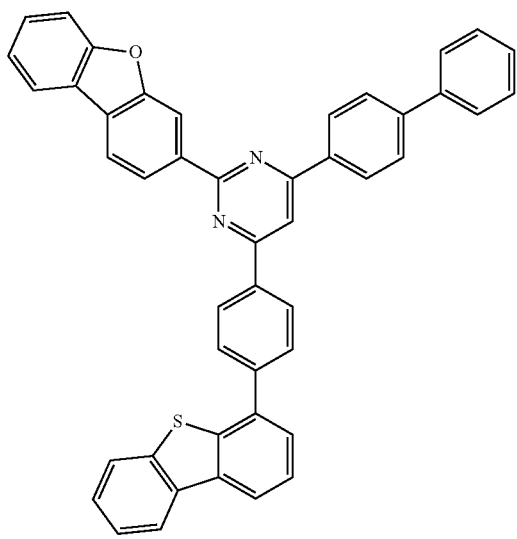
9-8
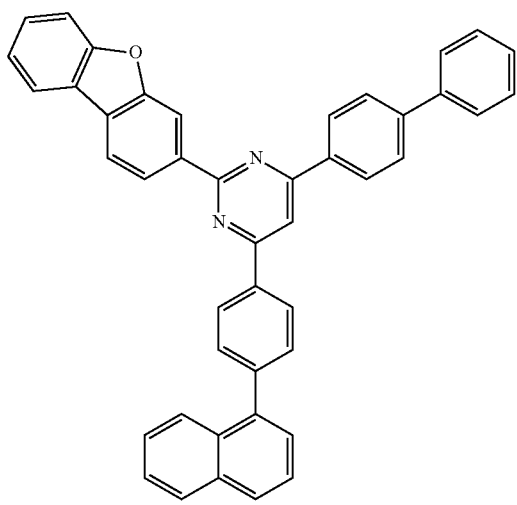
9-9
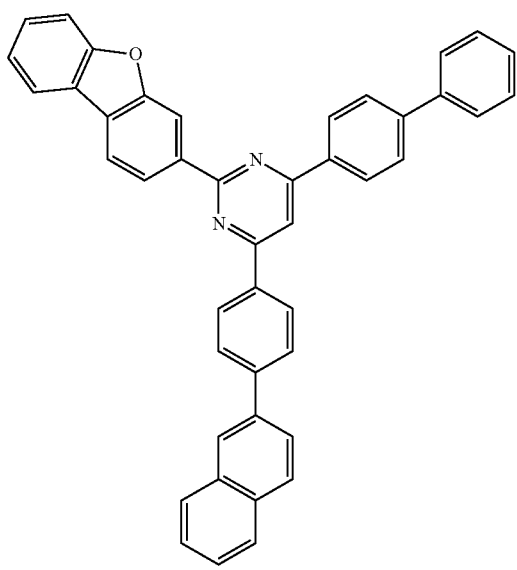
9-10
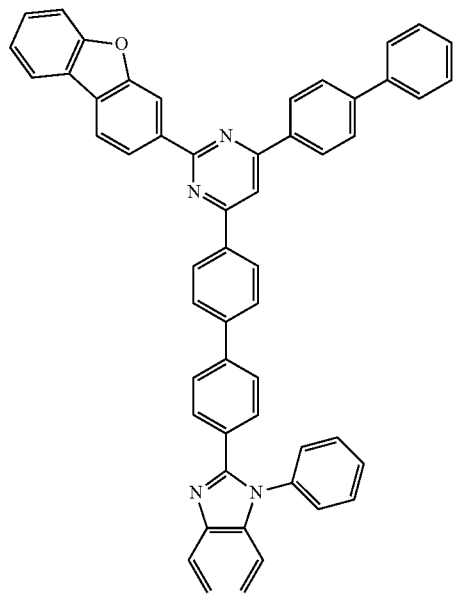
10-1
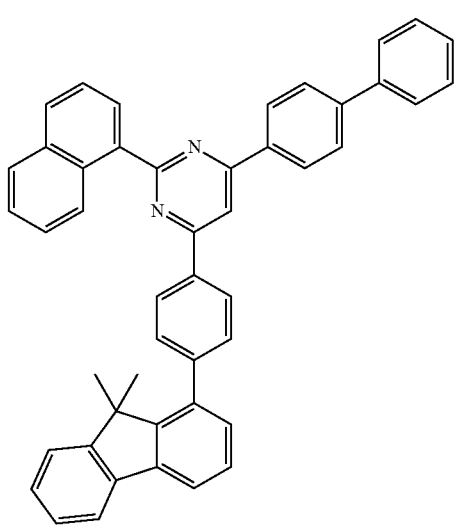
10-2
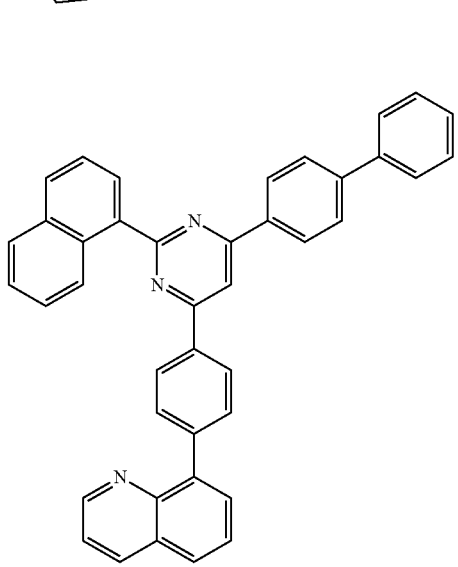

10-3
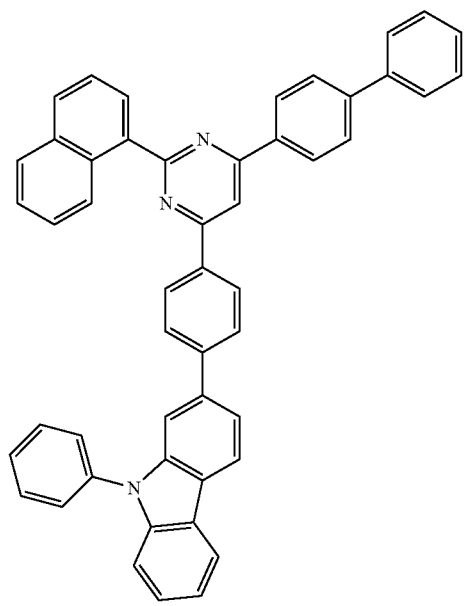
10-4
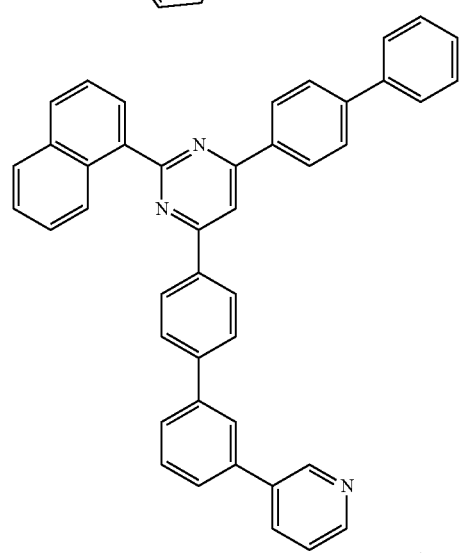
10-5
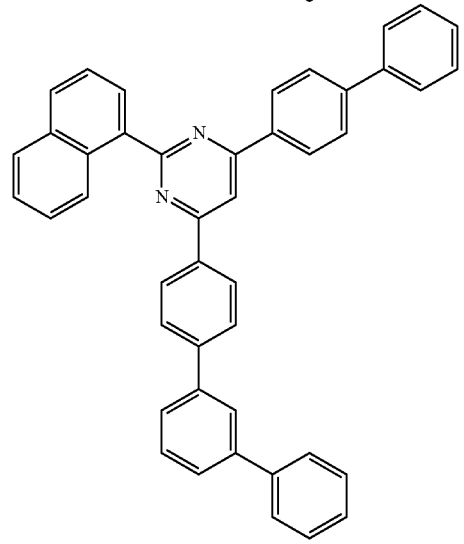
10-6
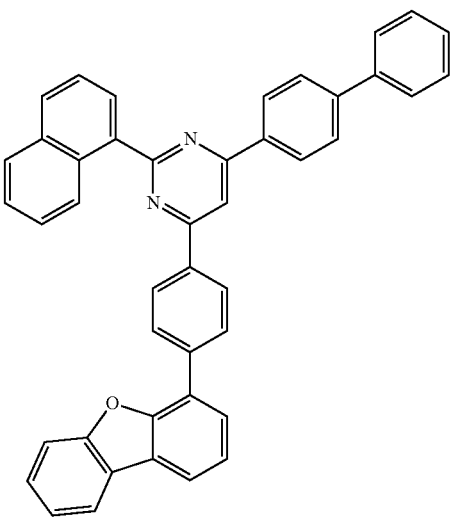
10-7
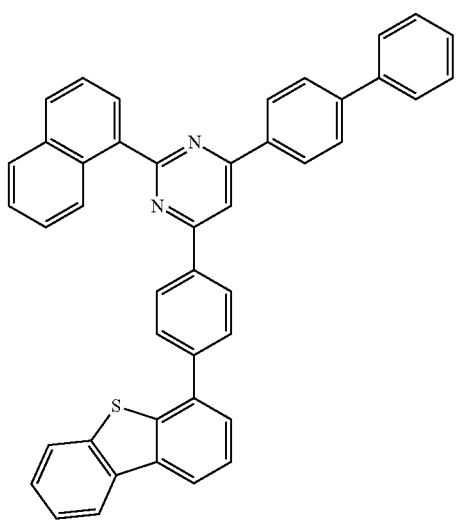
10-8
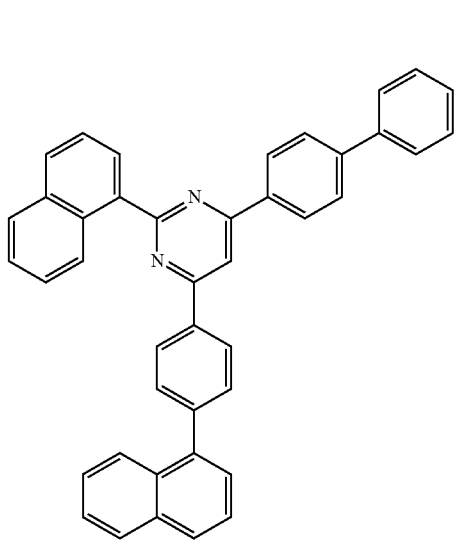

10-9
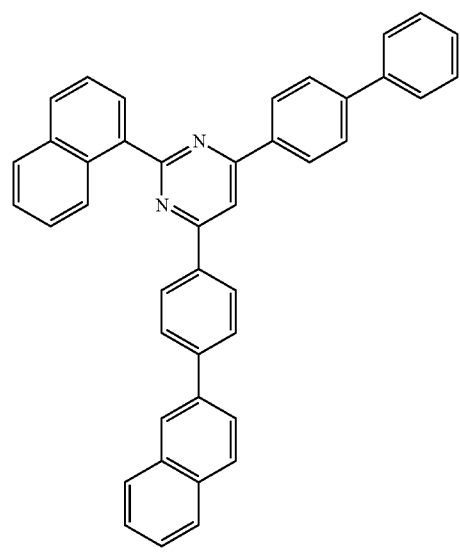
10-10
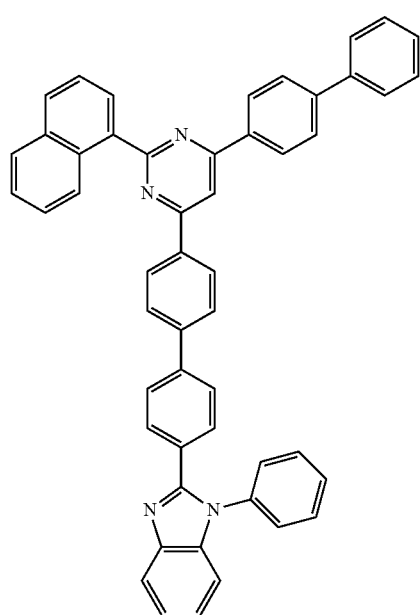
11-1
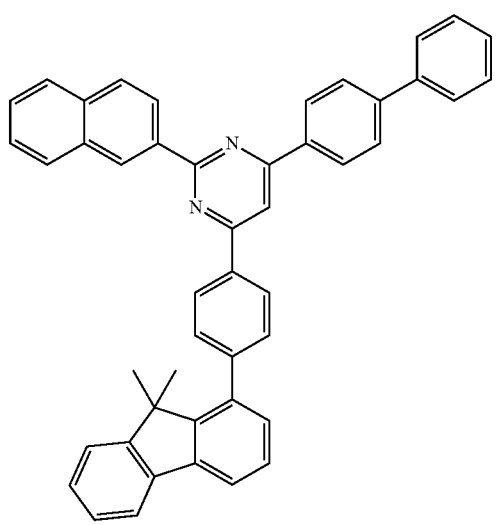
11-2
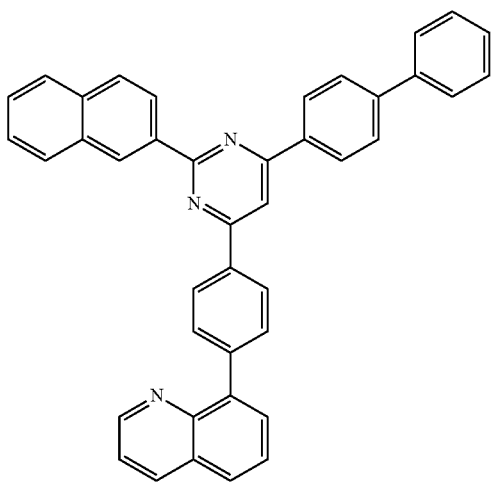
11-3
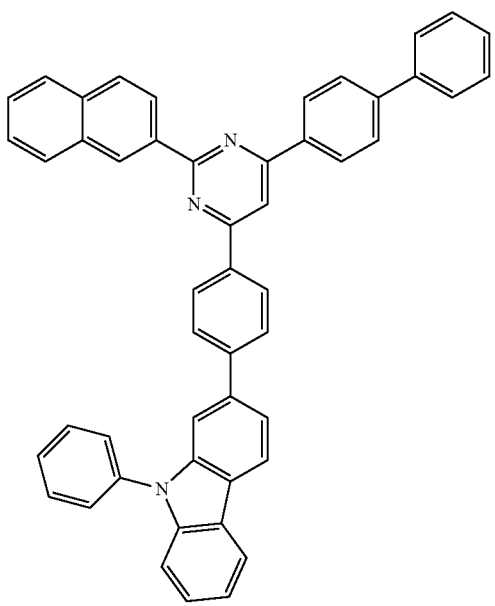
11-4
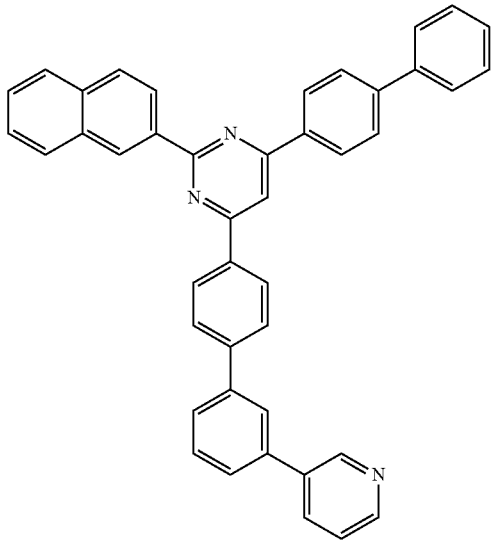

11-5
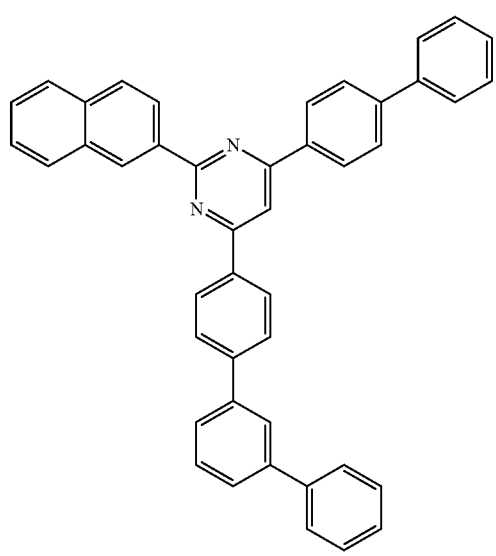
11-6
11-8
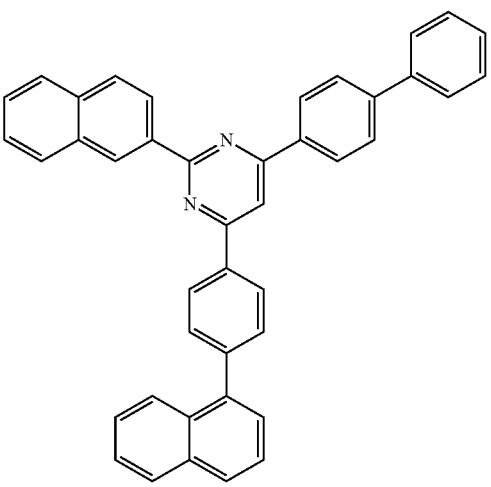
11-9
11-7
11-10
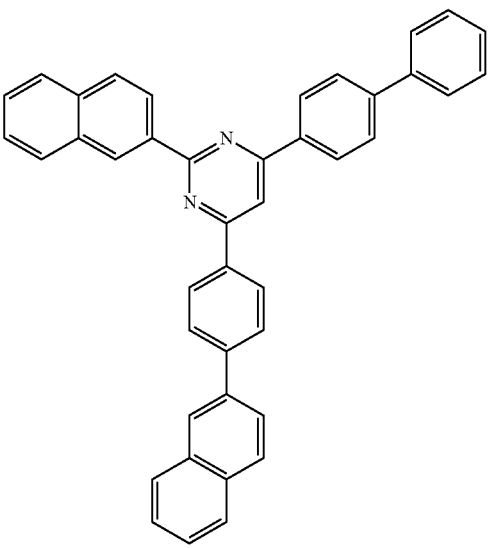
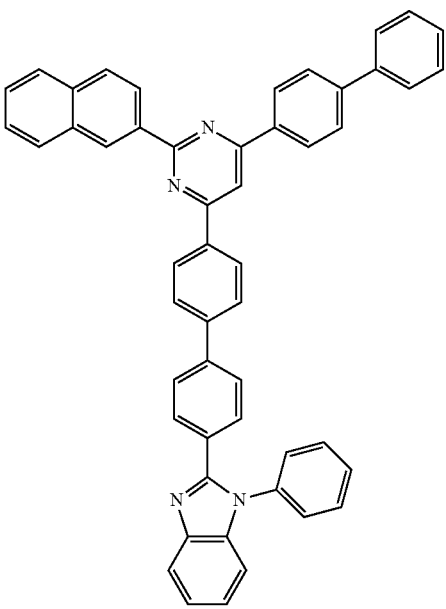

12-1
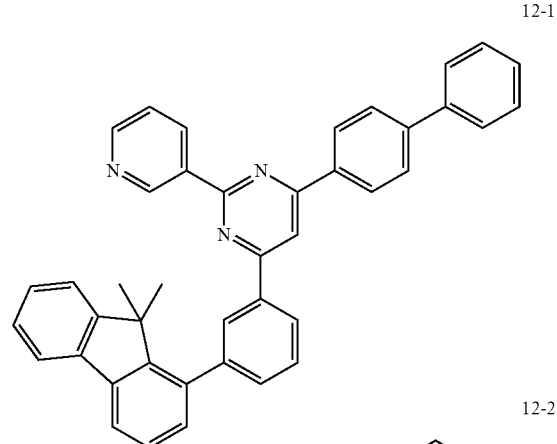
12-2
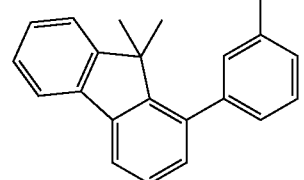
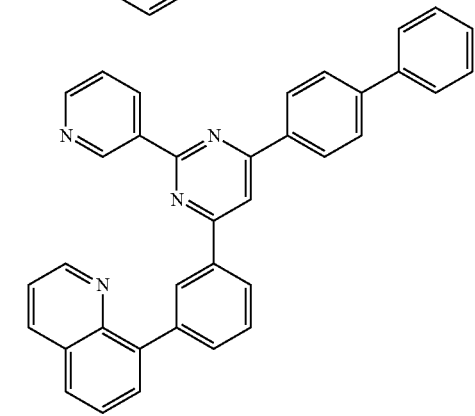
12-3
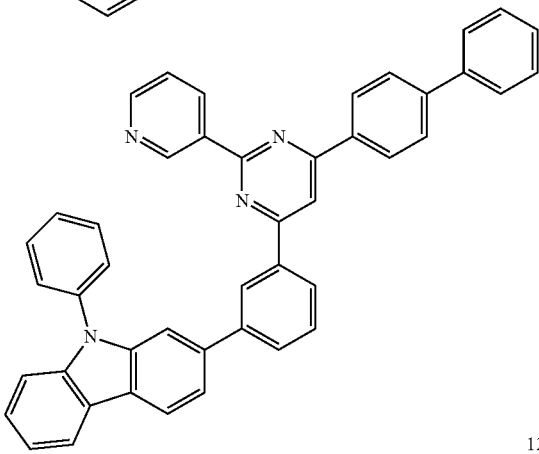
12-4
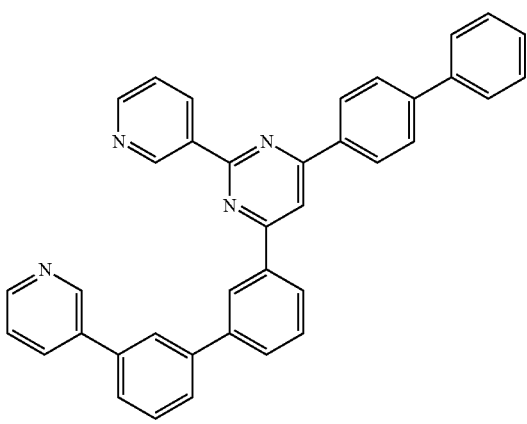
12-5
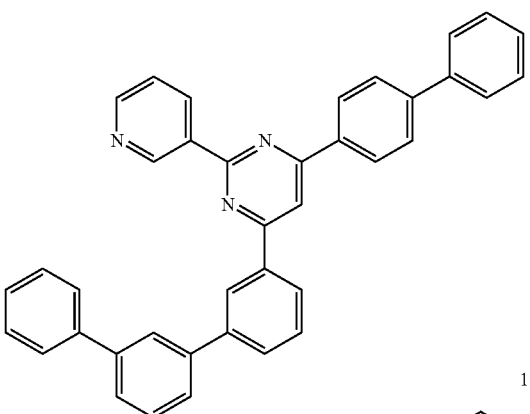
12-6
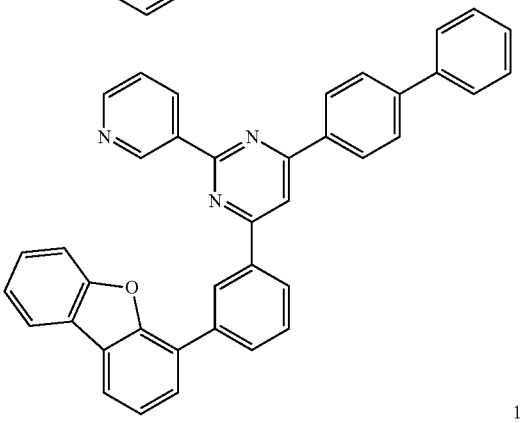
12-7
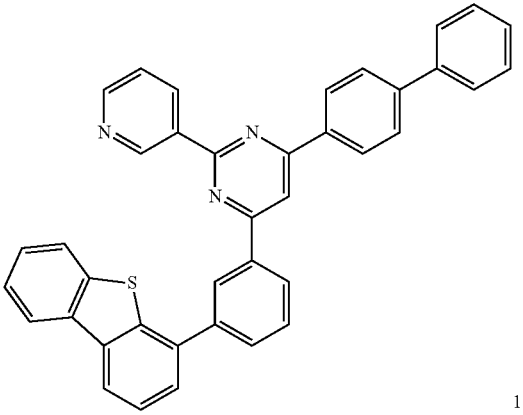
12-8
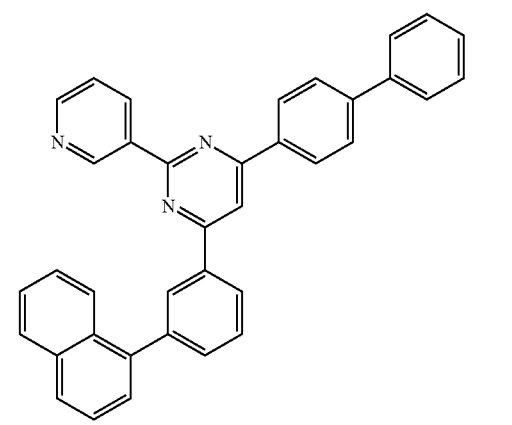

12-9
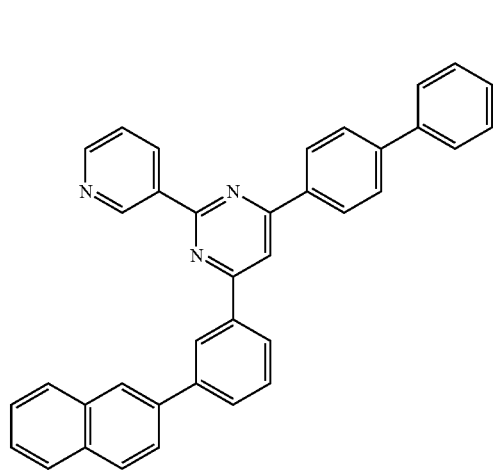
12-10
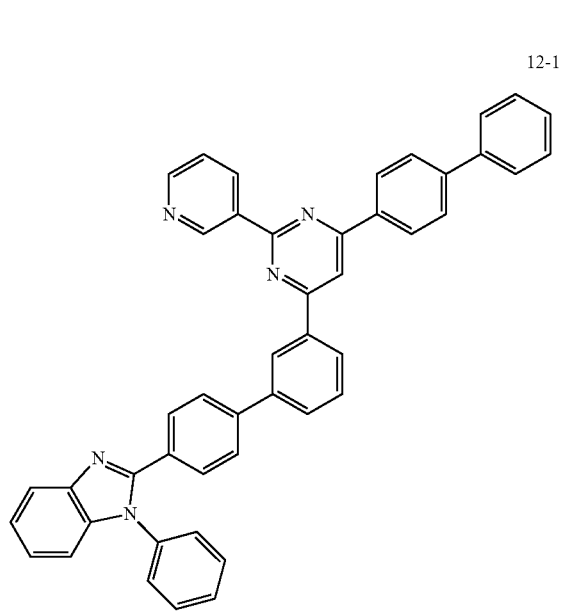
13-1
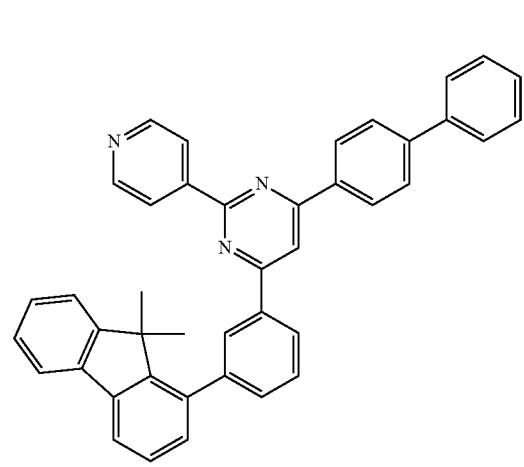
13-2
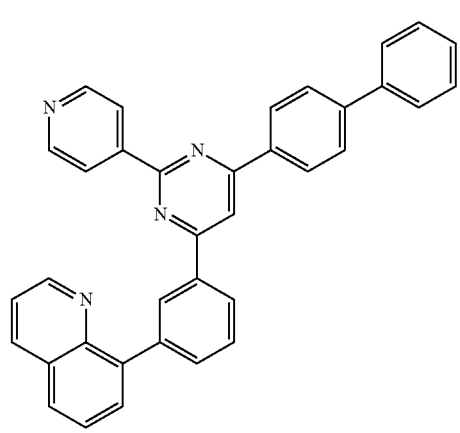
13-3
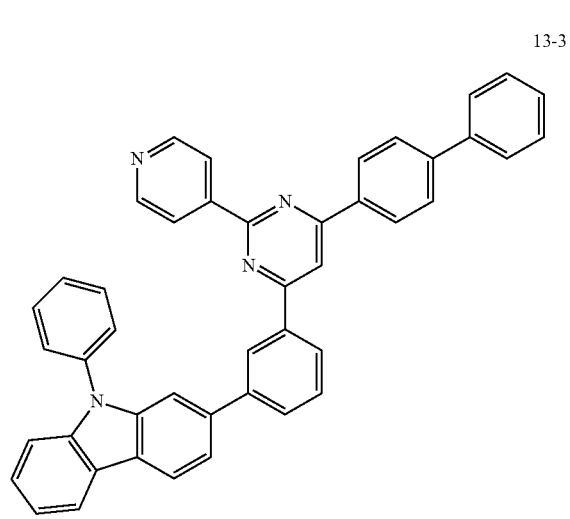
13-4
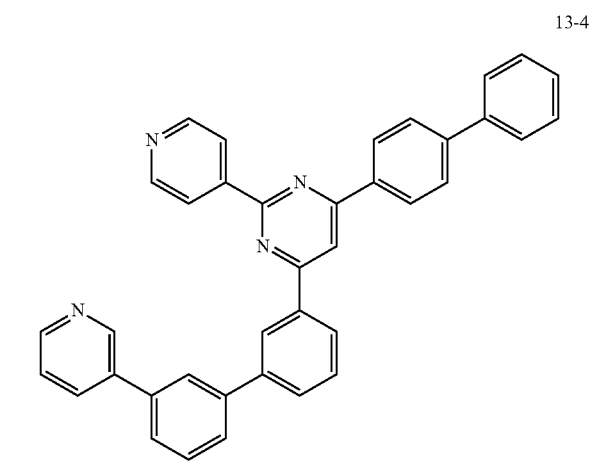

13-5
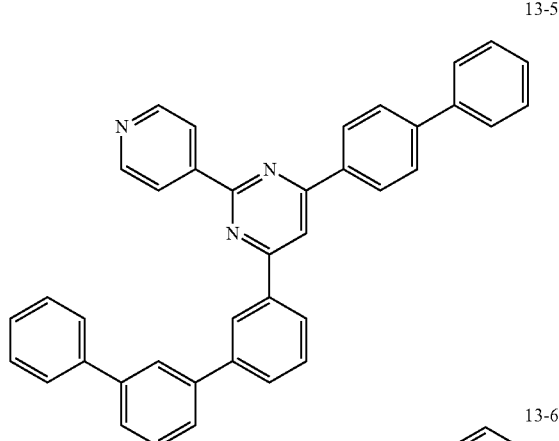
13-6
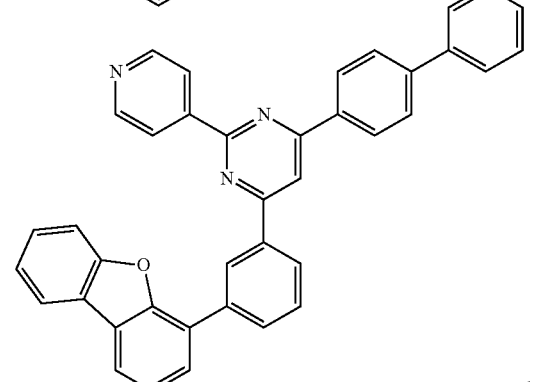
13-7
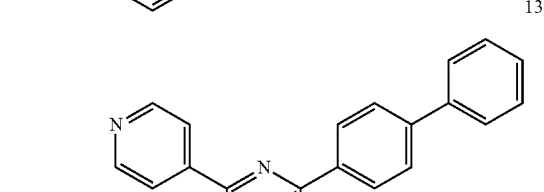
13-8
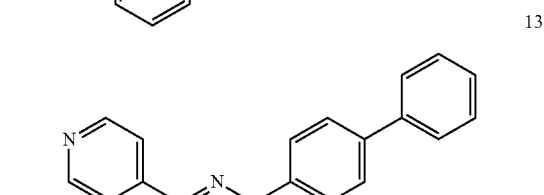
13-9
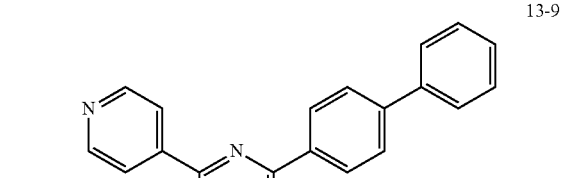
13-10
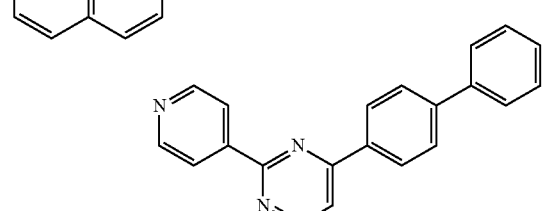
14-1
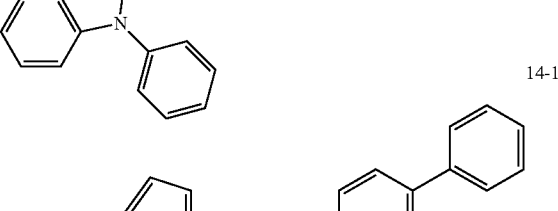
14-2
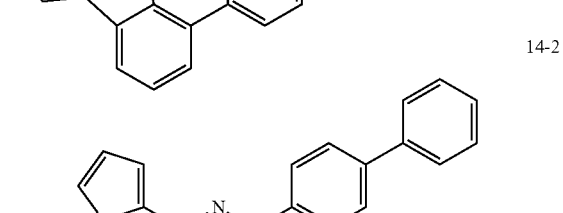

14-3
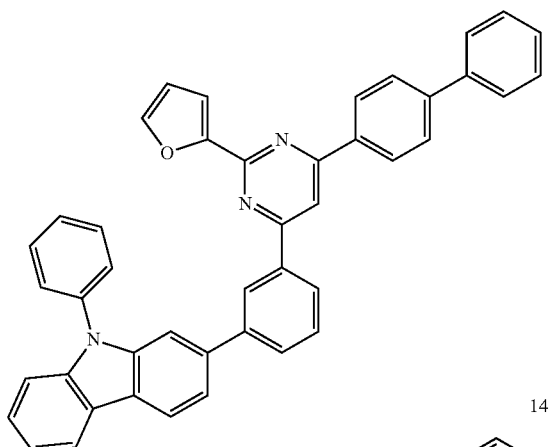
14-4
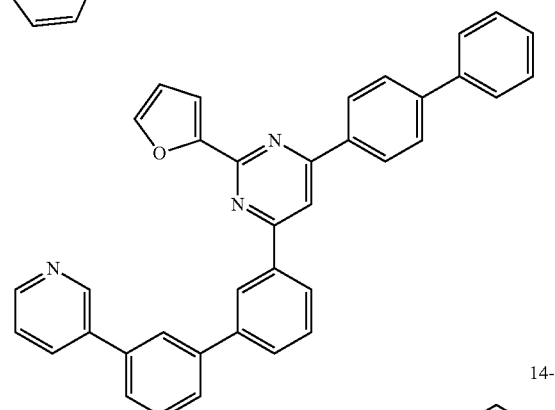
14-5
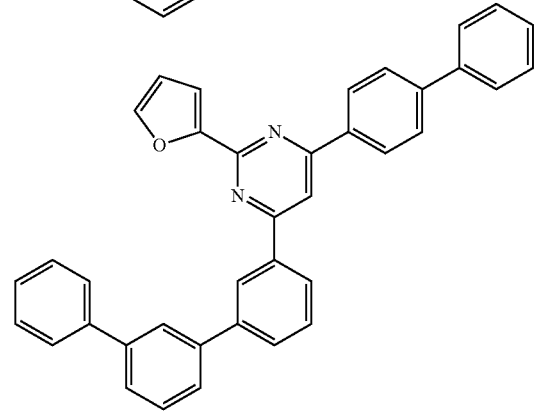
14-6
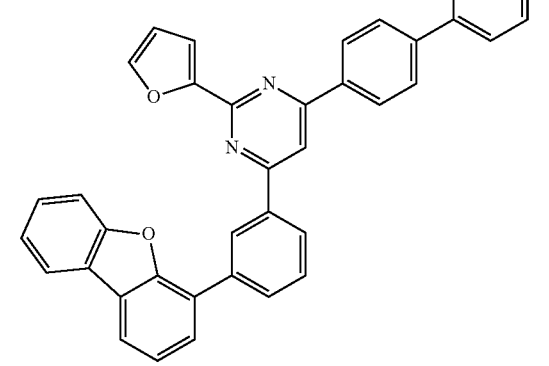
14-7
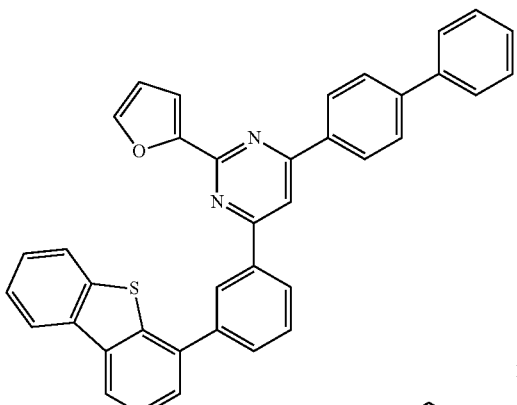
14-8
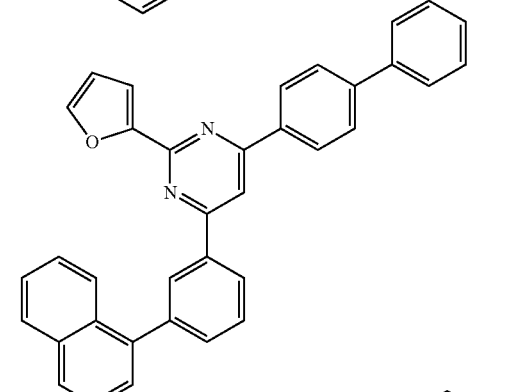
14-9
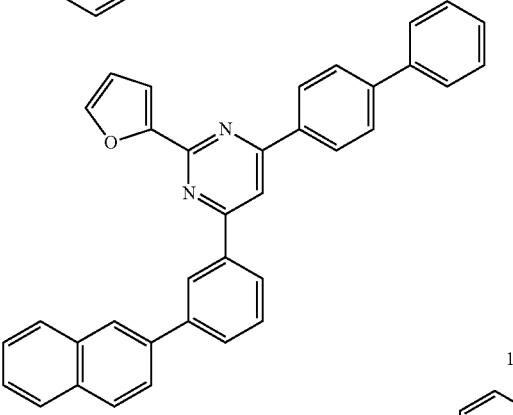
14-10
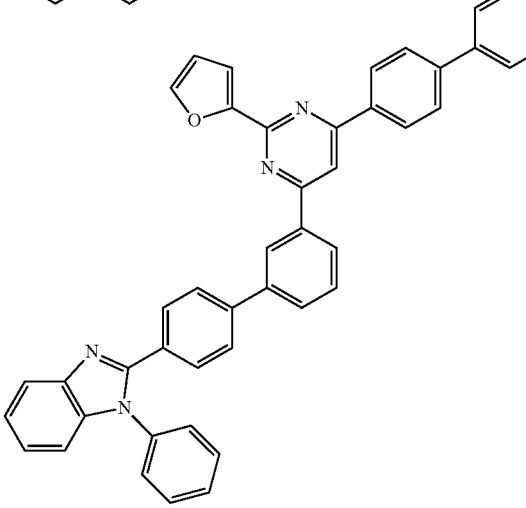

-continued
15-1
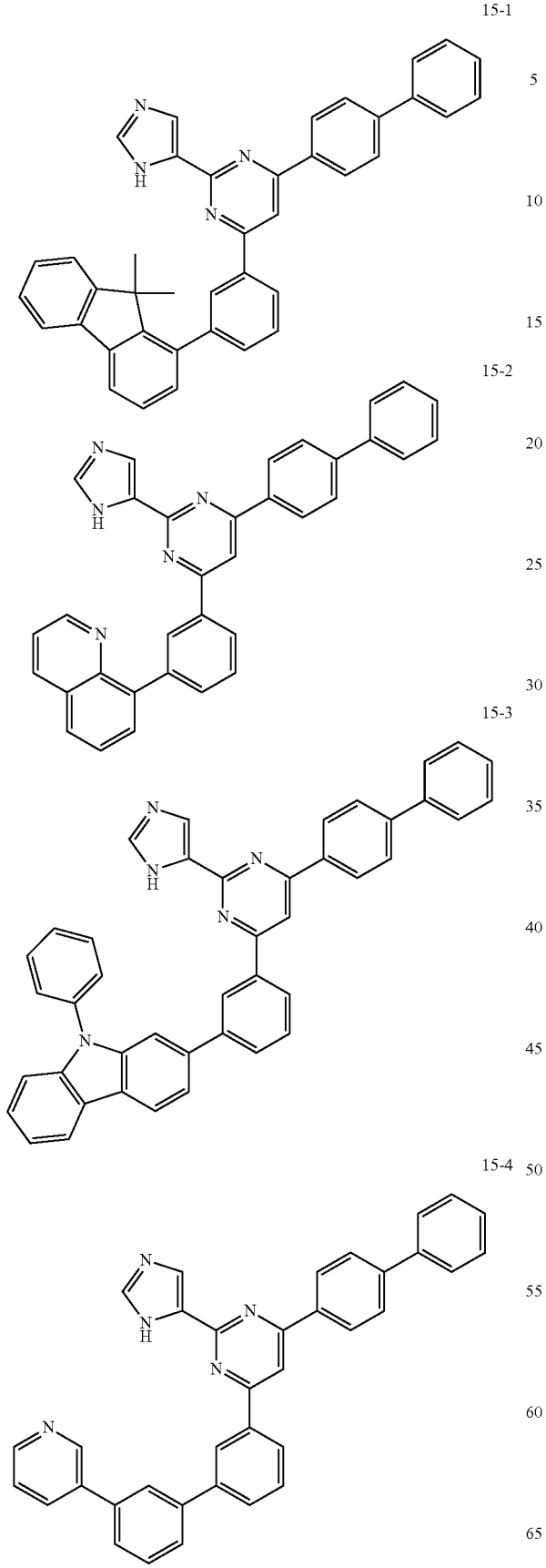
15-2
15-3
15-4
-continued
15-5
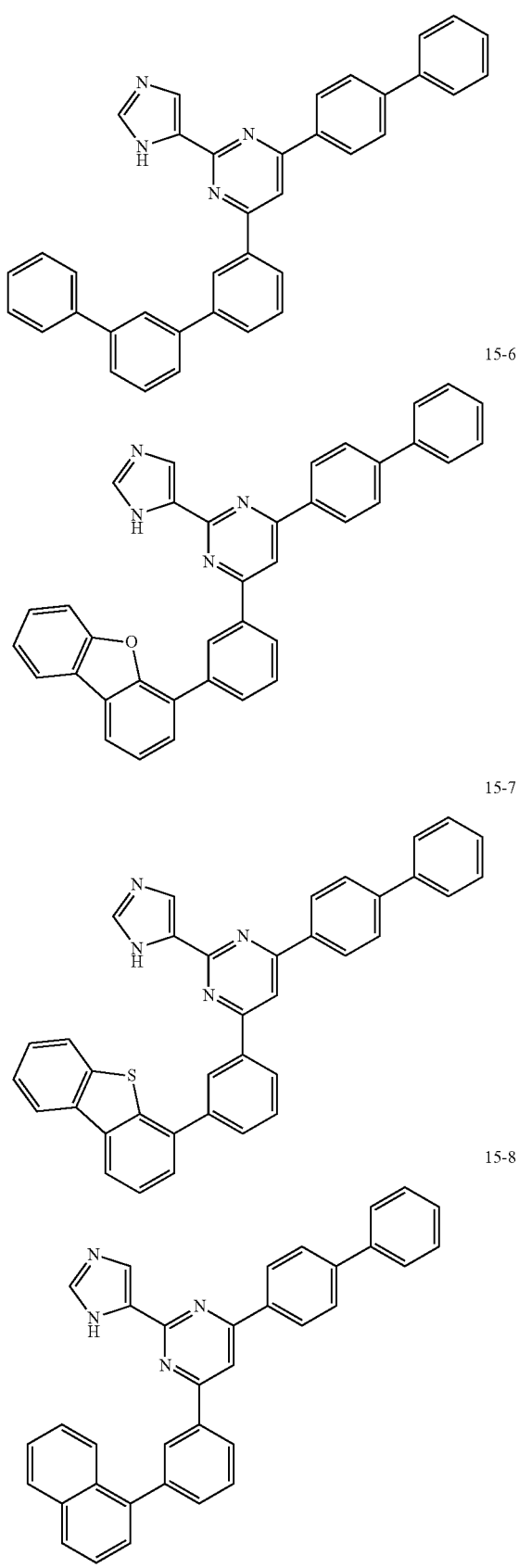
15-6
15-7
15-8

15-9
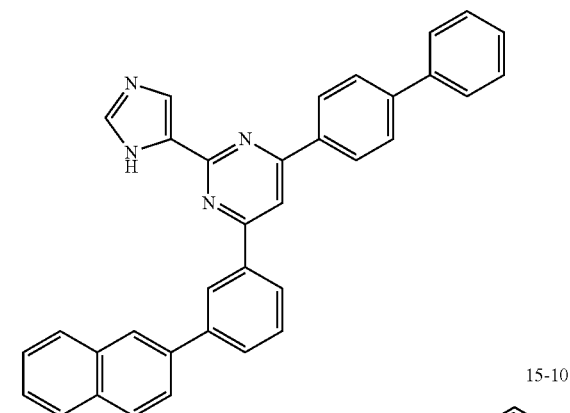
15-10
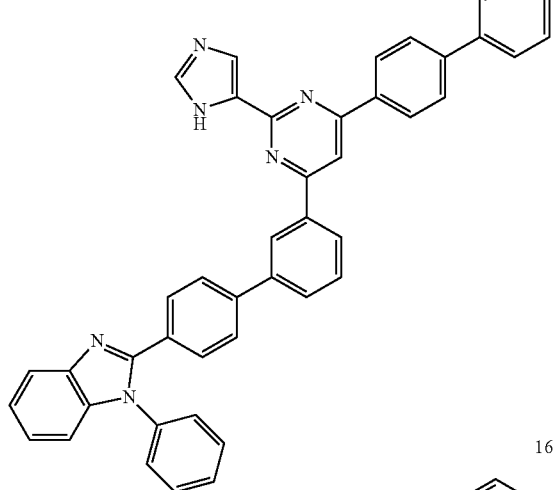
16-1
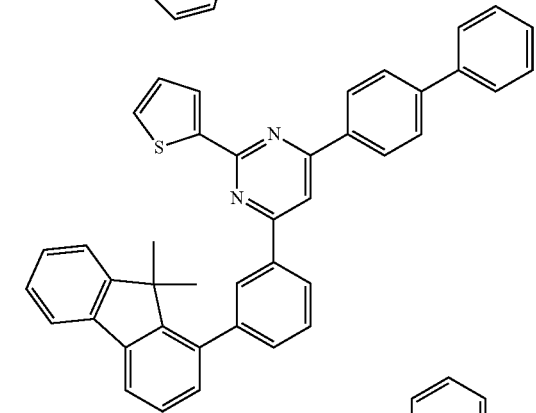
16-2
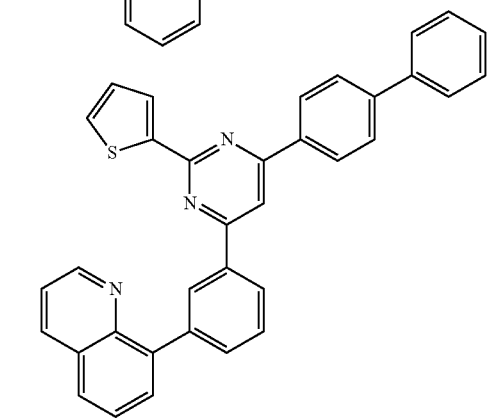
16-3
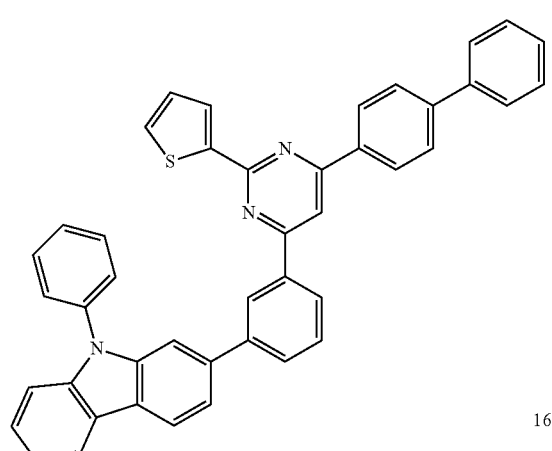
16-4
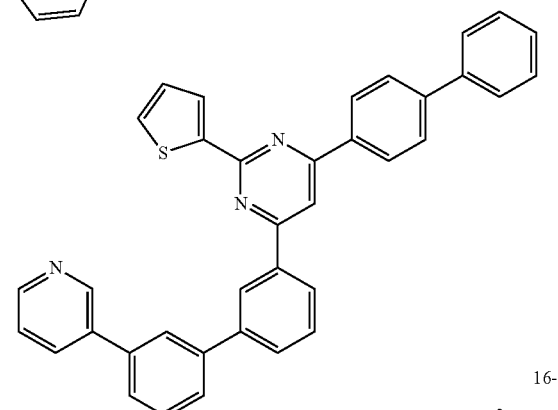
16-5
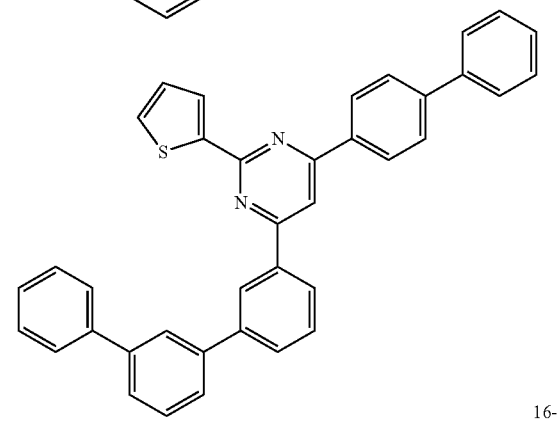
16-6
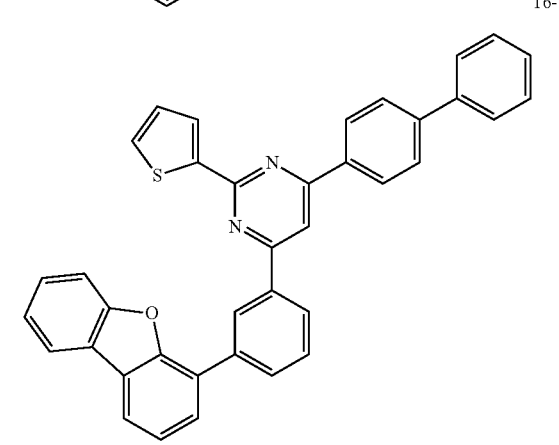

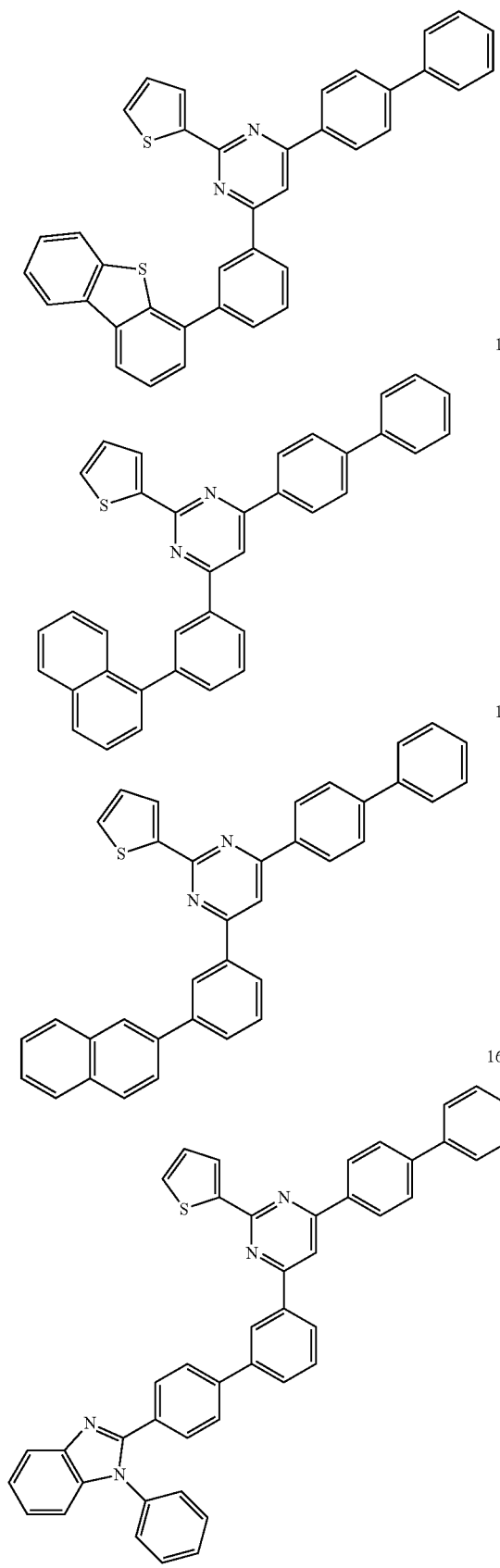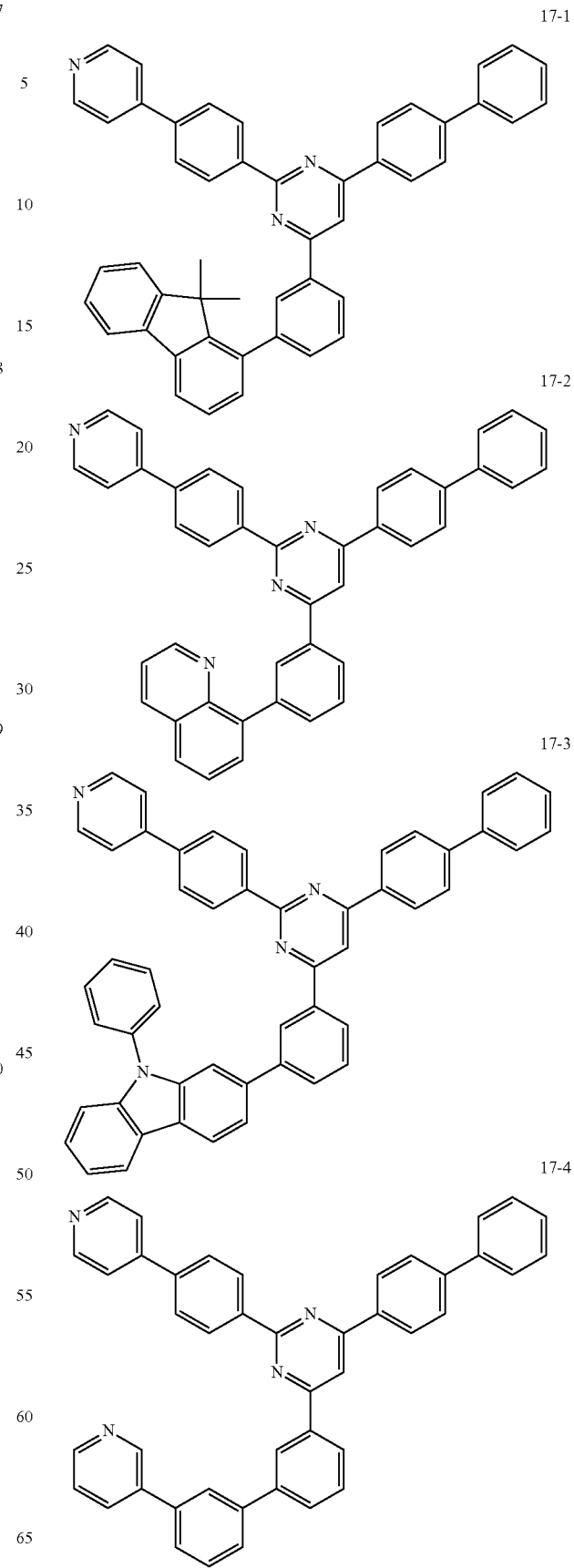

17-5
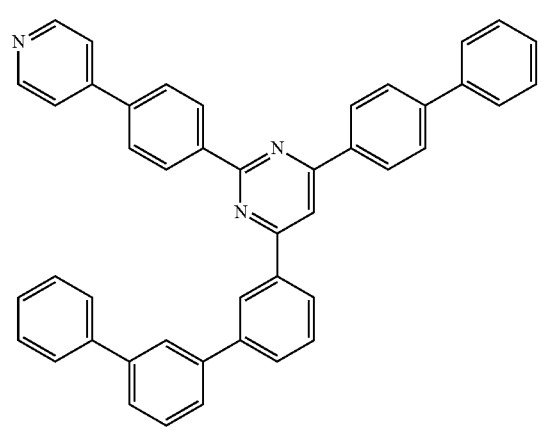
17-6
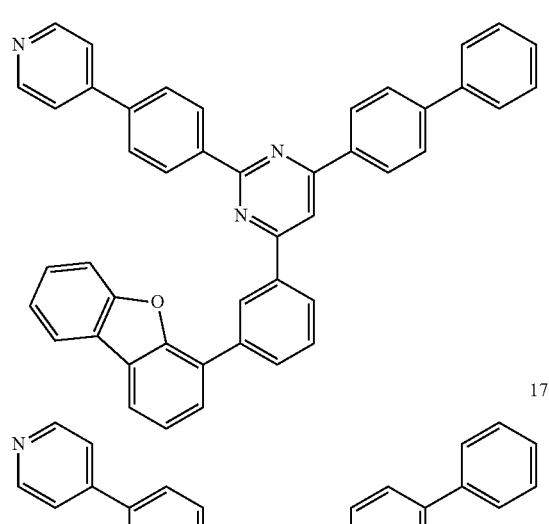
17-7
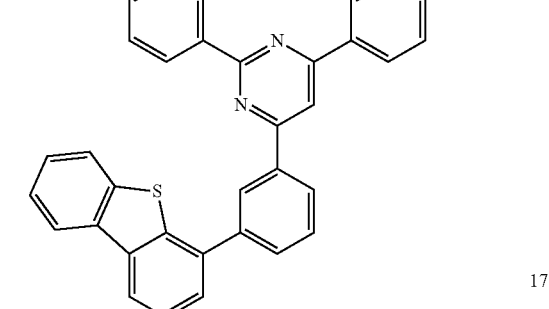
17-8
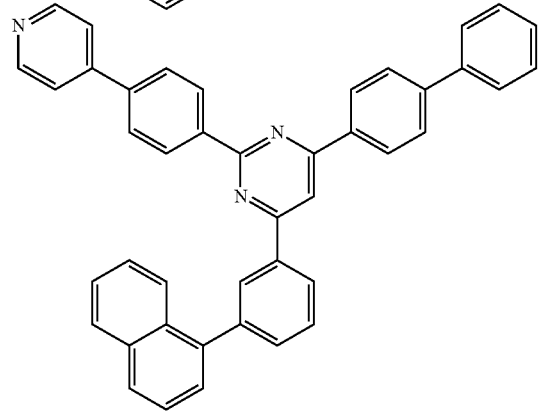
17-9
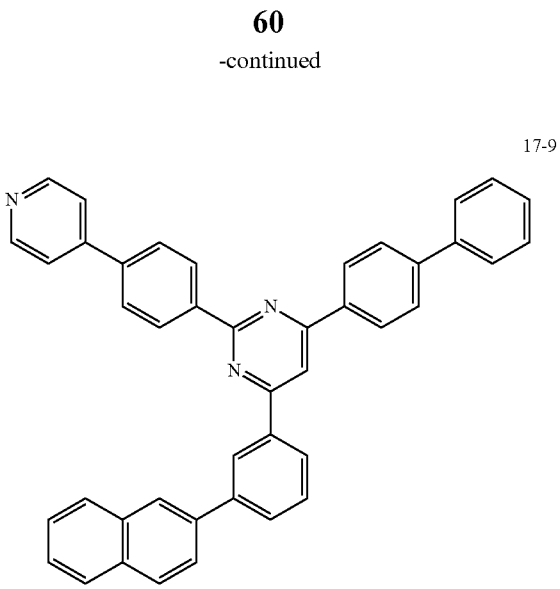
17-10
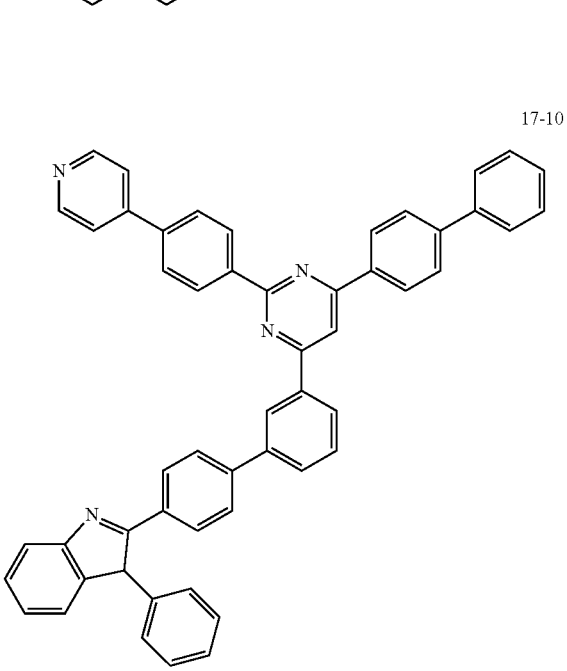
18-1
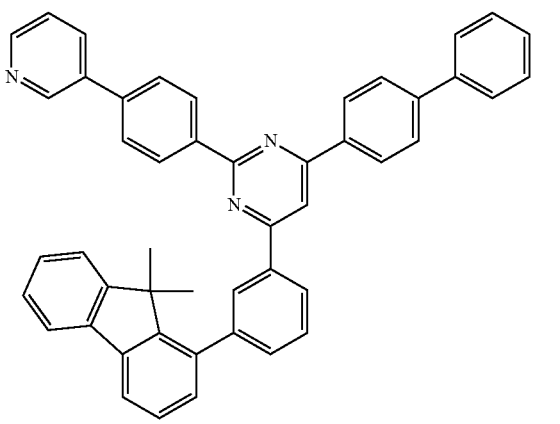

-continued
18-2
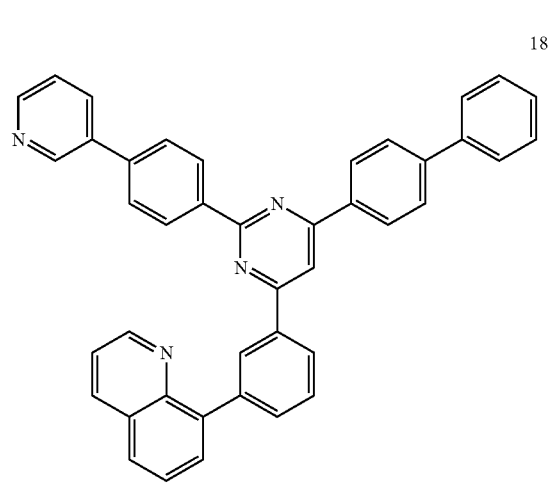
18-3
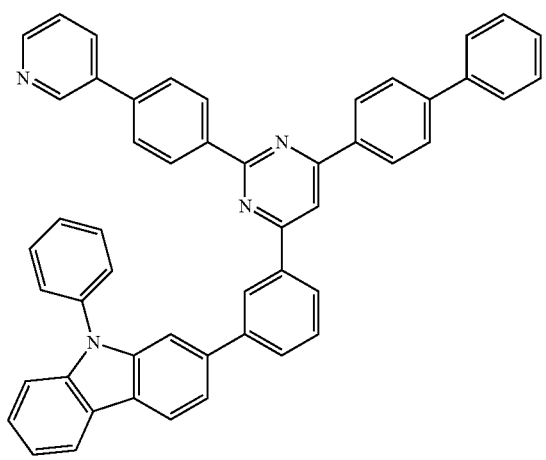
18-4
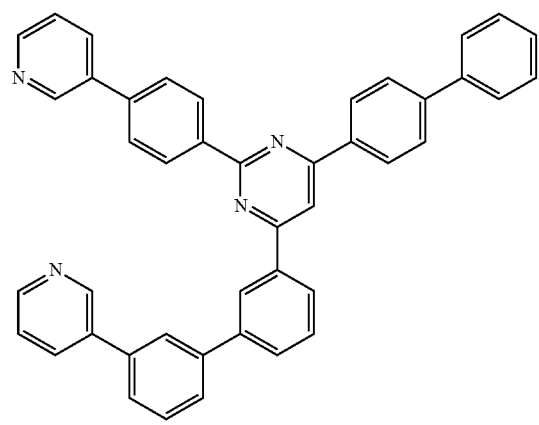
-continued
18-5
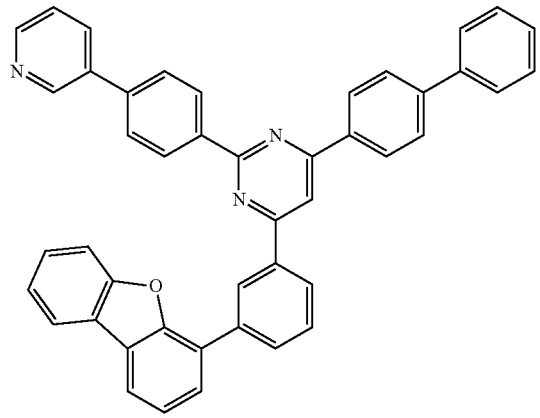
18-6
18-7
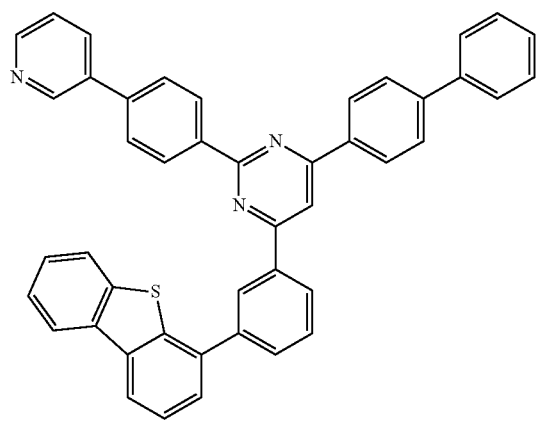

18-8
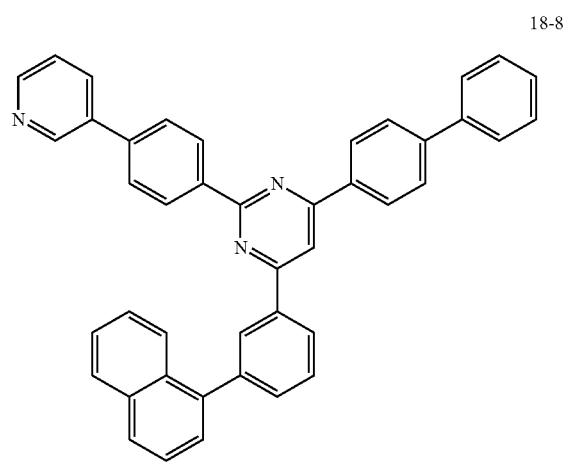
18-9
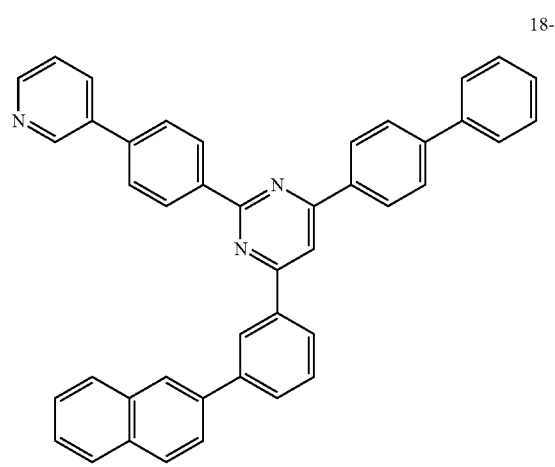
18-10
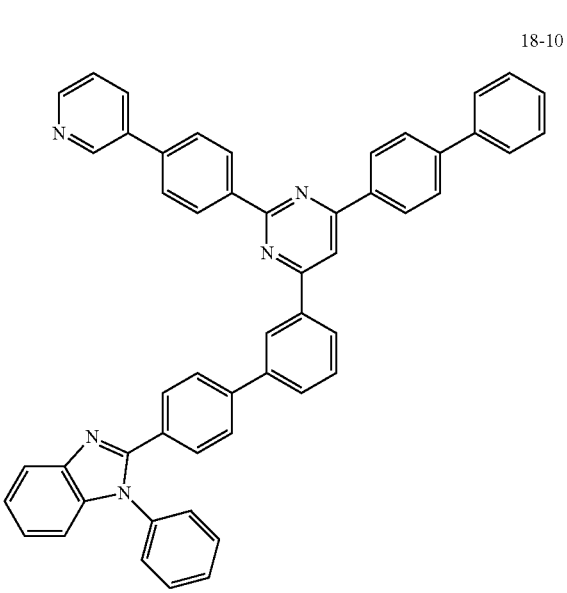
19-1
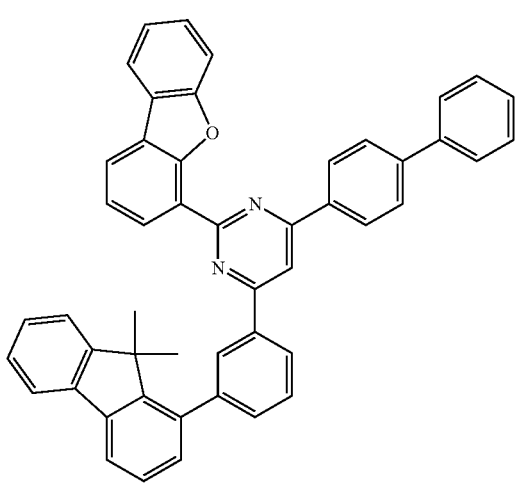
19-2
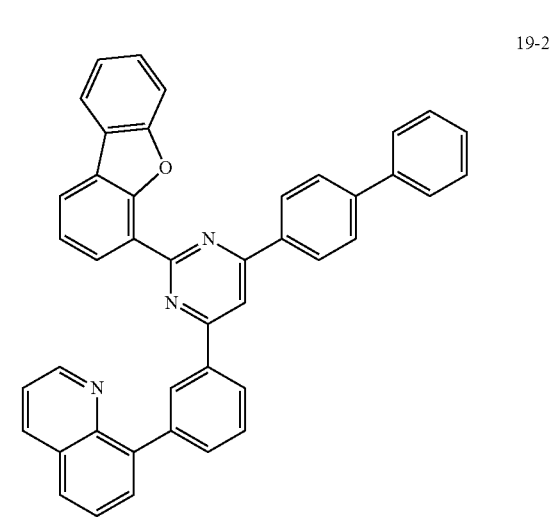
19-3
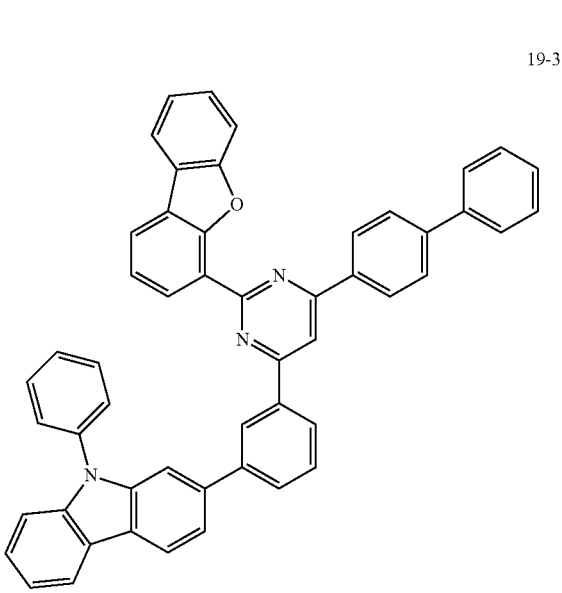

19-4
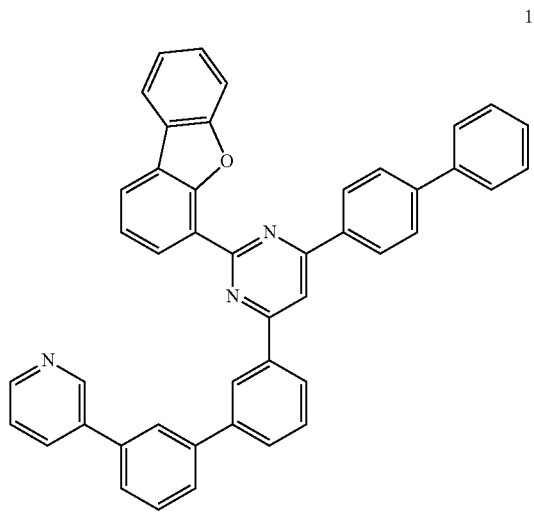
19-5
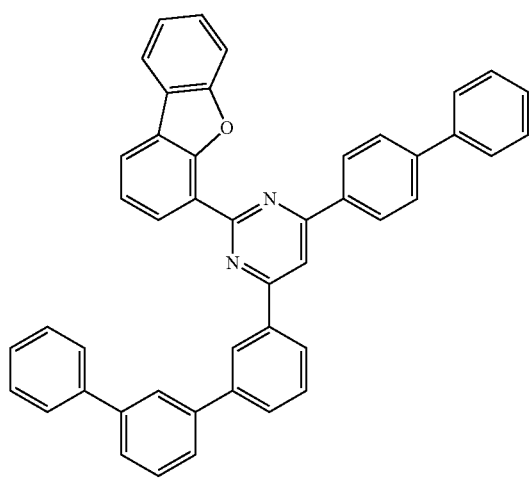
19-6
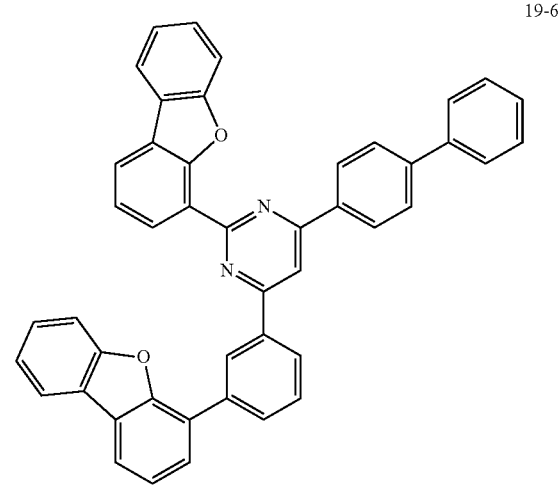
19-7
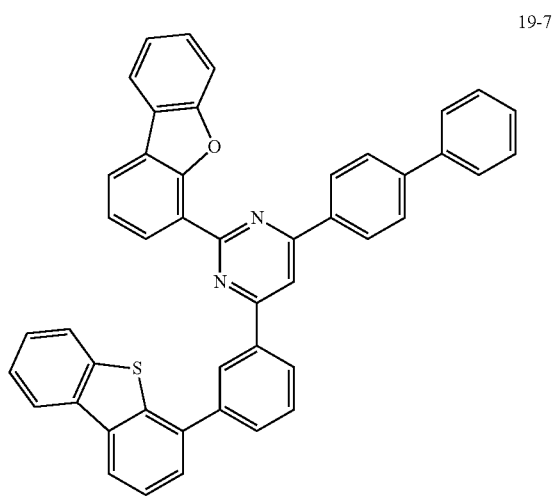
19-8
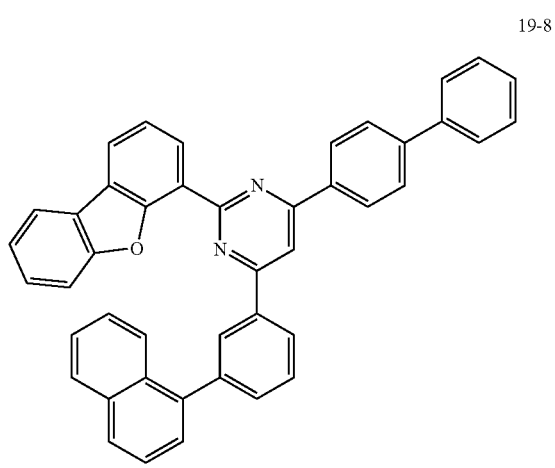
19-9
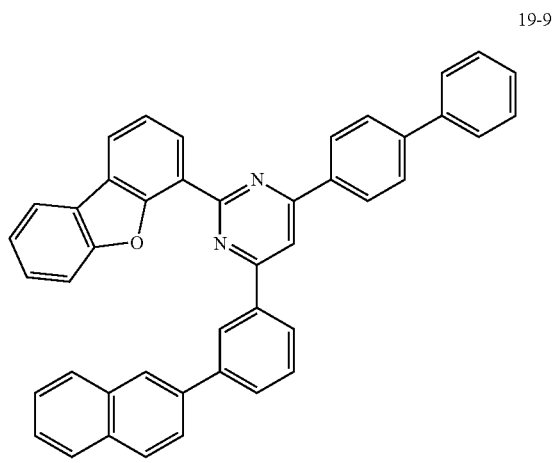

19-10
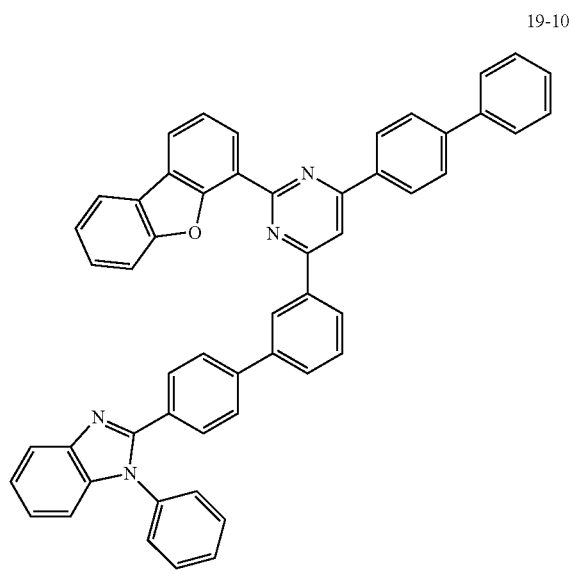
20-3
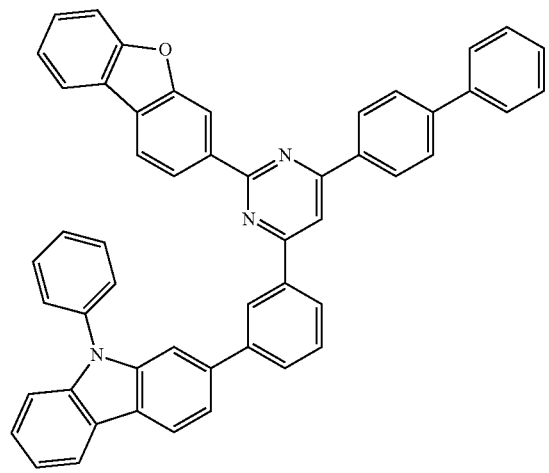
20-1
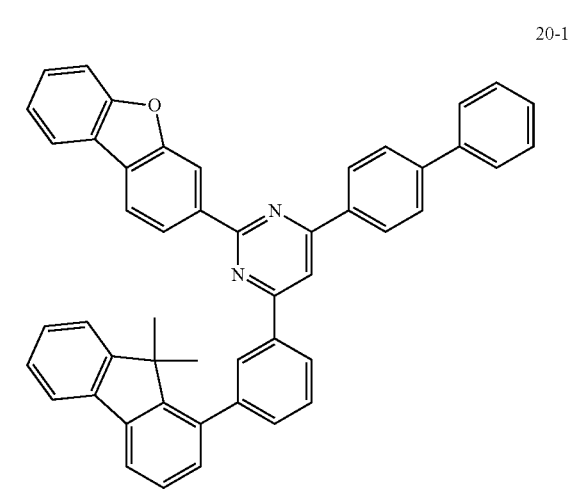
20-4
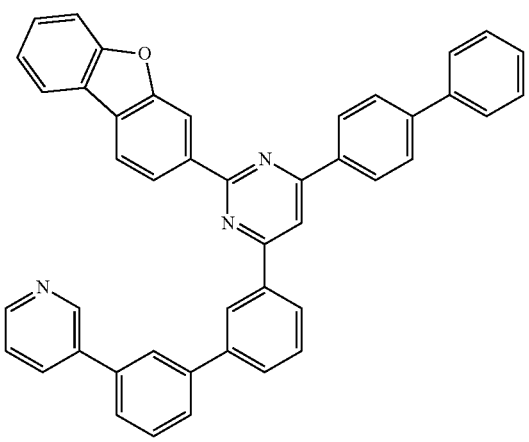
20-2
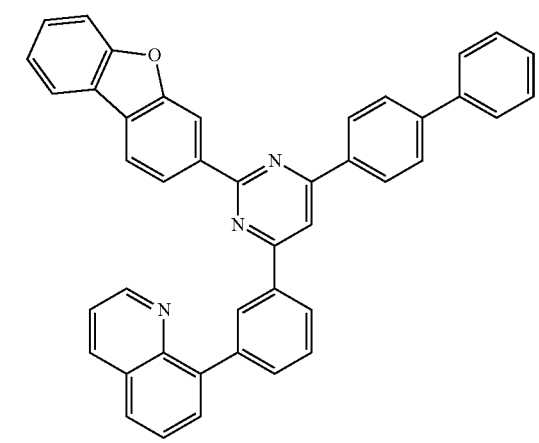
20-5

20-6
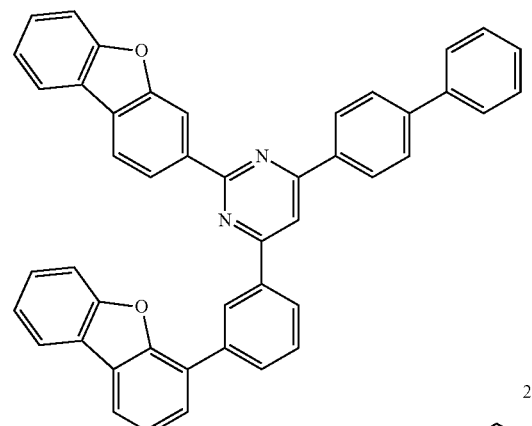
20-7
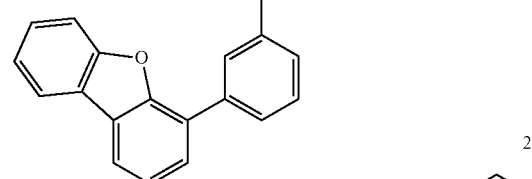
20-8
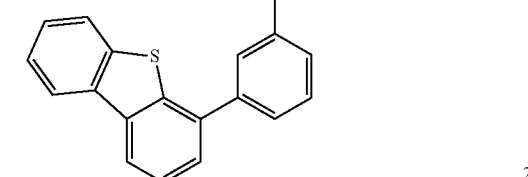
20-9
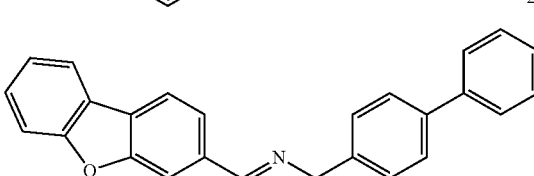
20-10
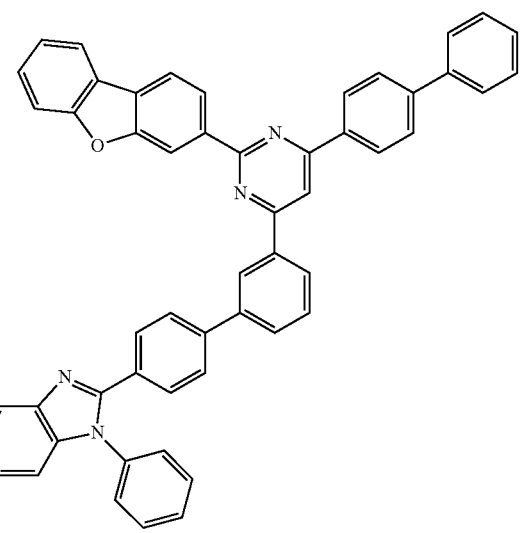
21-1
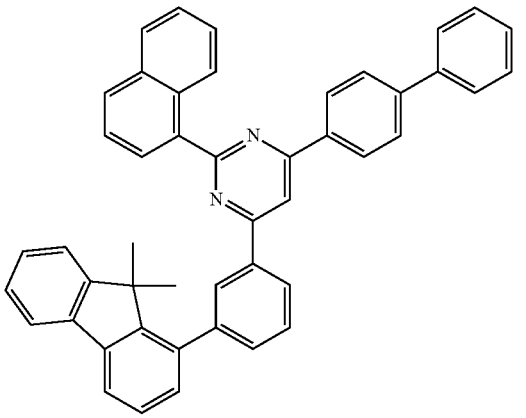
21-2
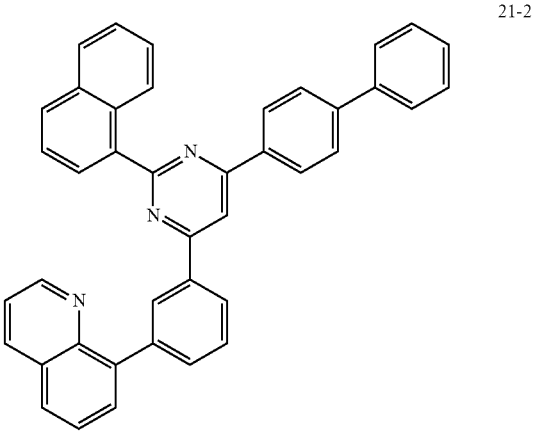

21-3
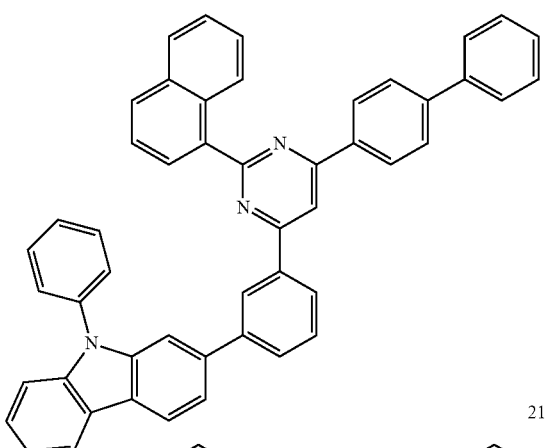
21-4
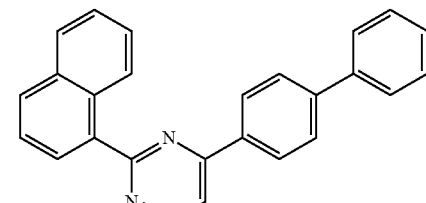
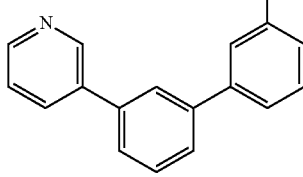
21-5
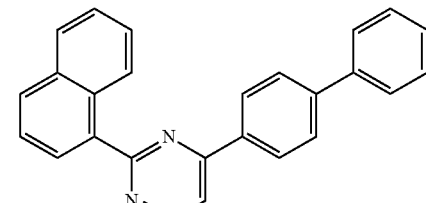
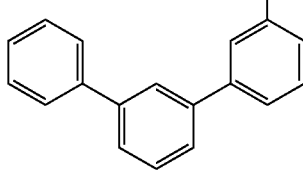
21-6
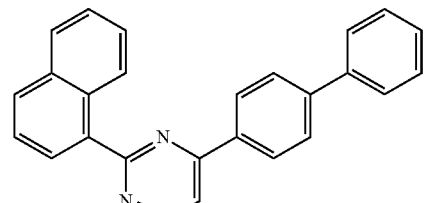
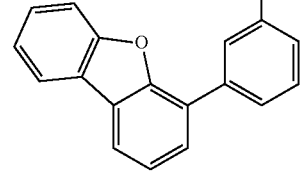
21-7
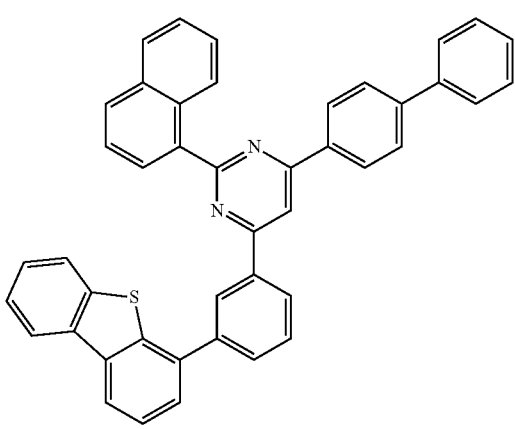
21-8
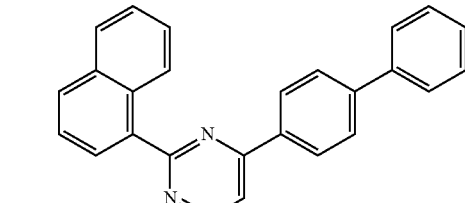
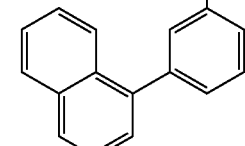
21-9
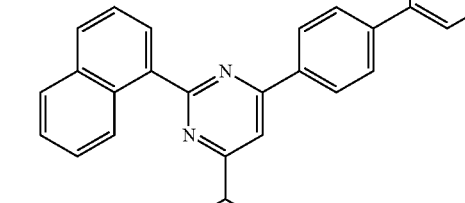
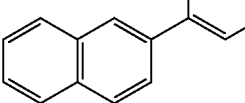
21-10
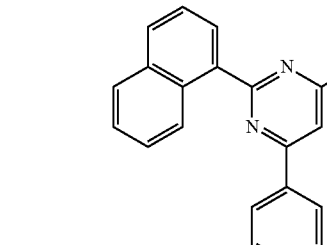
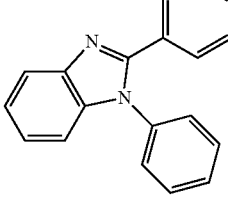

-continued
22-1
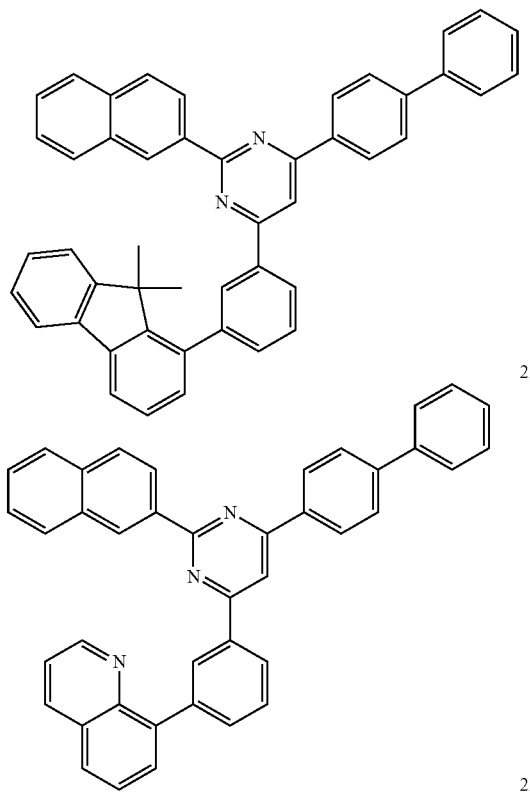
22-2
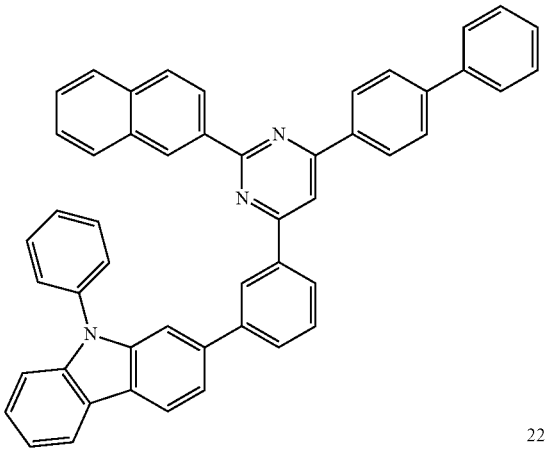
22-3
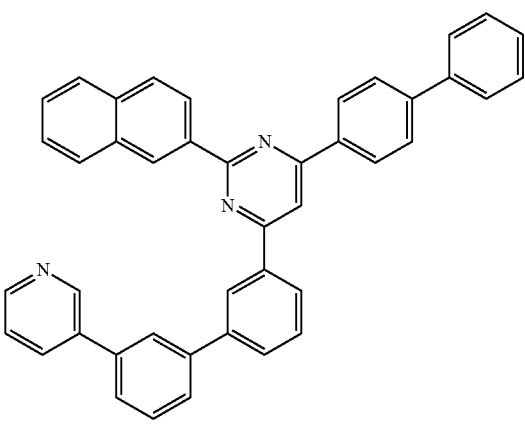
22-4
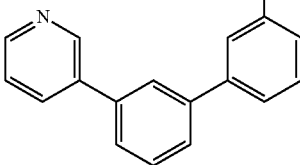
-continued
22-5
22-6
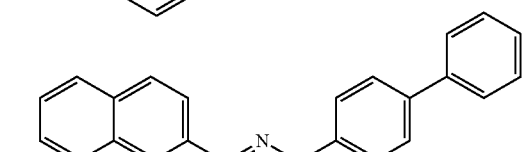
22-7
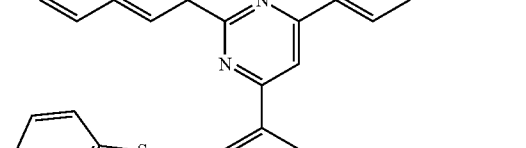
22-8
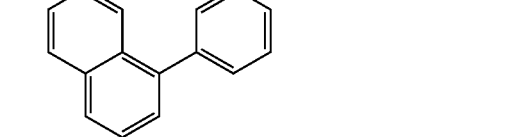

22-9
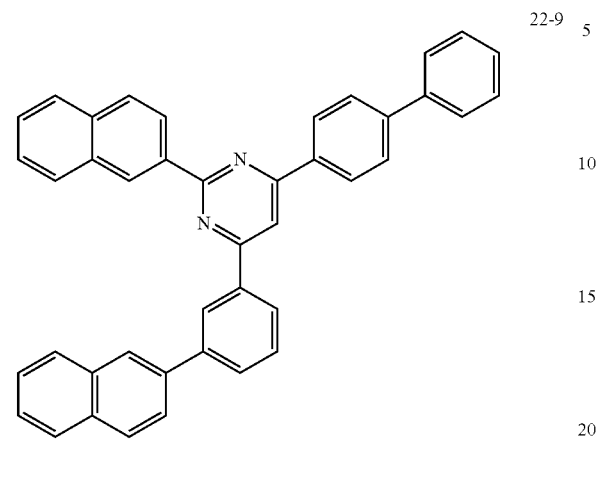
23-2
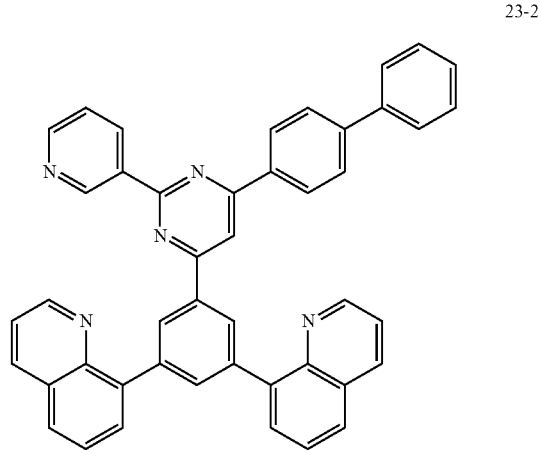
22-10
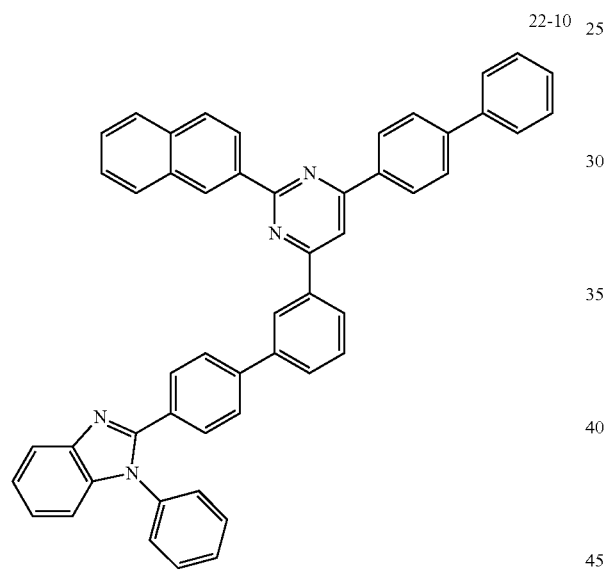
23-3
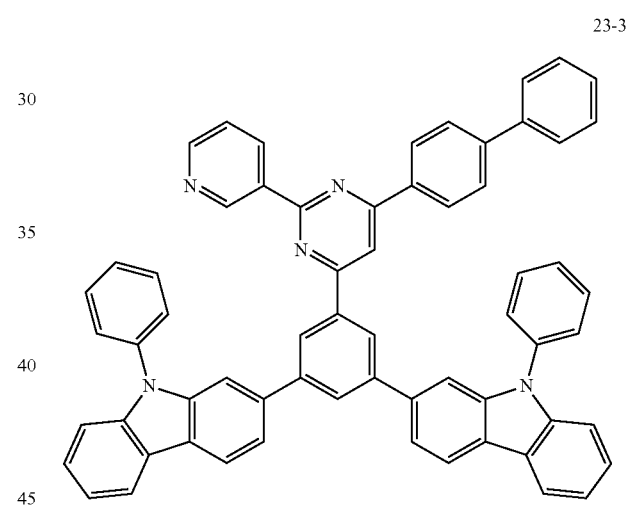
23-1
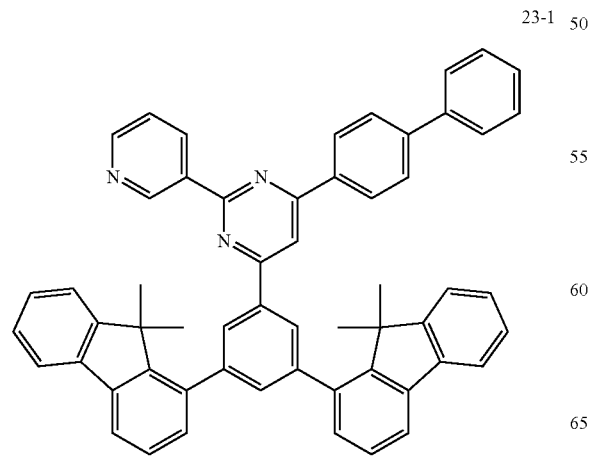
23-4
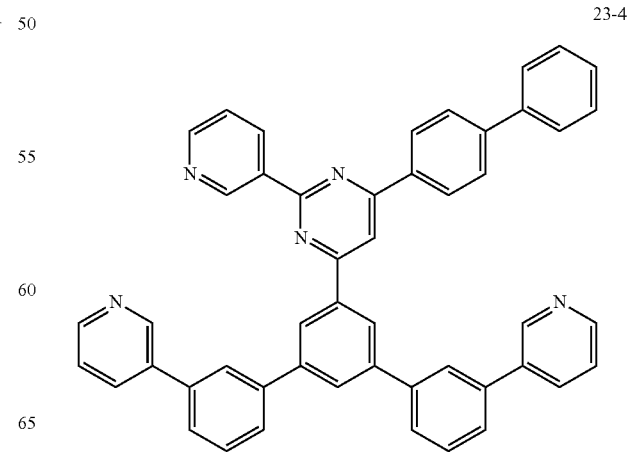

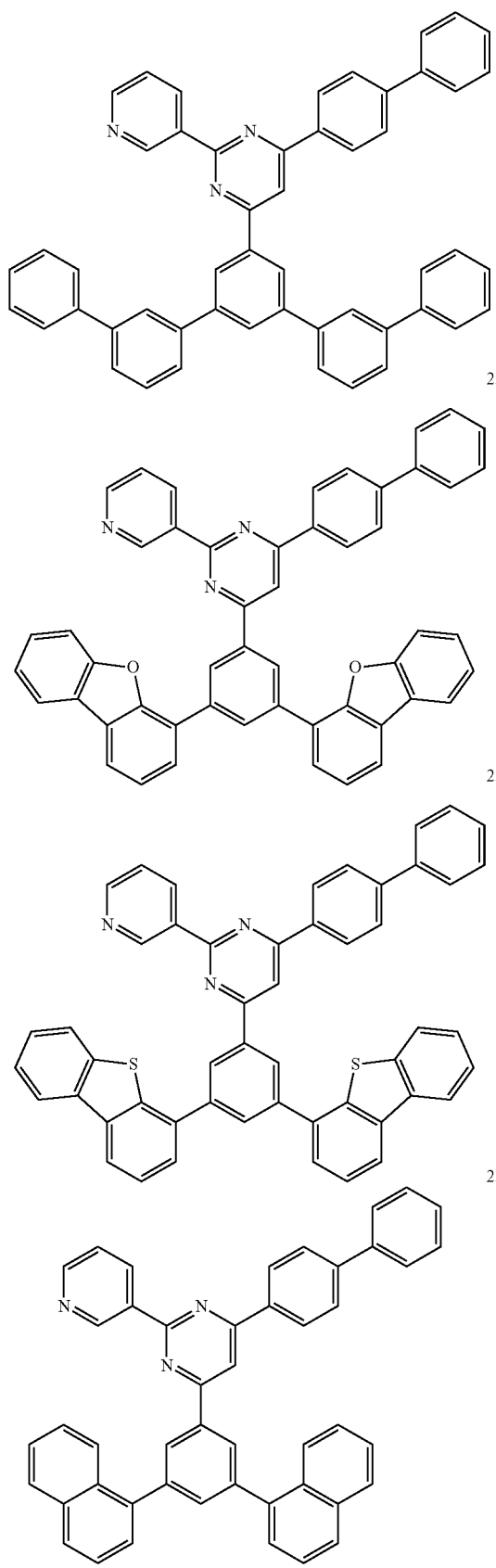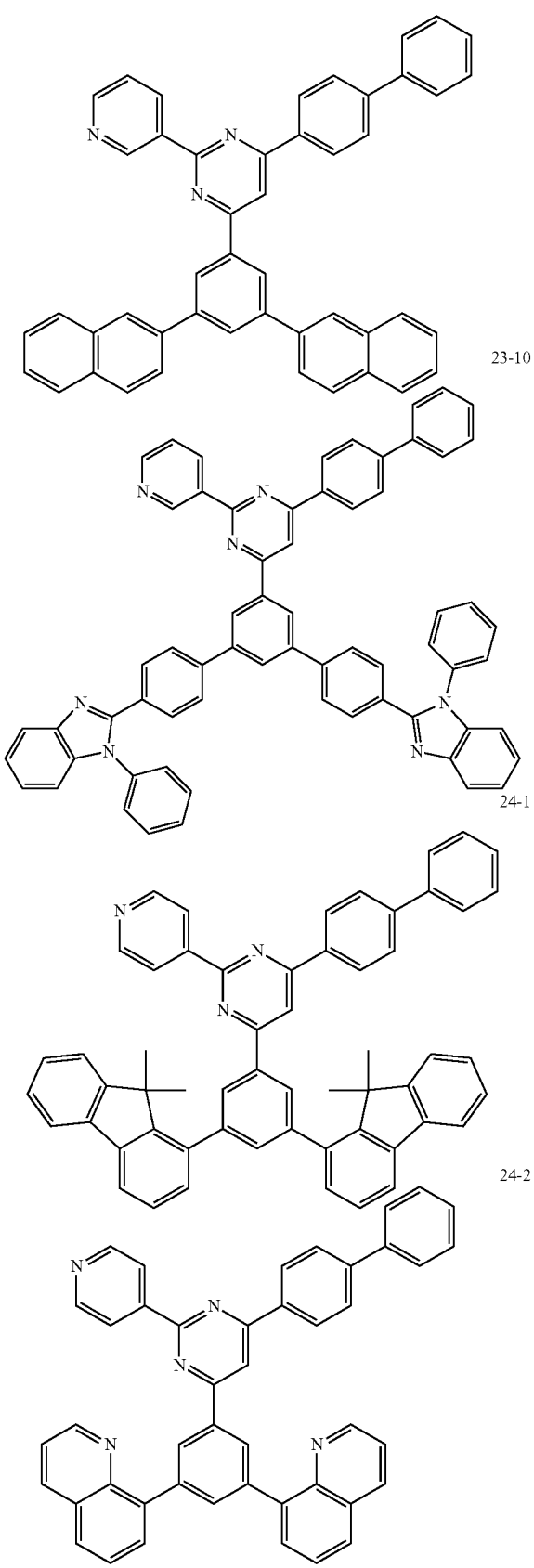

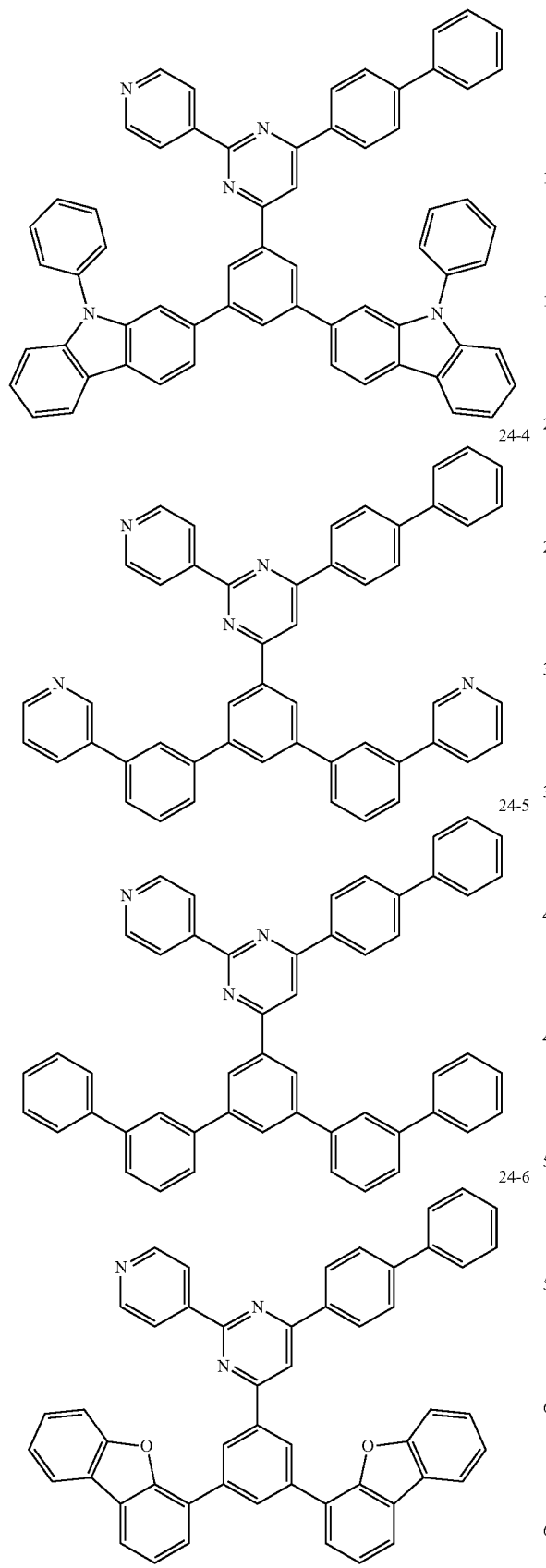
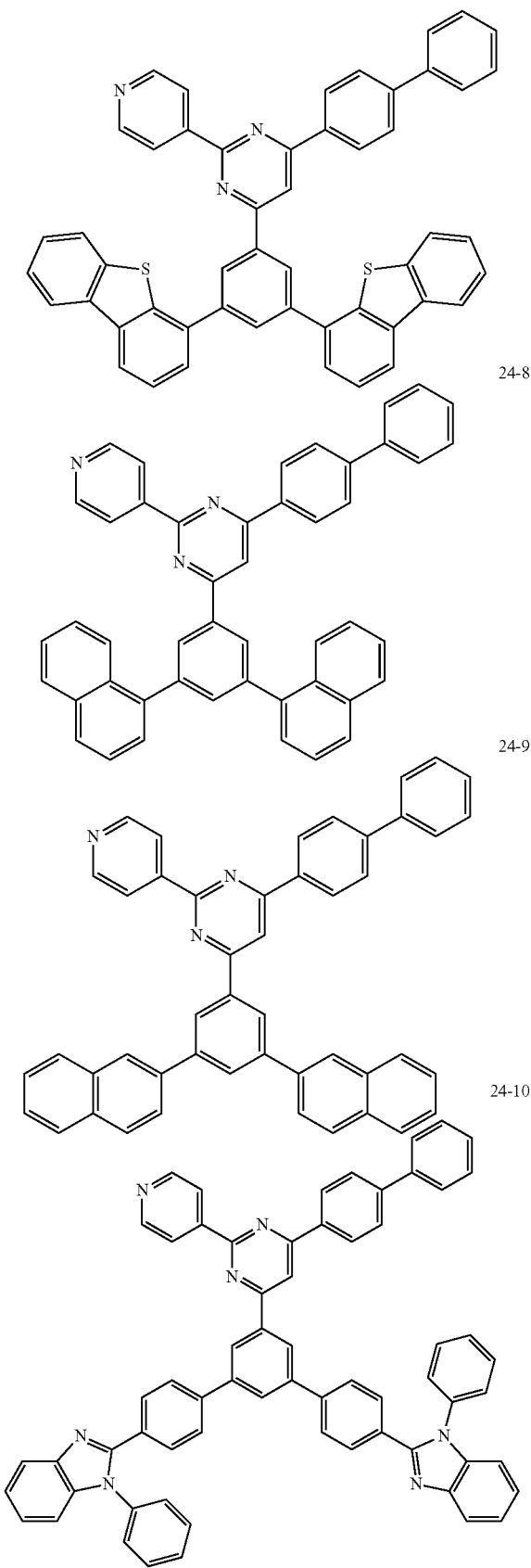

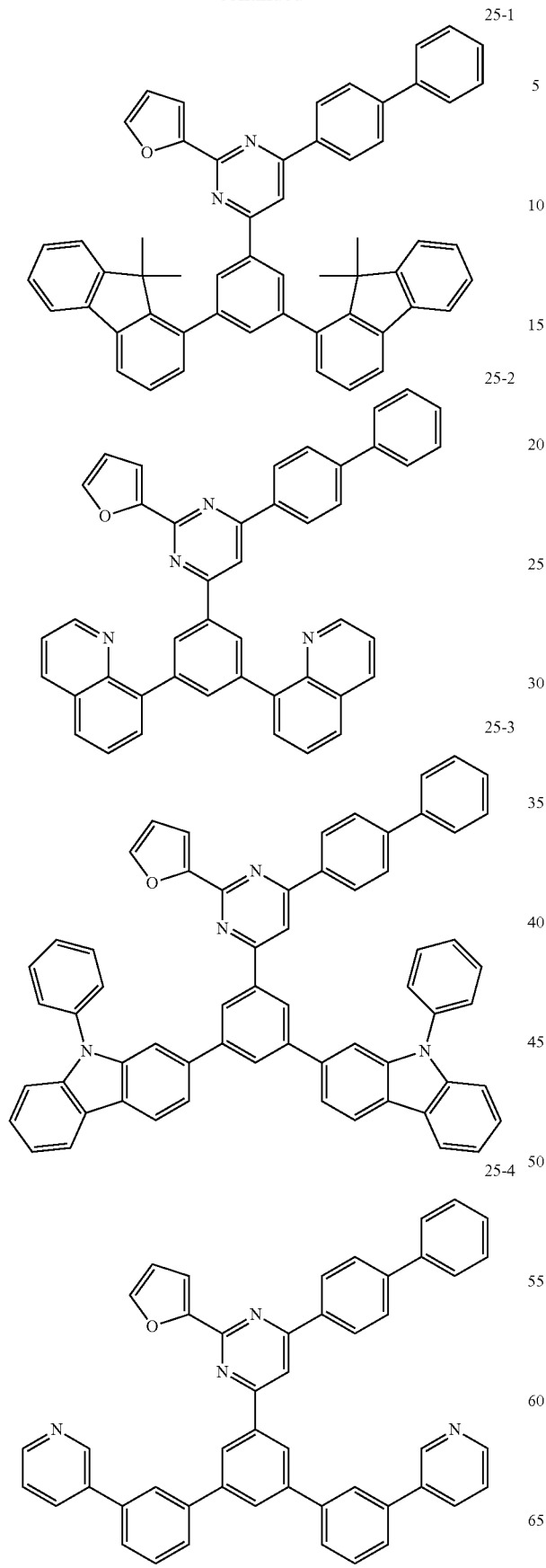
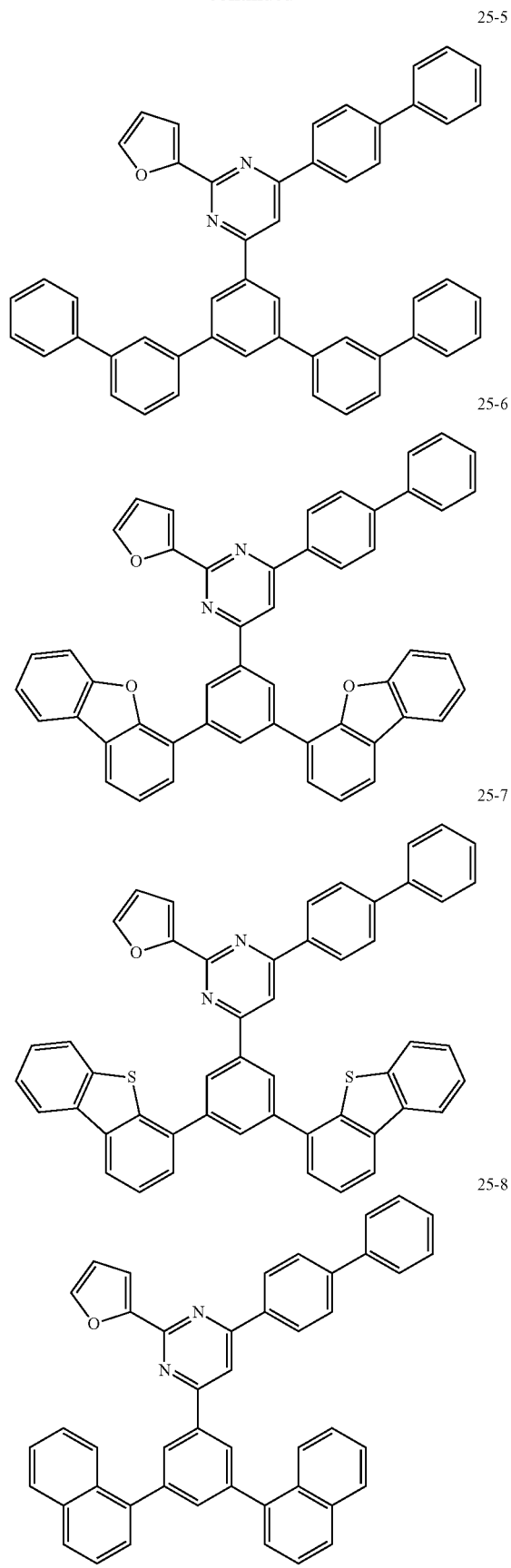

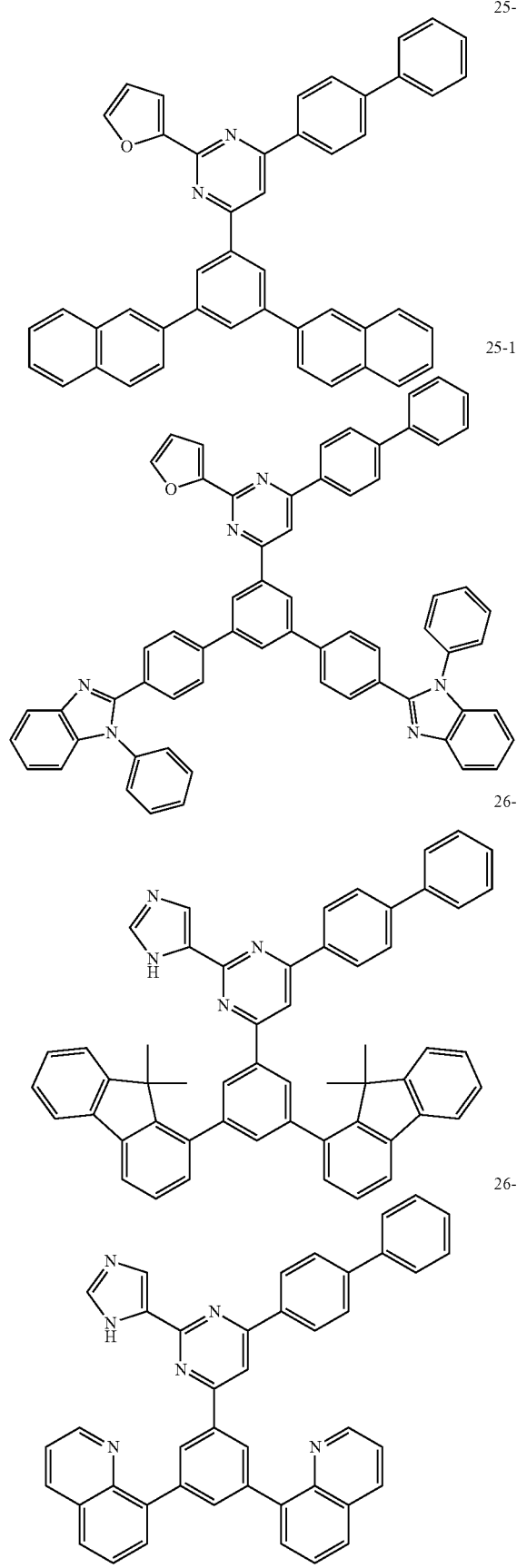
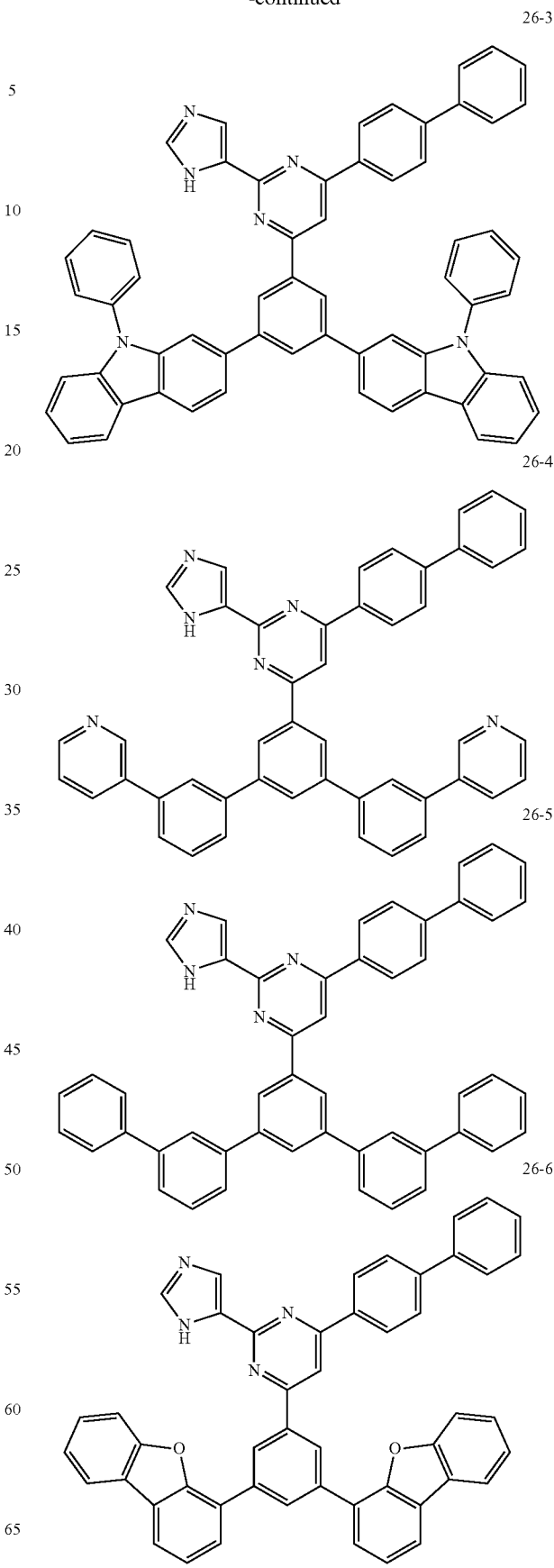

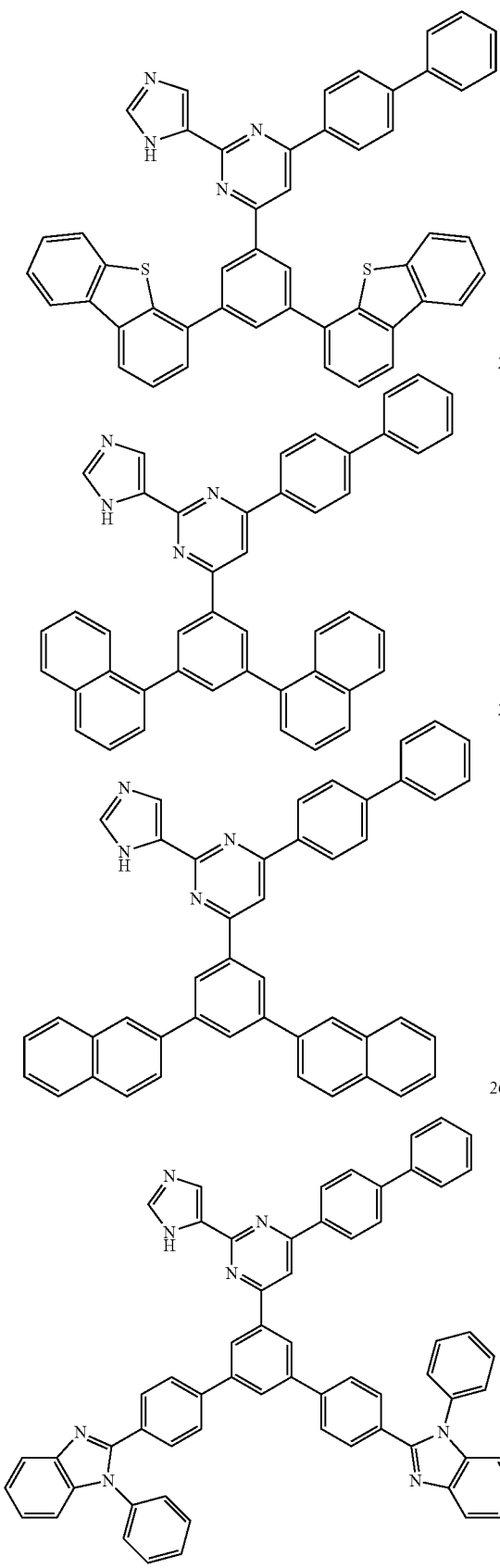
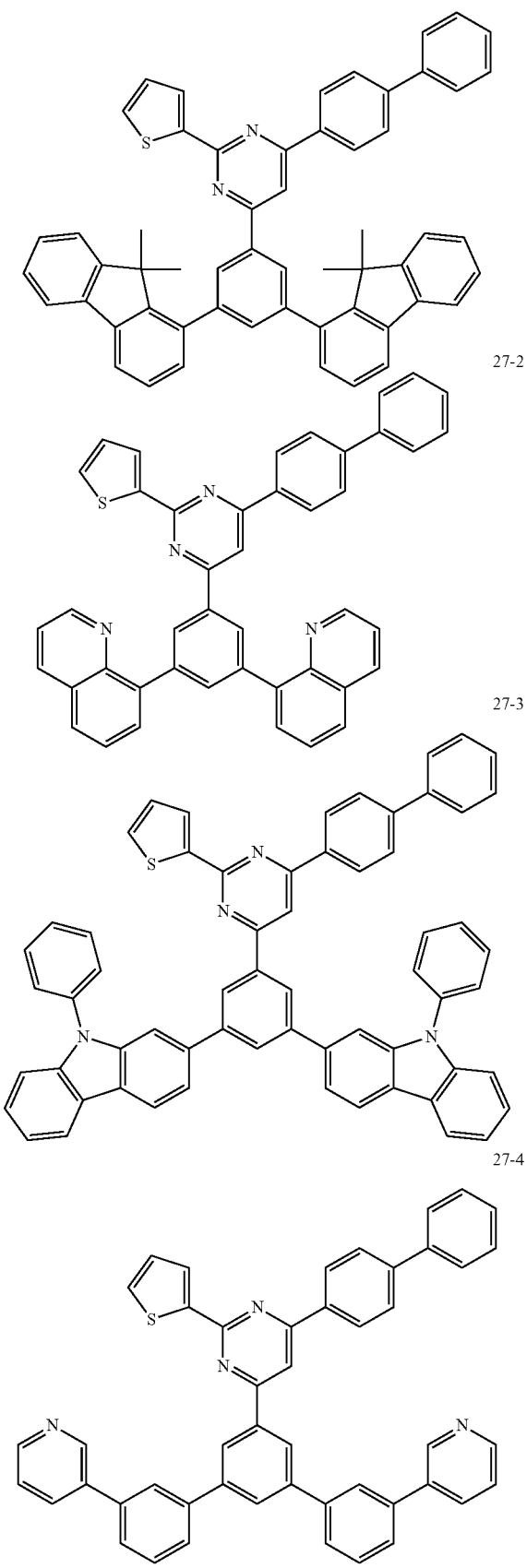

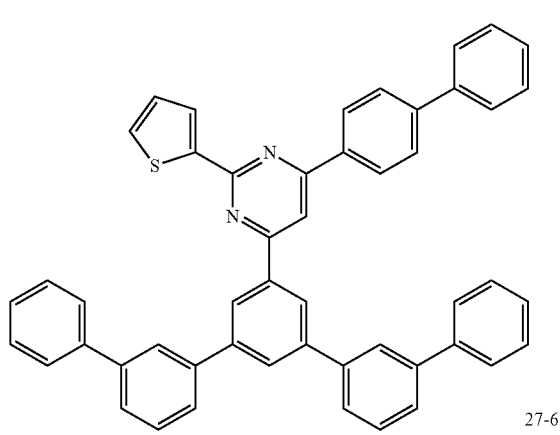
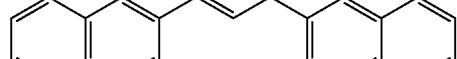
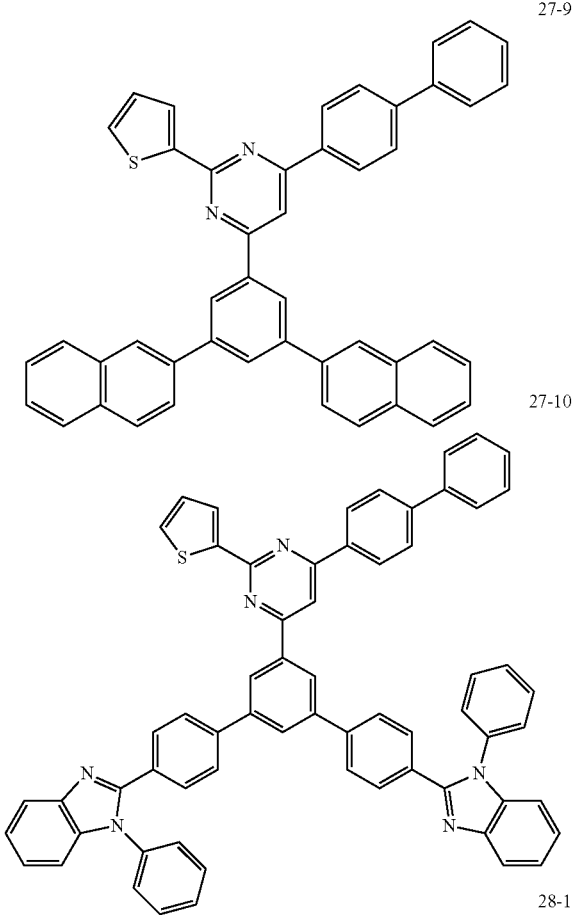
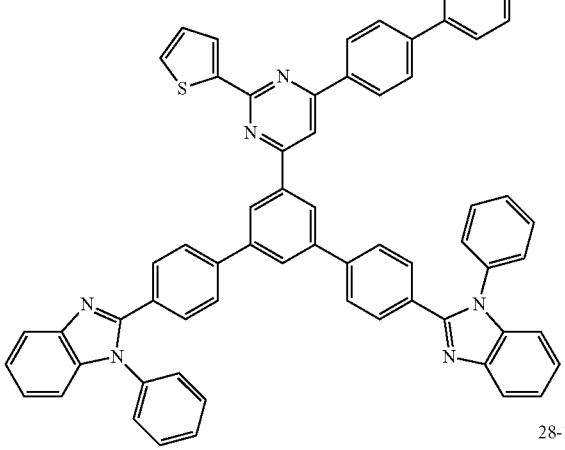
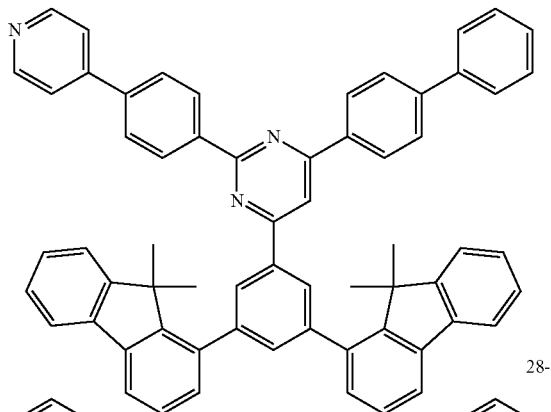
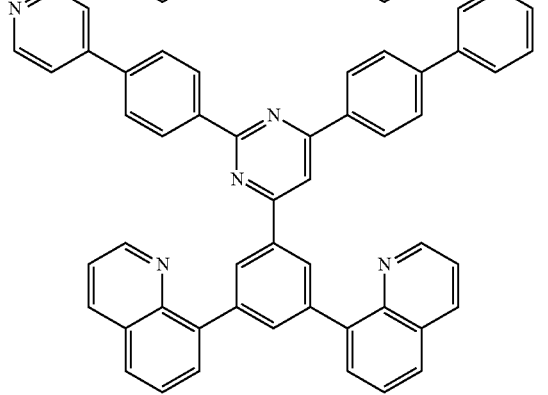

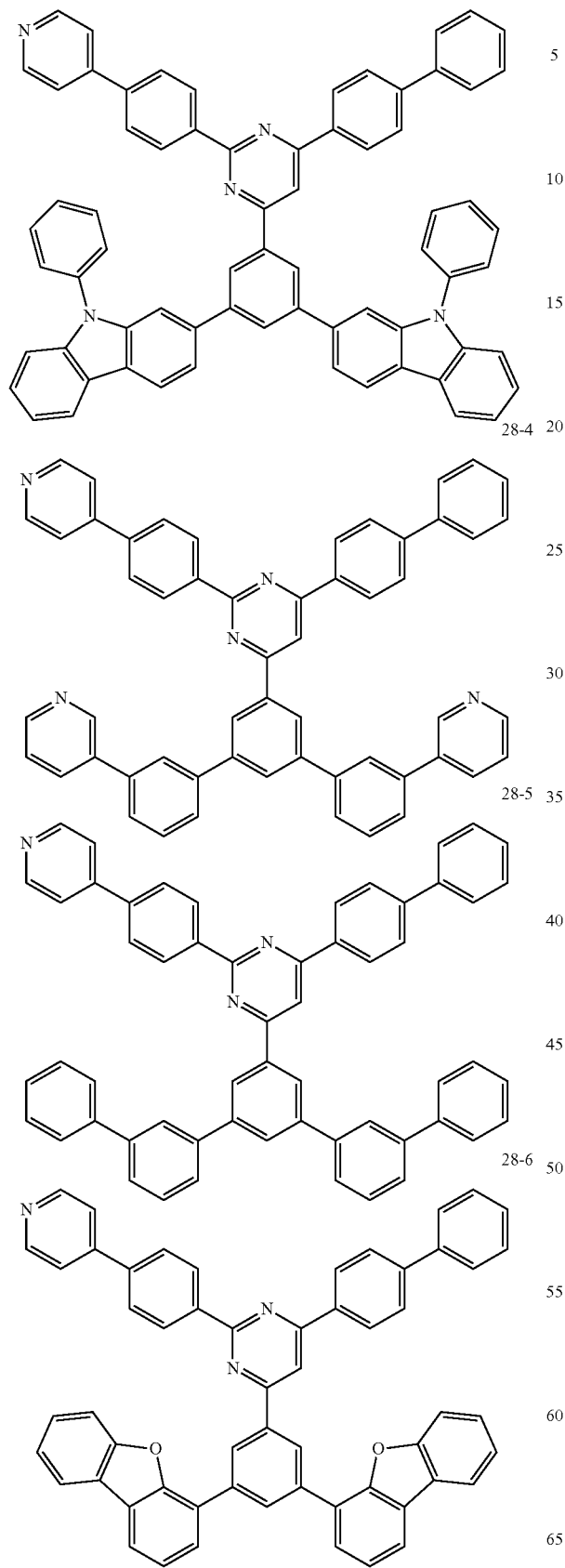
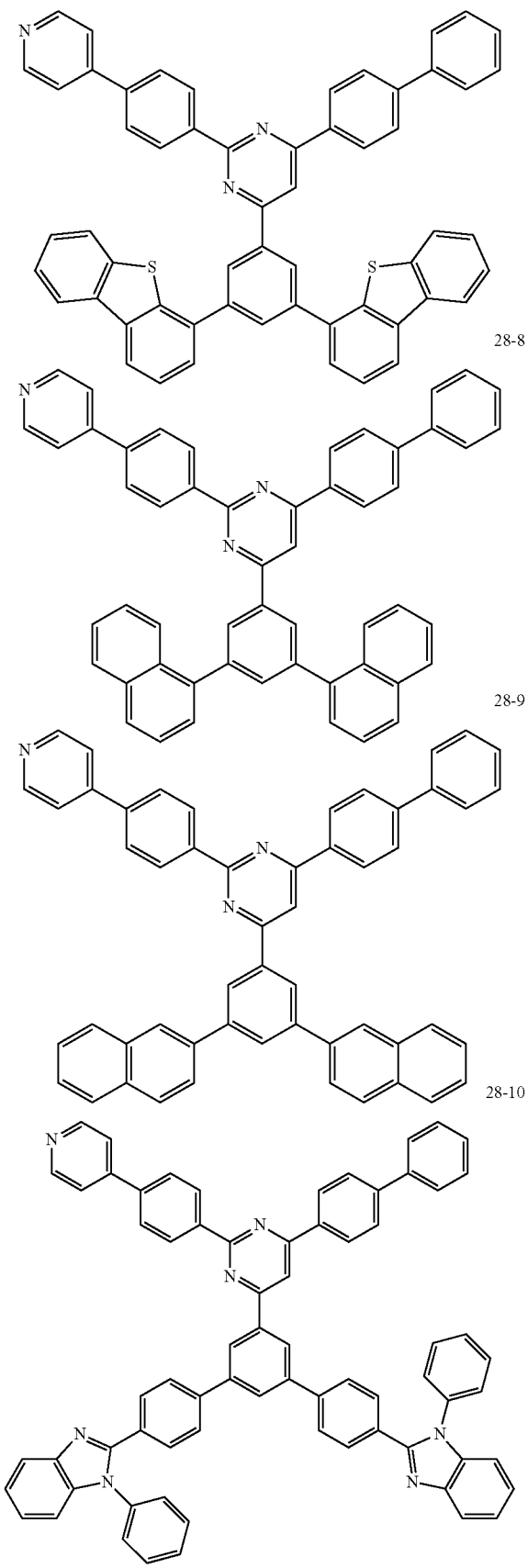

-continued
29-1
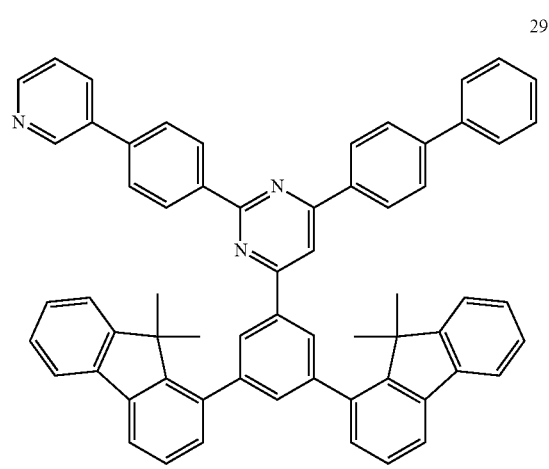
29-2
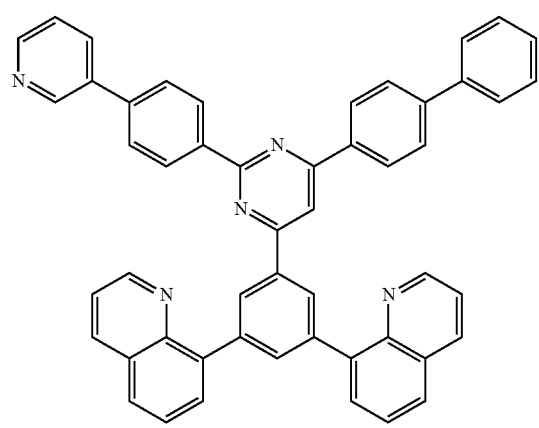
29-3
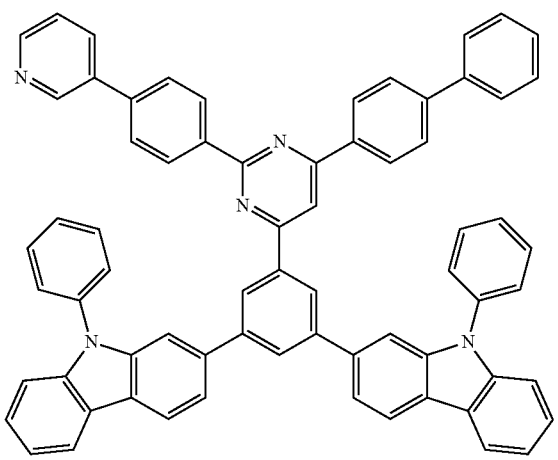
-continued
29-4
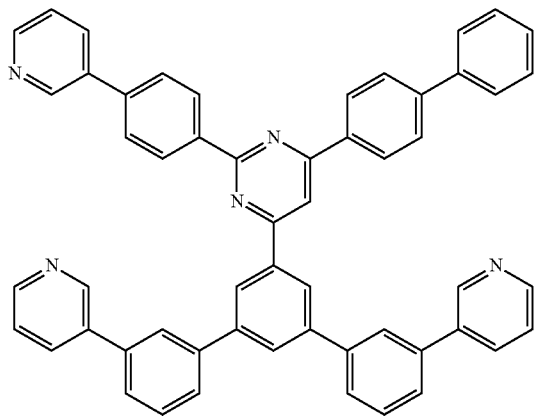
29-5
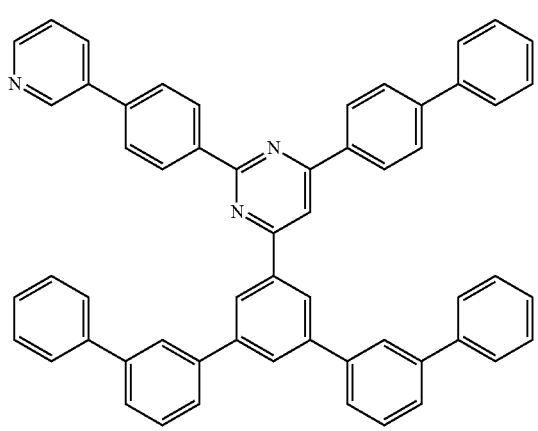
29-6
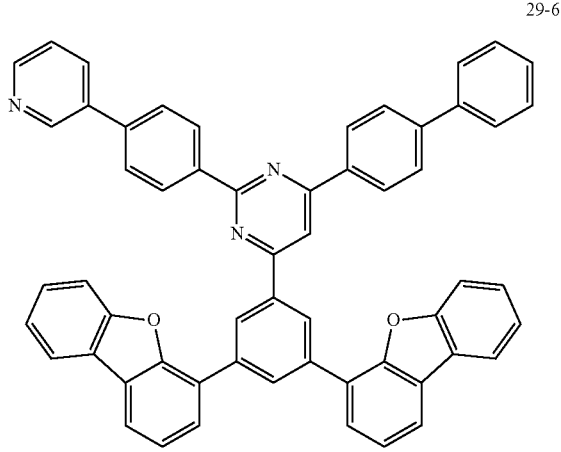

29-7
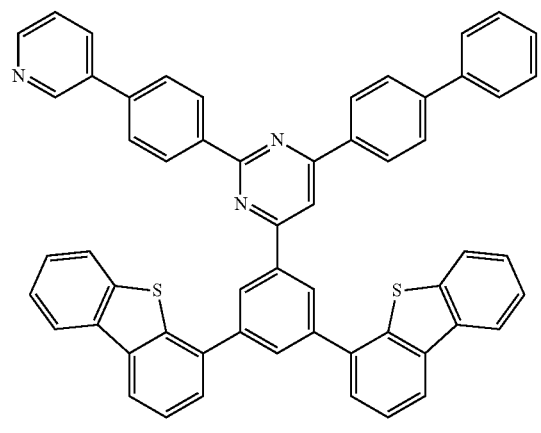
29-8
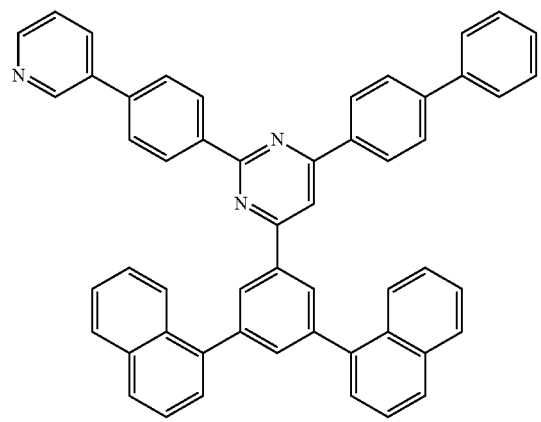
29-9
29-10
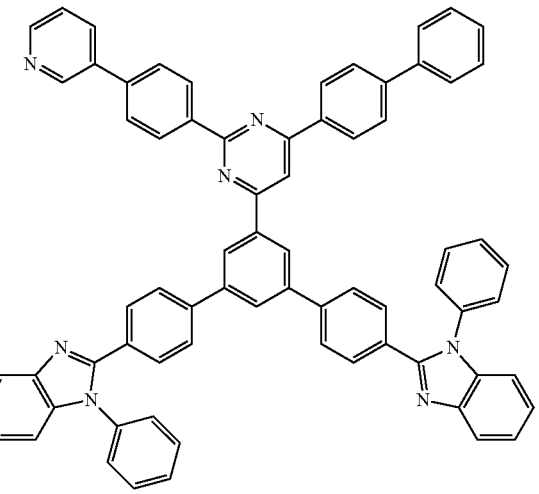
30-1
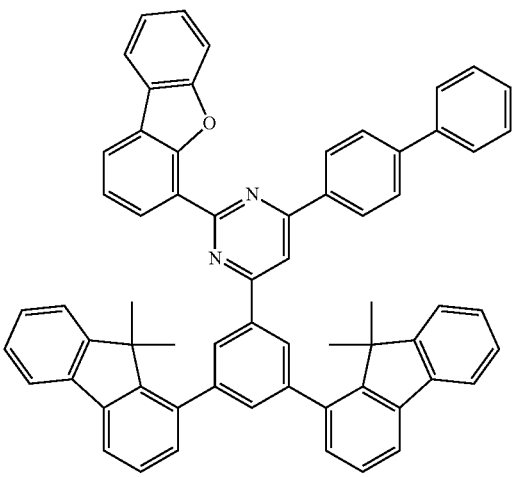
30-2
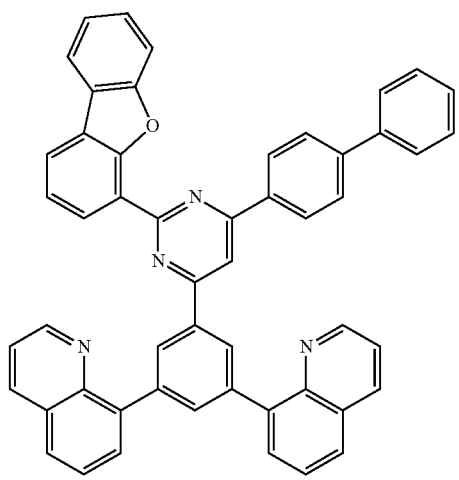

30-3
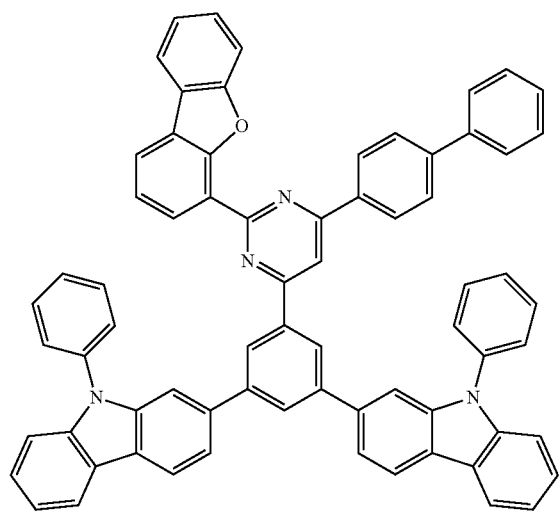
30-4
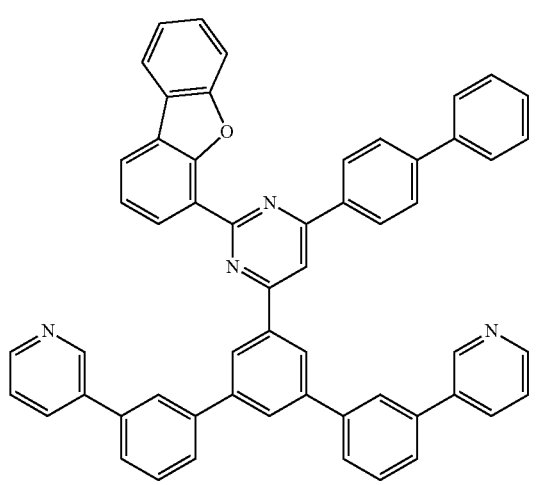
30-5
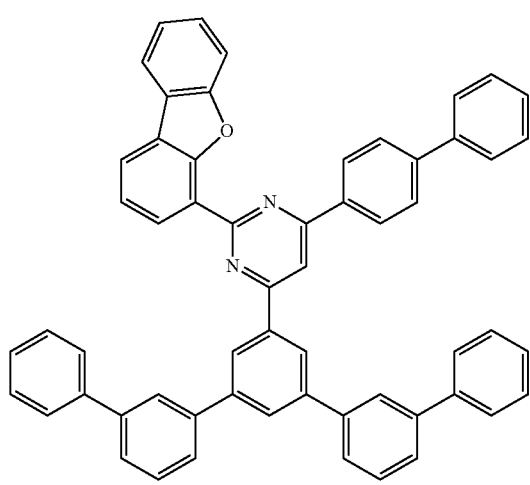
30-6
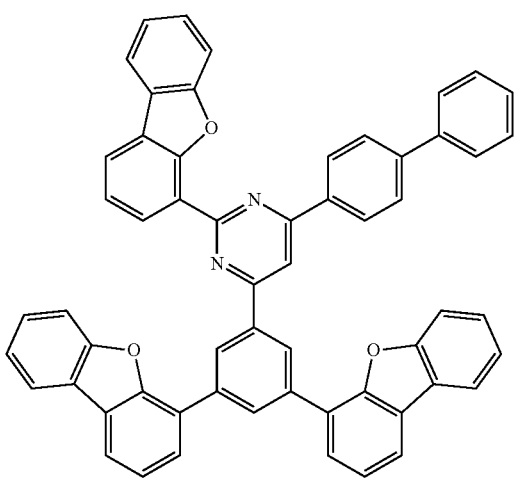
30-7
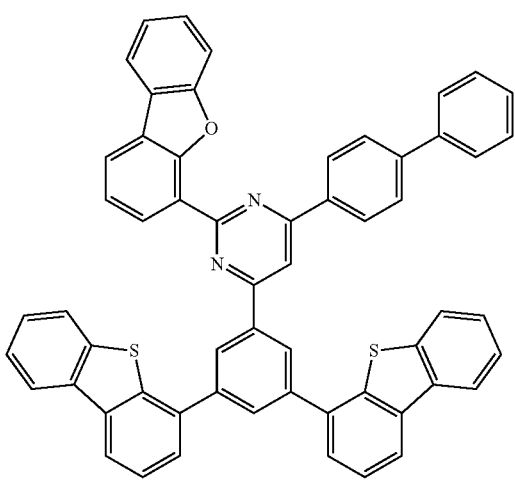
30-8
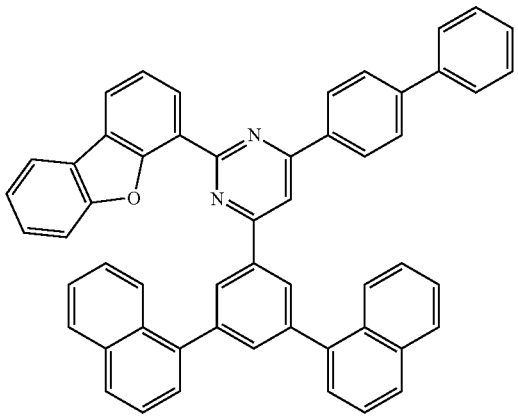

-continued
30-9
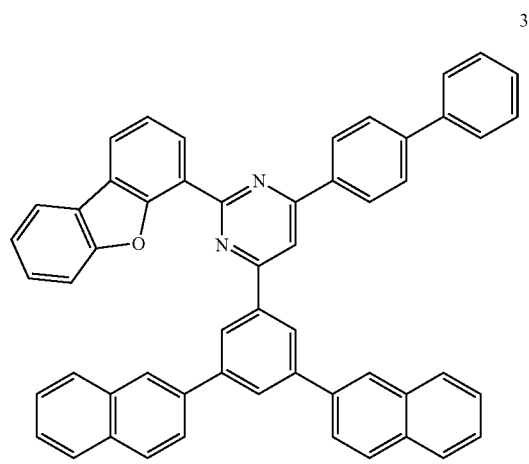
30-10
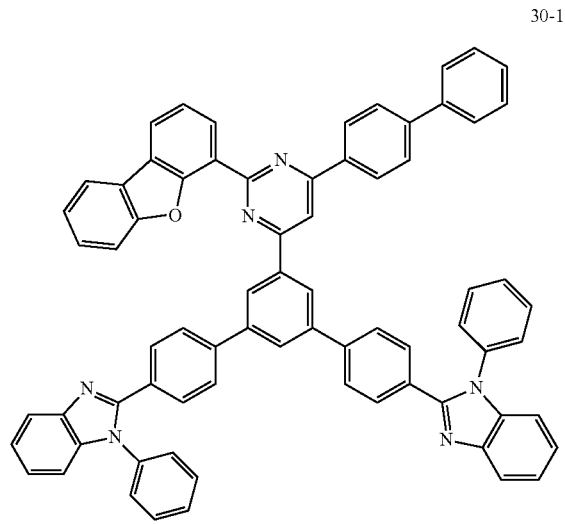
31-1
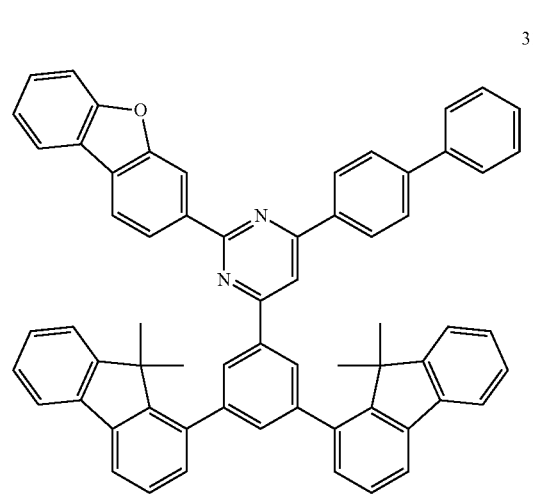
-continued
31-2
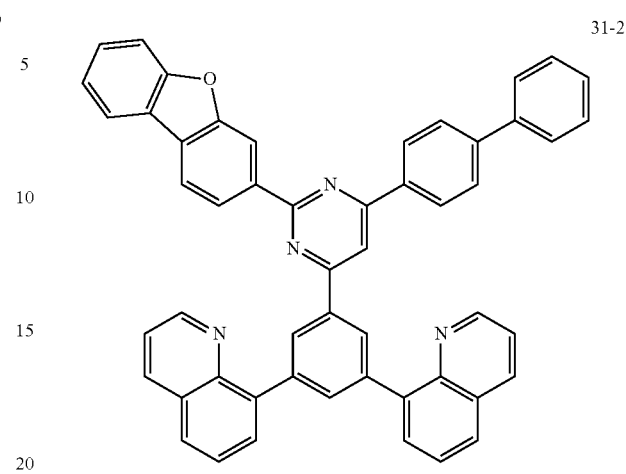
31-3
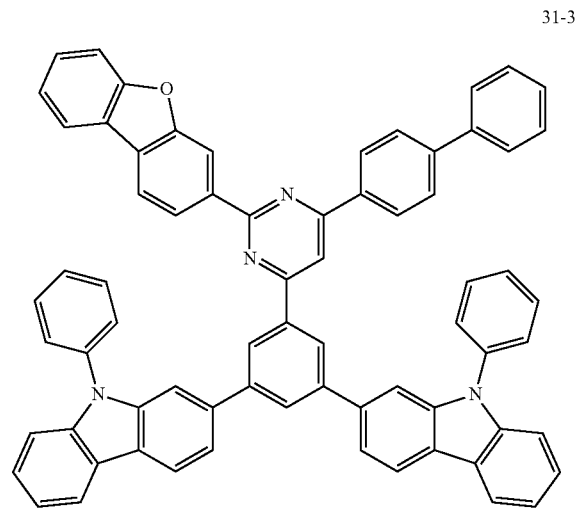
31-4
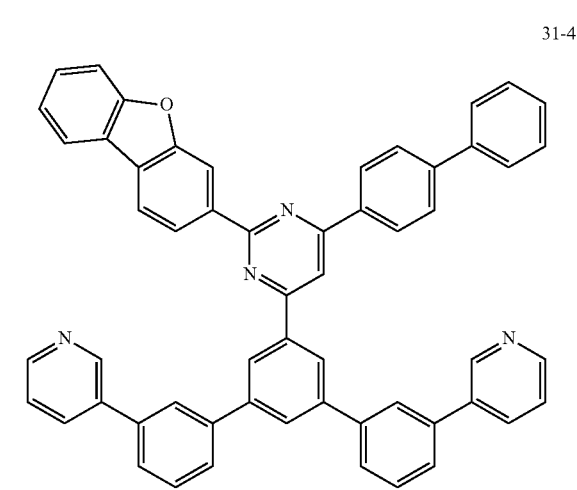

31-5
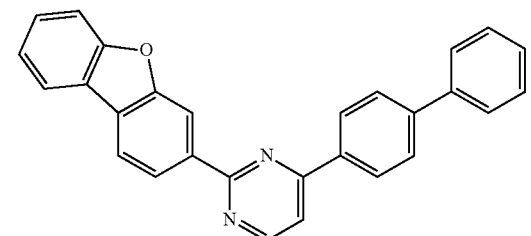
31-6
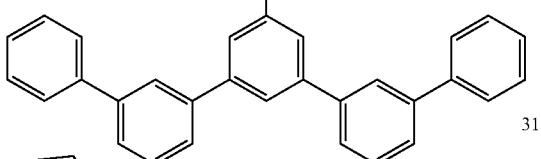
31-7
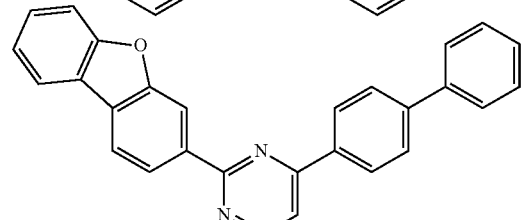
31-8
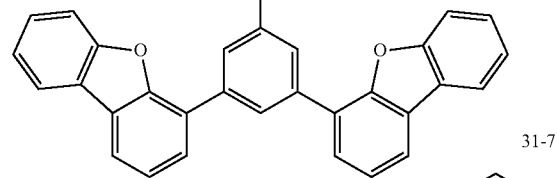
31-9
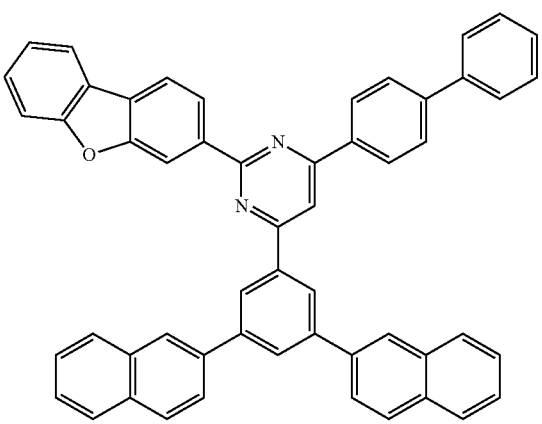
31-10
32-1
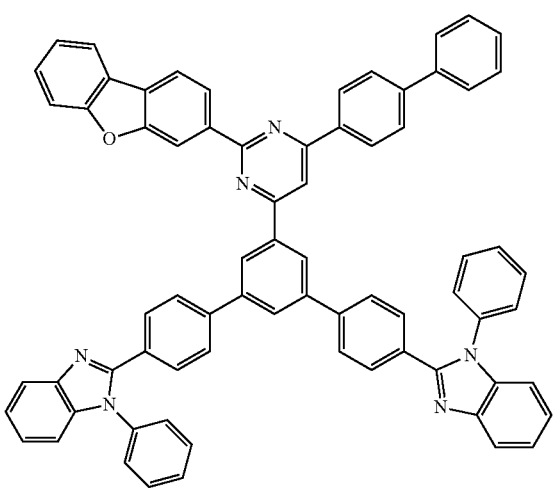

-continued
32-2
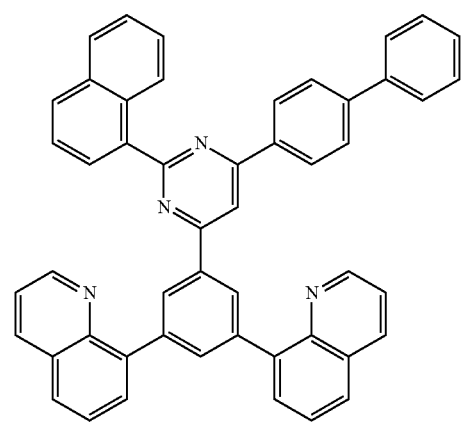
32-5
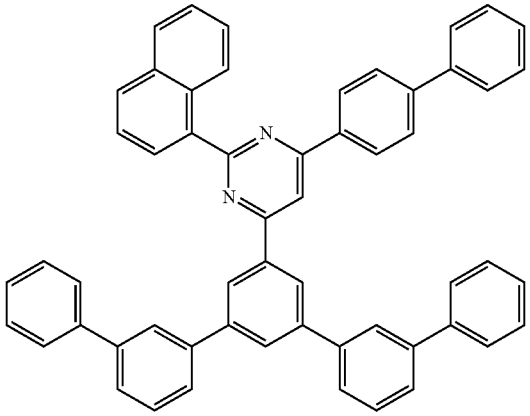
32-3
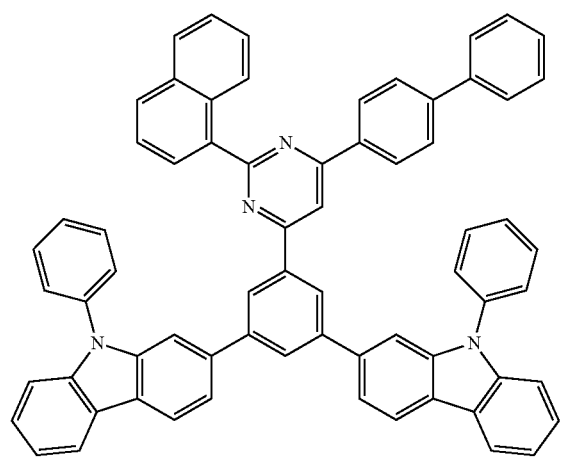
32-6
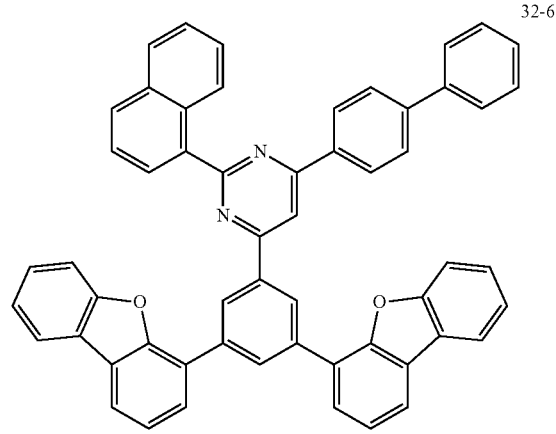
32-4
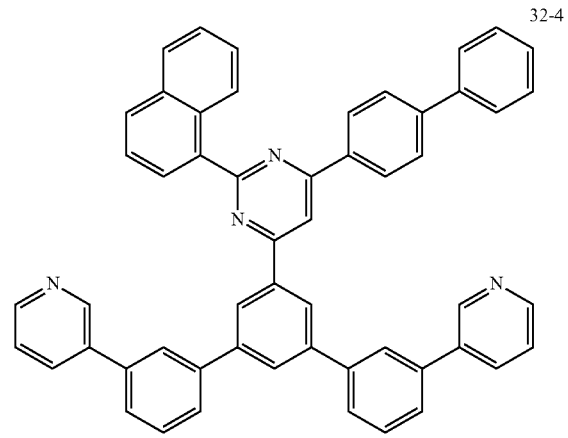
32-7
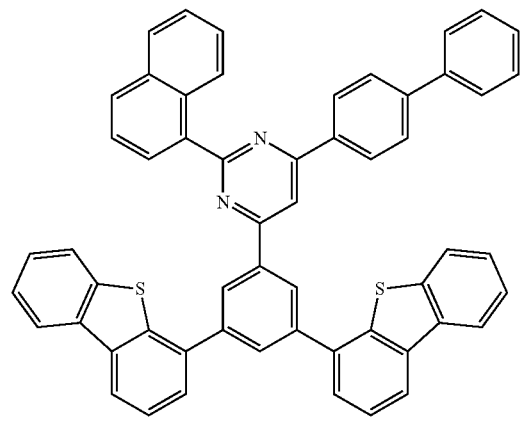

32-8
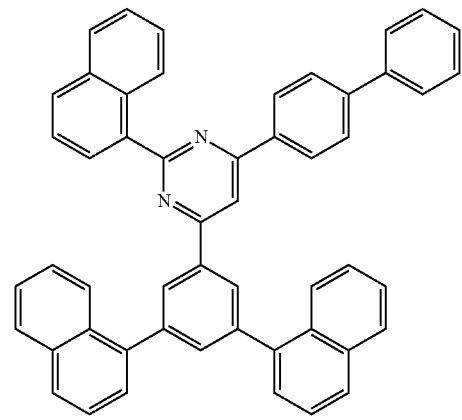
32-9
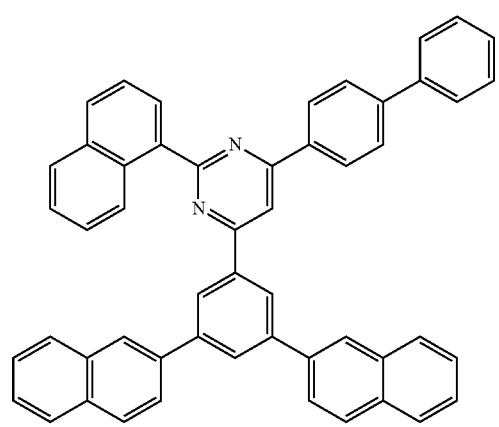
32-10
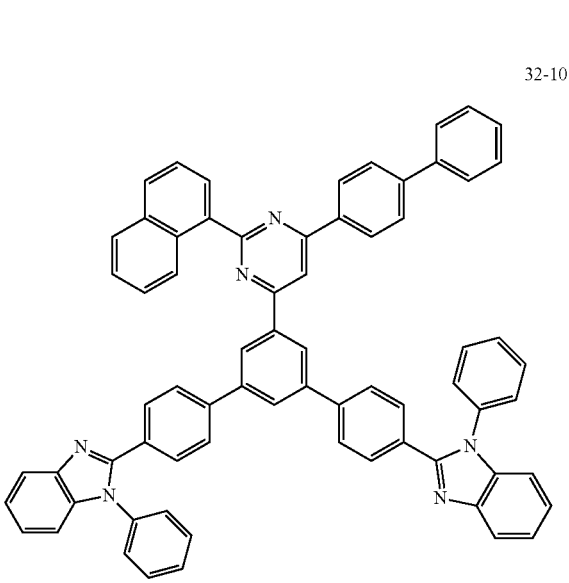 [SMILES: c1ccc(-c2ccc(-c3cc(-c4cc(-c5ccc(-c6nc7ccccc7n6-c6ccccc6)cc5)cc(-c5ccc(-c6nc7ccccc7n6-c6ccccc6)cc5)c4)nc(-c4cccc5ccccc45)n3)cc2)cc1]
33-1
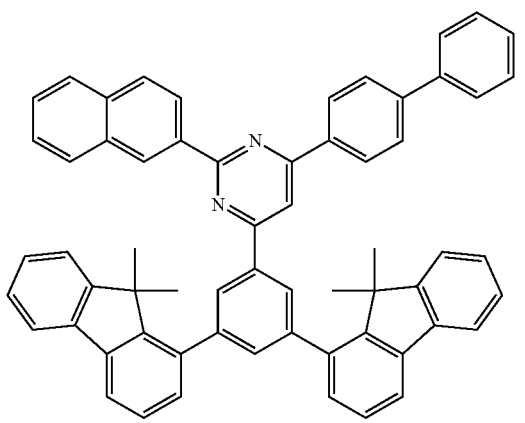
33-2
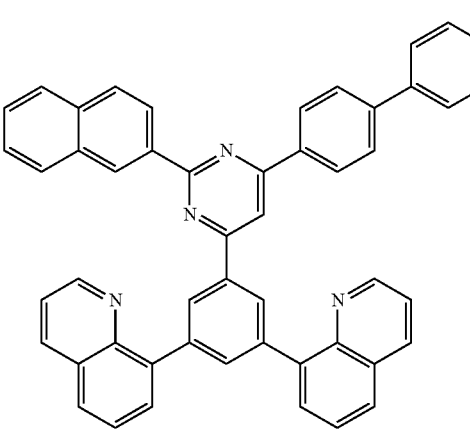
33-3
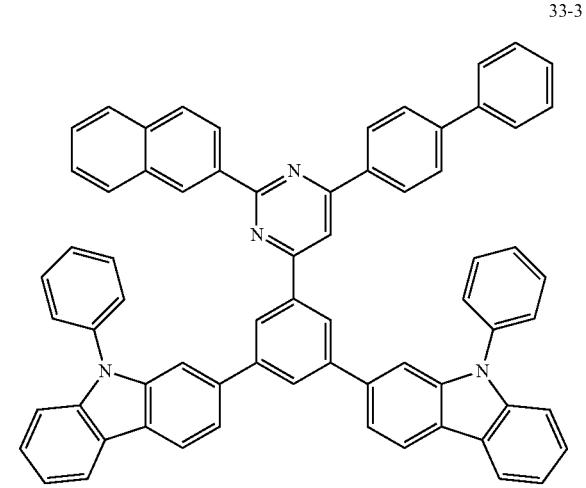

33-4
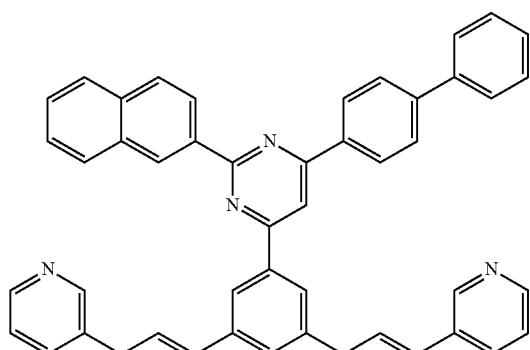
33-5
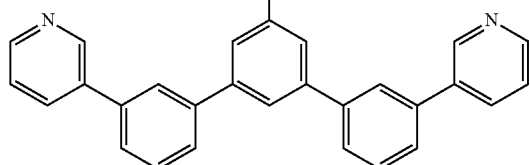
33-6
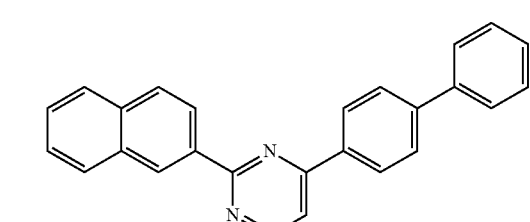
33-7
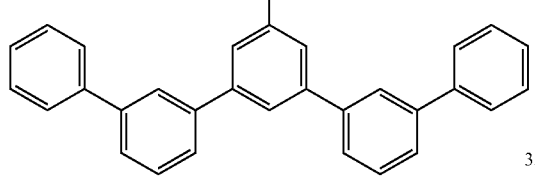
33-8
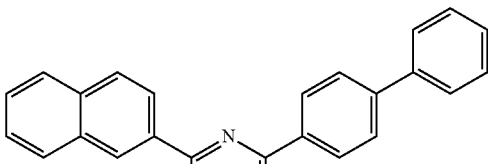
33-9
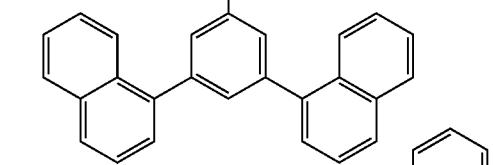
33-10
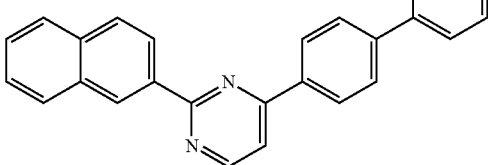
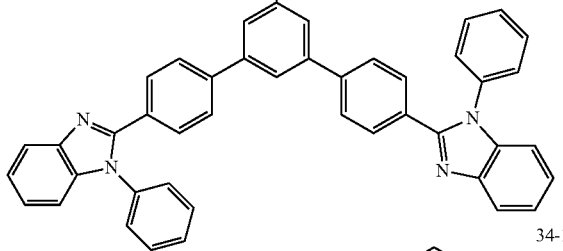
34-1
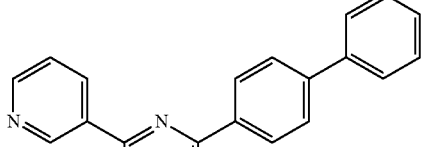
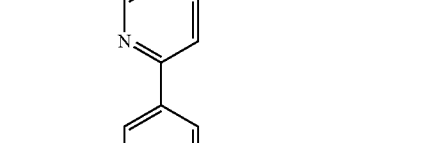
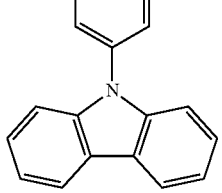

34-2
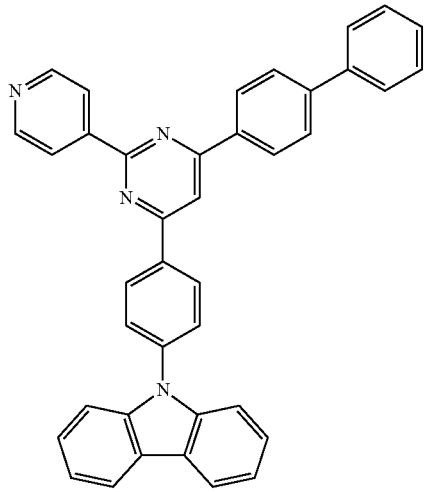
34-3
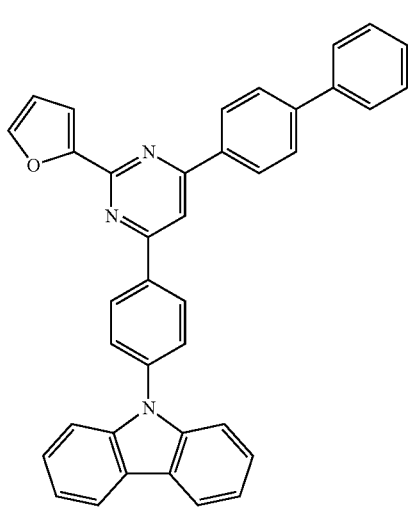
34-4
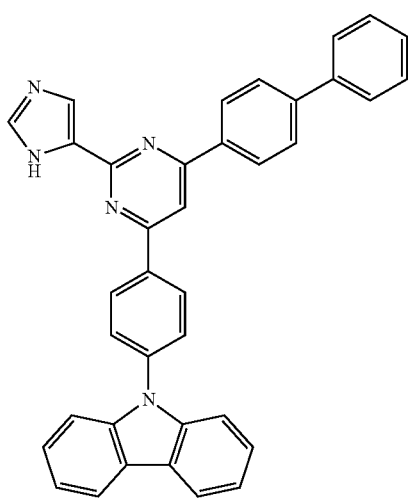
34-5
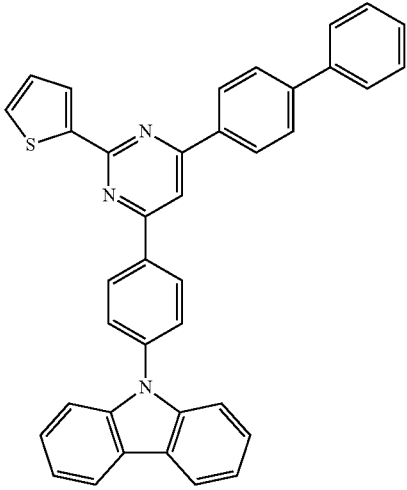
34-6
34-7

34-8
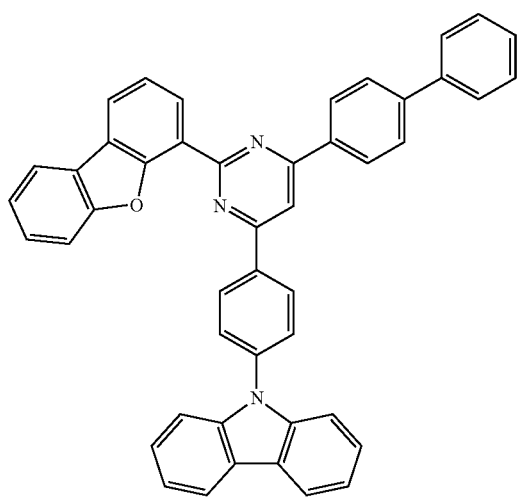
34-9
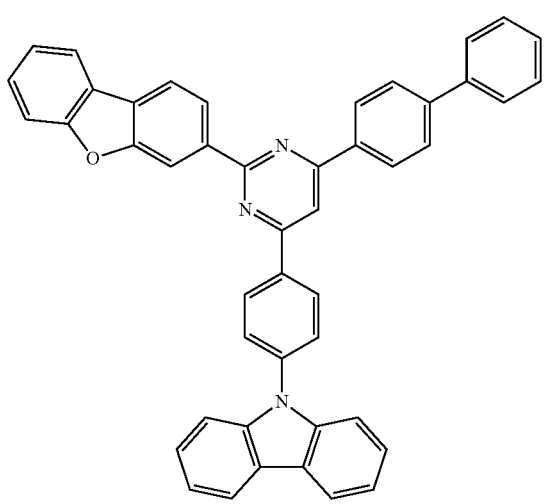
34-10
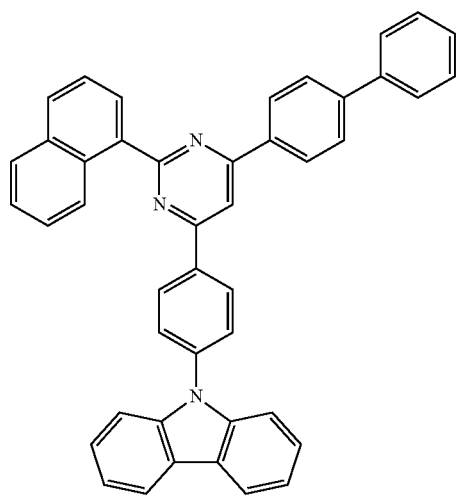
34-11
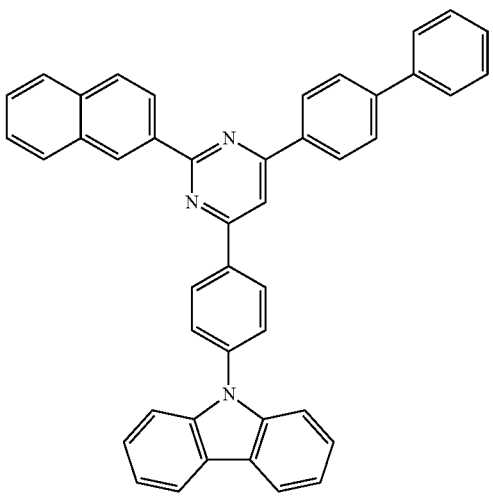
35-1
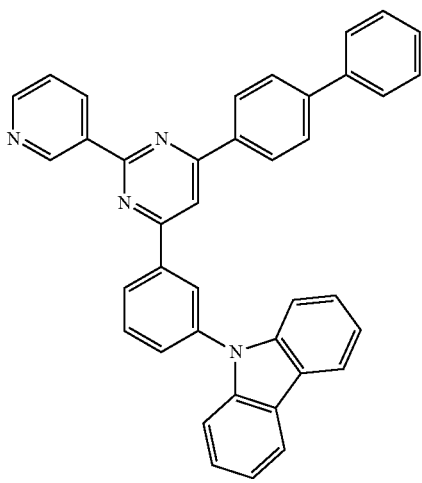
35-2
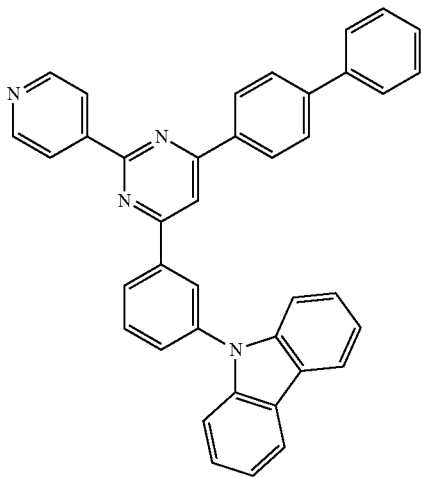

35-3
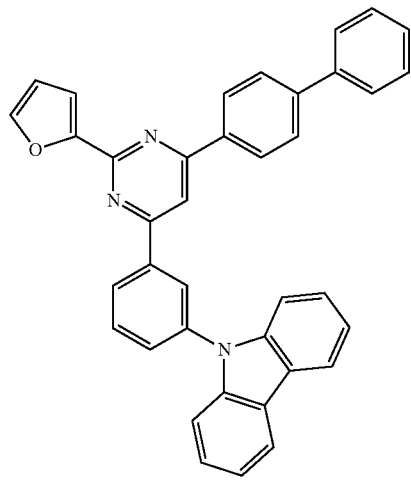
35-4
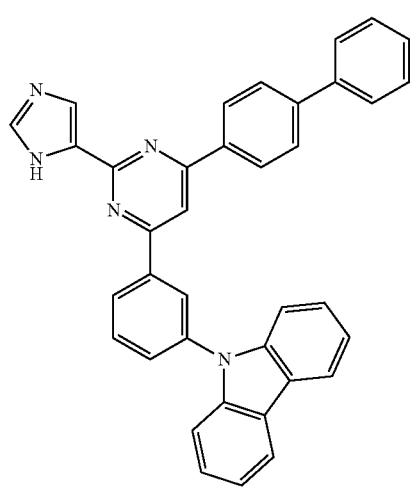
35-5
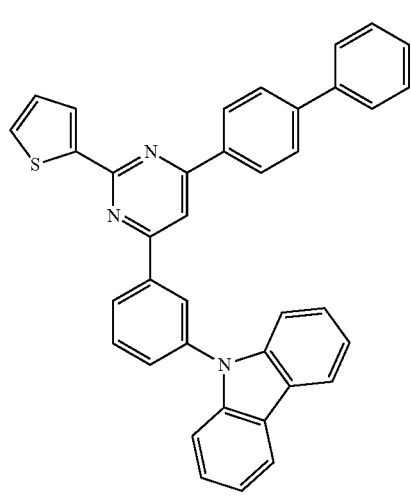
35-6
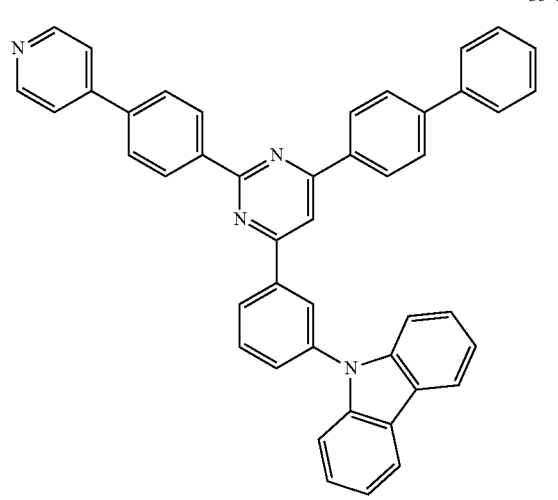
35-7
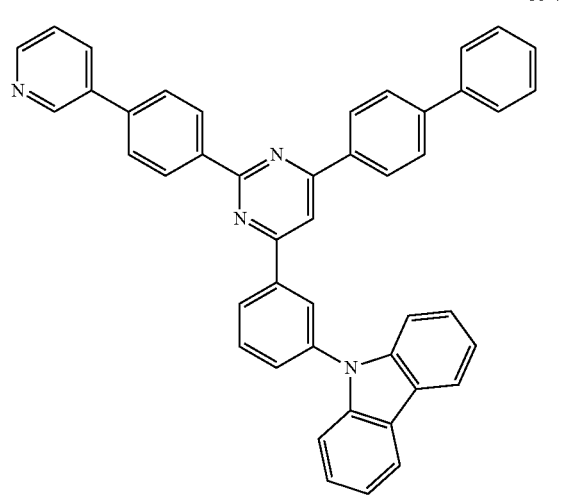
35-8
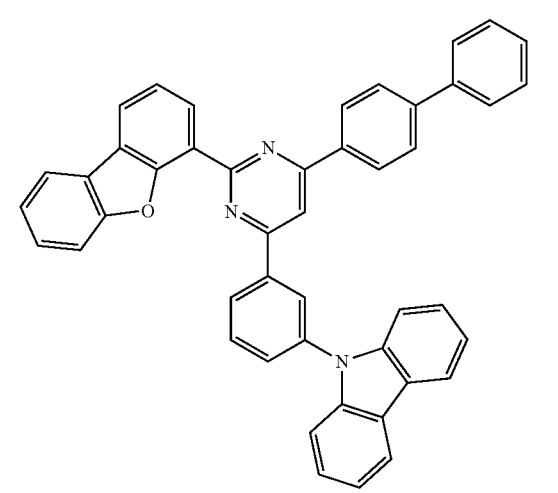

35-9
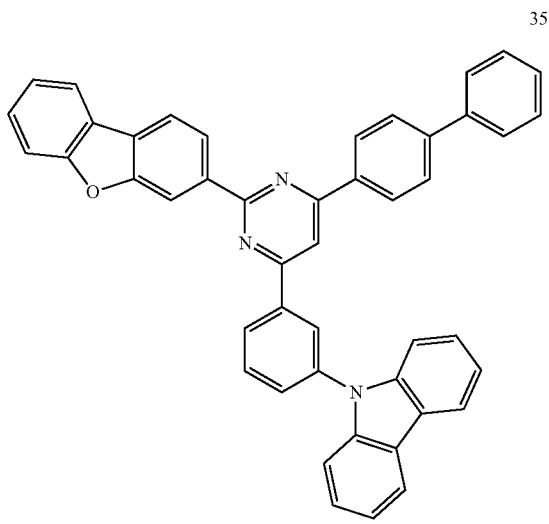
35-10
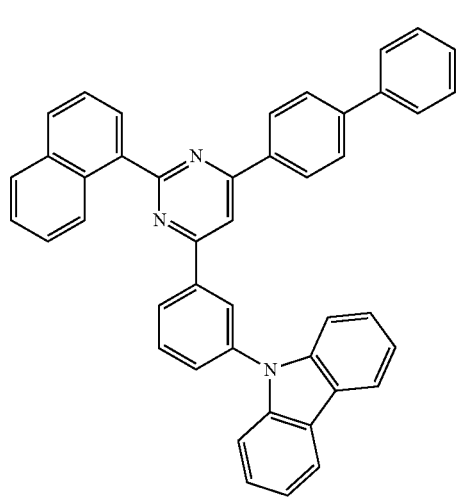
35-11
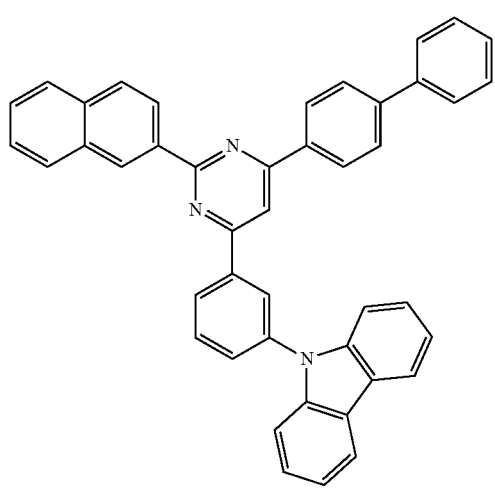
36-1
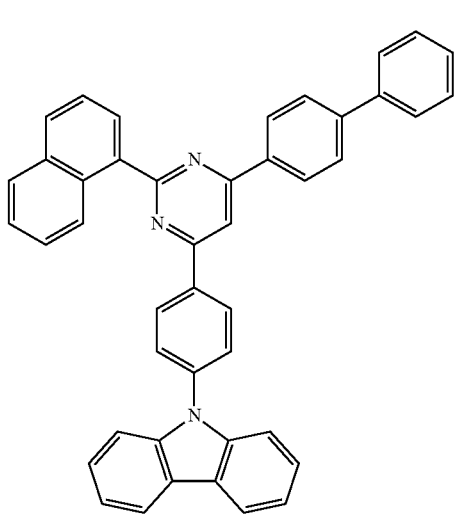
36-2
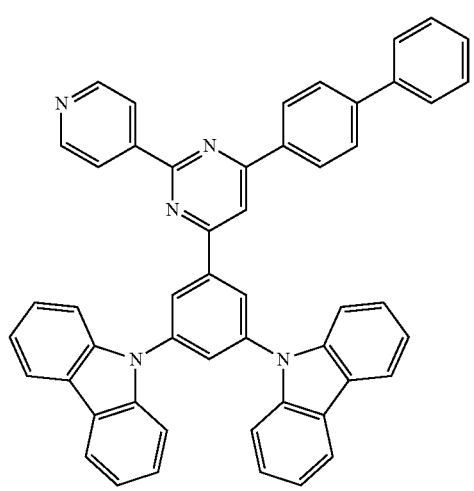
36-3
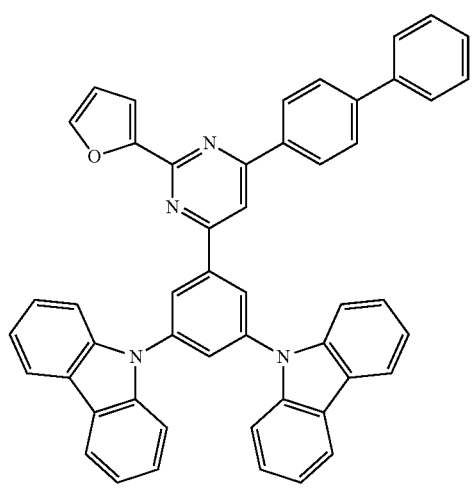

36-4
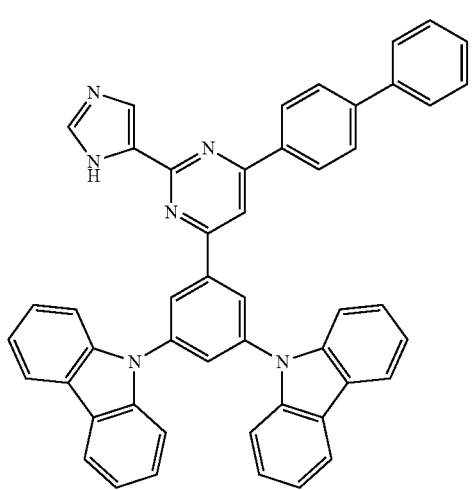
36-5
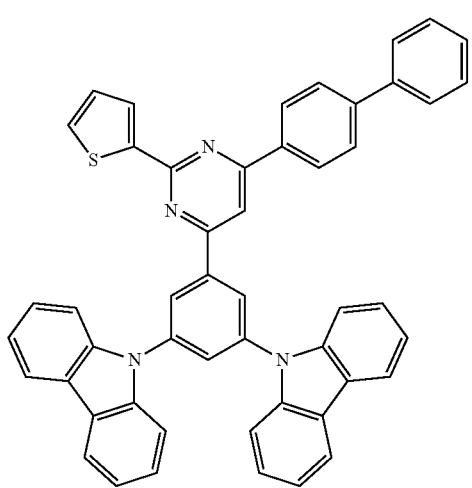
36-6
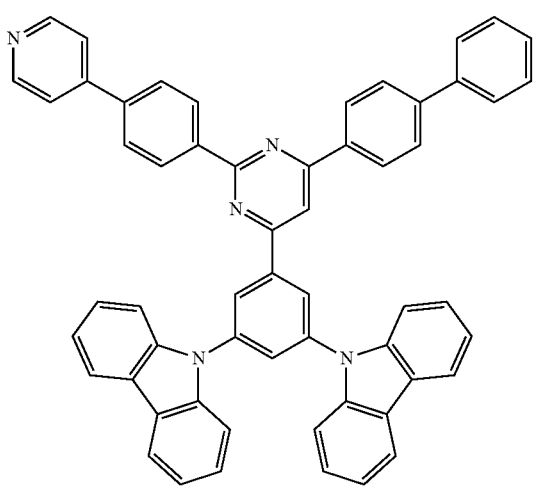
36-7
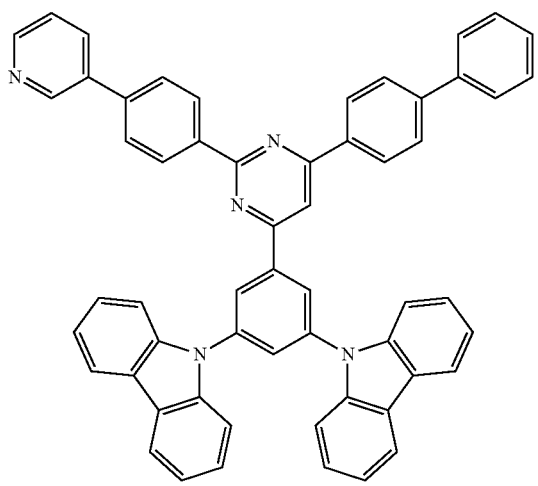
36-8
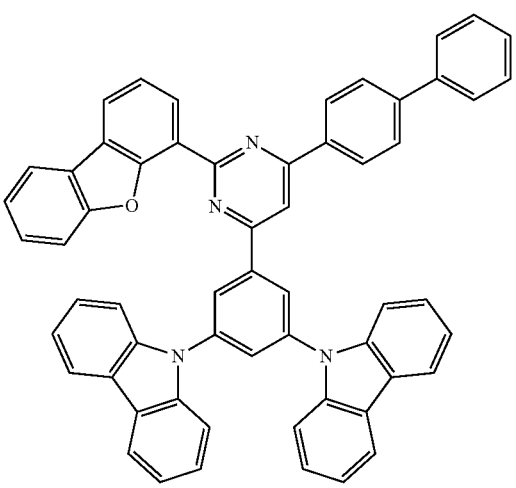
36-9
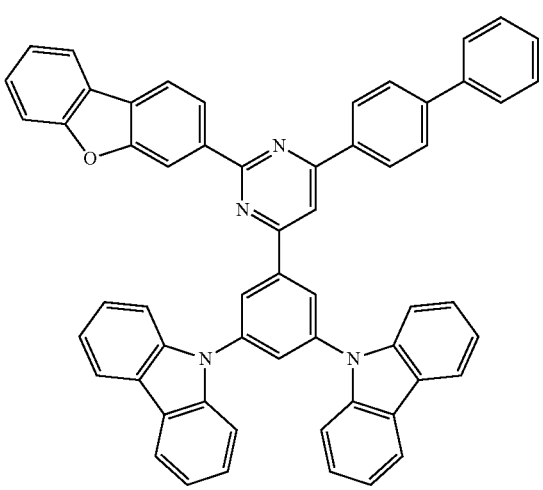

36-10

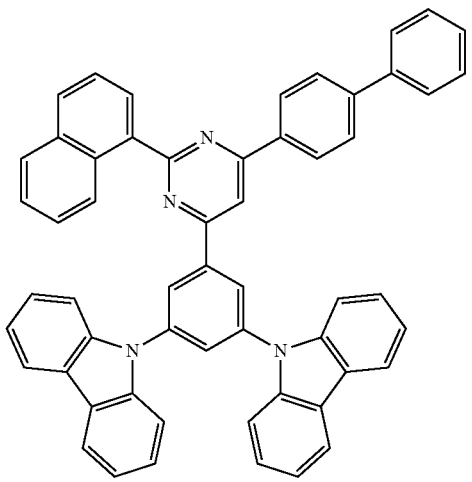

36-11

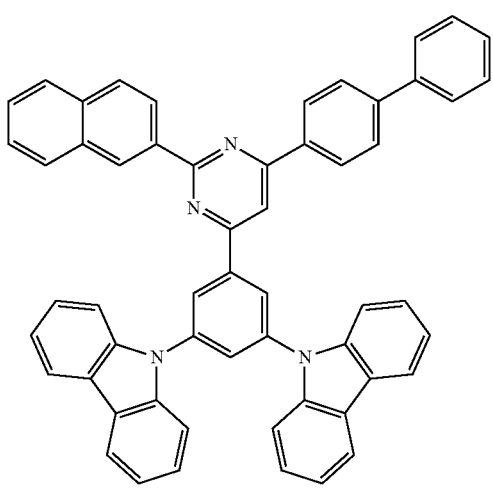

A series of reactions represented by the Schemes 1-6 below can be performed to synthesize the compound of formula (I), but not limited to.

Into a reaction flask, 4-bromobenzaldehyde (50 g, 270.2 mmol) and 4-acetylbiphenyl (55.68 g, 283.8 mmol) were added and mixed with 1000 mL of EtOH. After NaO-t-Bu (sodium tert-butoxide, STB) (29.83 g, 310.8 mmol) was added into the reaction flask and mixed, the mixture was reacted at room temperature (25° C.) overnight (with nitrogen introduction). After filtered, the solid residue was washed with 100 mL of water and 100 mL of methanol, and the solid was mixed with 400 mL of pure water and 100 mL of methanol for 15 min and filtered, and repeated 2 to 3 times. The solid was mixed with 400 mL of methanol for 15 min and filtered. The solid was mixed with 400 mL of ethanol for 15 min and filtered and then the solid residue was dried at 65° C. White solid intermediate A (84.7 g) was obtained, 86.28% yield.

Into a reaction flask, intermediate A (20 g, 55.1 mmol) and different derivatives of pyridinium chloride (60.6 mmol) were added and mixed with 200 mL of toluene. After STB (7.93 g, 82.6 mmol) was added into the reaction flask and mixed, the mixture was reacted at 100±5° C. for 16 hrs (with nitrogen introduction). After cooling, 300 mL of ethyl acetate (EA) was added into the mixture. The mixture was extracted with 200 mL of pure water for 4 times. The reactant was dehydrated with anhydrous sodium sulfate and filtered through. The filtrate was concentrated and precipitated by the addition of methanol, then filtered. The filtered solids were washed with methanol and dried to obtain solid intermediate B.

Into the reaction flask, 3-bromobenzaldehyde (50 g, 270.2 mmol) and 4-acetylbiphenyl (55.68 g, 283.8 mmol) were added and mixed with 1000 mL of EtOH. After STB (29.83 g, 310.8 mmol) was added into the reaction flask and mixed, the mixture was reacted at room temperature (25° C.) overnight (with nitrogen introduction). After filtered, the solid residue was washed with 100 mL of water and 100 mL of methanol, and the solid was mixed with 400 mL of pure water and 100 mL of methanol for 15 min and filtered, and repeated 2 to 3 times. The solid was mixed with 400 mL of methanol for 15 min and filtered. The solid was mixed with 400 mL of ethanol for 15 min and filtered and then the solid residue was dried at 65° C. White solid intermediate C (89.6 g) was obtained, 91.27% yield.

Into a reaction flask, intermediate C (20 g, 55.1 mmol) and different derivatives of pyridinium chloride (60.6 mmol) were added and mixed with 200 mL of toluene. After STB (7.93 g, 82.6 mmol) was added into the reaction flask and mixed, the mixture was reacted at 100±5° C. for 16 hrs (with nitrogen introduction). After cooling, 300 mL of ethyl acetate (EA) was added into the mixture. The mixture was extracted with 200 mL of pure water for 4 times. The reactant was dehydrated with anhydrous sodium sulfate and filtered through. The filtrate was concentrated and precipitated by the addition of methanol. The filtered solid was washed with methanol and dried to obtain solid intermediate D.

Into the reaction flask, 3,5-dibromobenzaldehyde (30 g, 113.7 mmol) and 4-acetylbiphenyl (23.42 g, 119.4 mmol) were added and mixed with 600 mL of EtOH. After STB (16.37 g, 170.5 mmol) was added into the reaction flask and mixed, the mixture was reacted at room temperature (25° C.) overnight (with nitrogen introduction). After filtered, the mixture was washed with 100 mL of water and 100 mL of methanol, and the solid was mixed with 250 mL of pure water and 50 mL of methanol for 15 min and filtered, and repeated 2 to 3 times. The solid was mixed with 200 mL of methanol for 15 min and filtered. The solid was mixed with 250 mL of ethanol for 15 min and then purified and filtered. Then the solid residue was dried at 65° C. Yellowish solid intermediate E (48.5 g) was obtained, 98.49% yield.

Into a reaction flask, intermediate E (20 g, 55.1 mmol) and different derivatives of pyridinium chloride (60.6 mmol) were added and mixed with 200 mL of toluene. After STB (7.93 g, 82.6 mmol) was added into the reaction flask and mixed, the mixture was reacted at 100±5° C. for 16 hrs (with nitrogen introduction). After cooling, 300 mL of ethyl acetate (EA) was added into the mixture. The mixture was extracted with 200 mL of pure water for 4 times. The reactant was dehydrated with anhydrous sodium sulfate and filtered through. The filtrate was concentrated and precipitated by the addition of methanol. The filtered solid was washed with methanol and dried to obtain solid intermediate F.

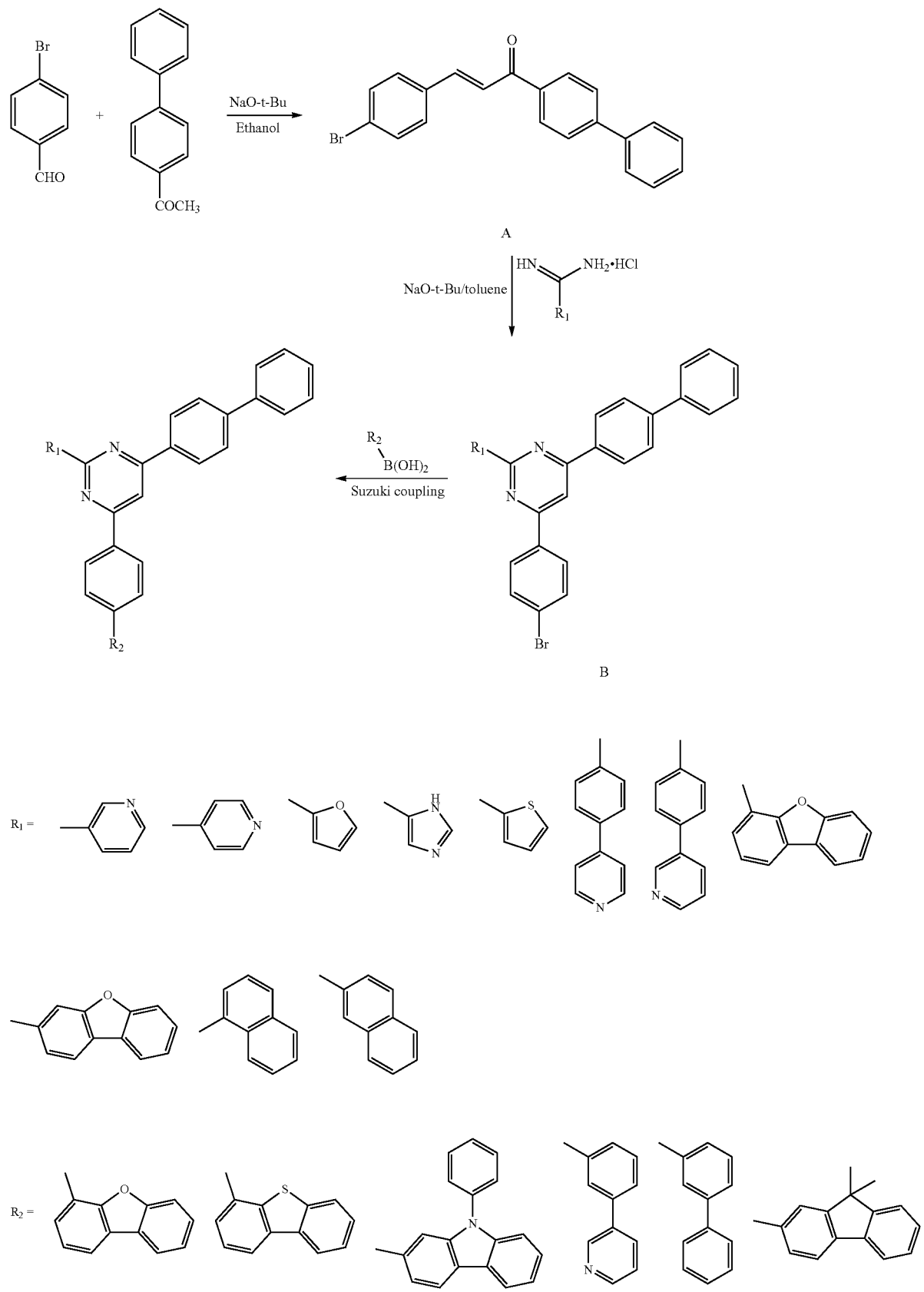

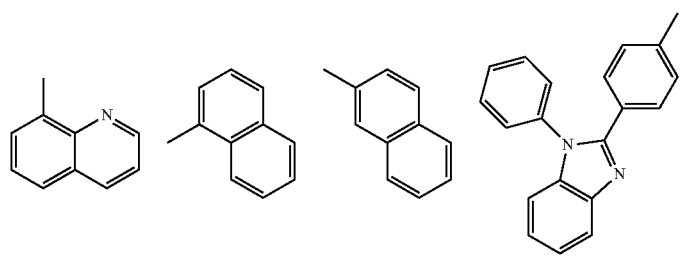
Scheme 2
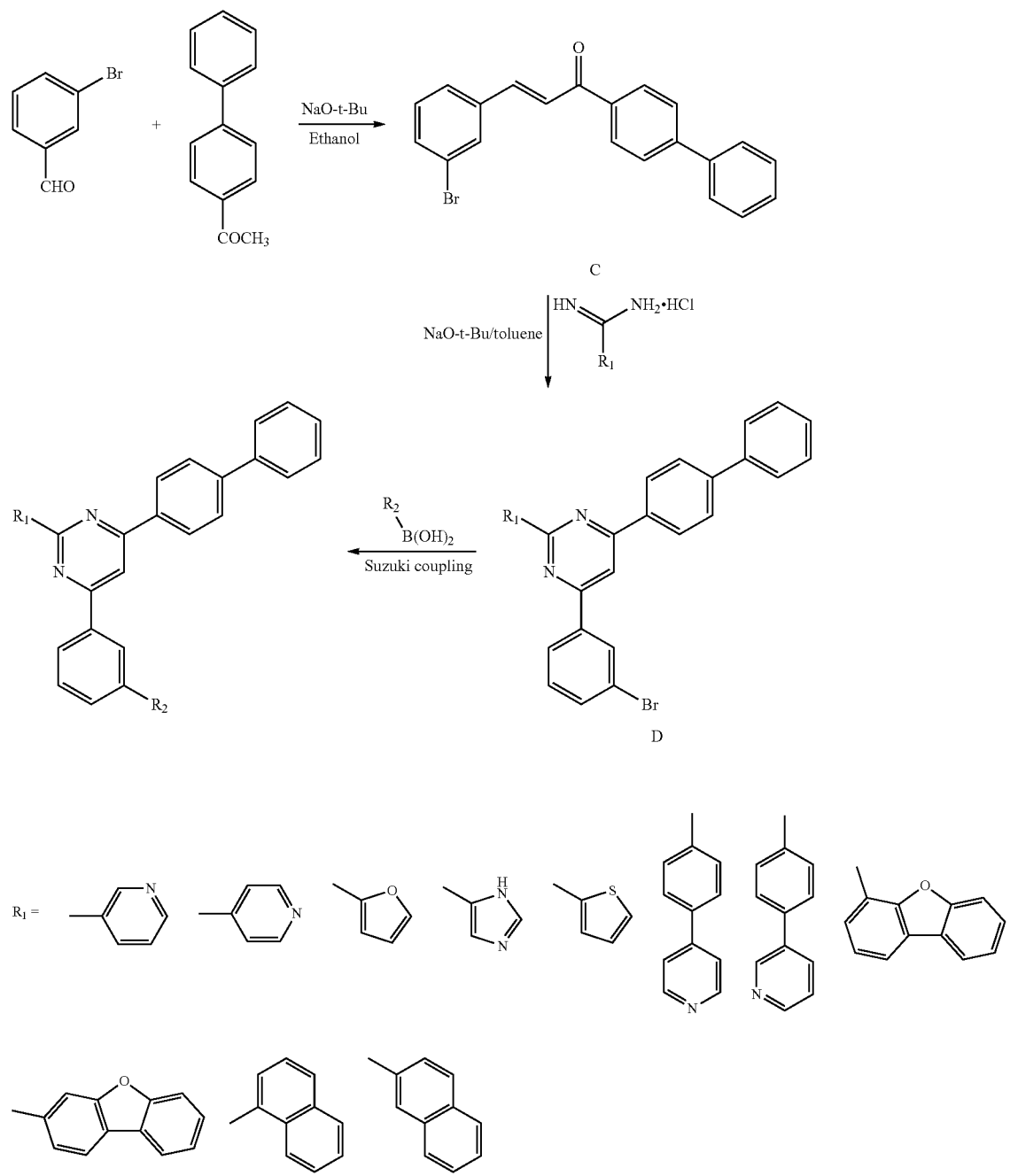

123 124
-continued
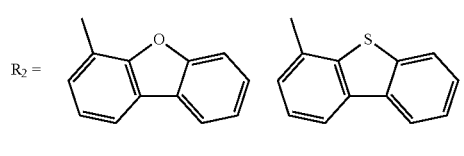
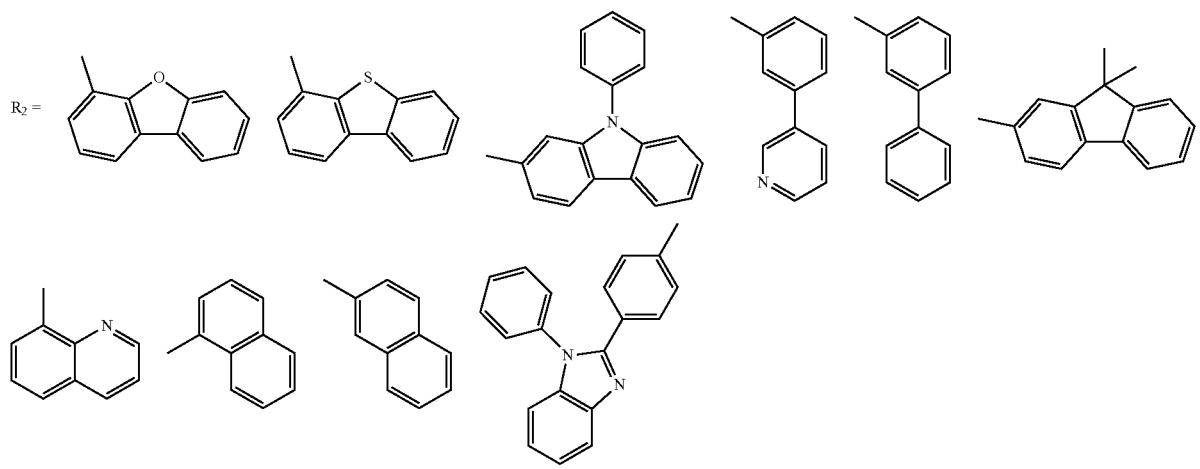
Scheme 3
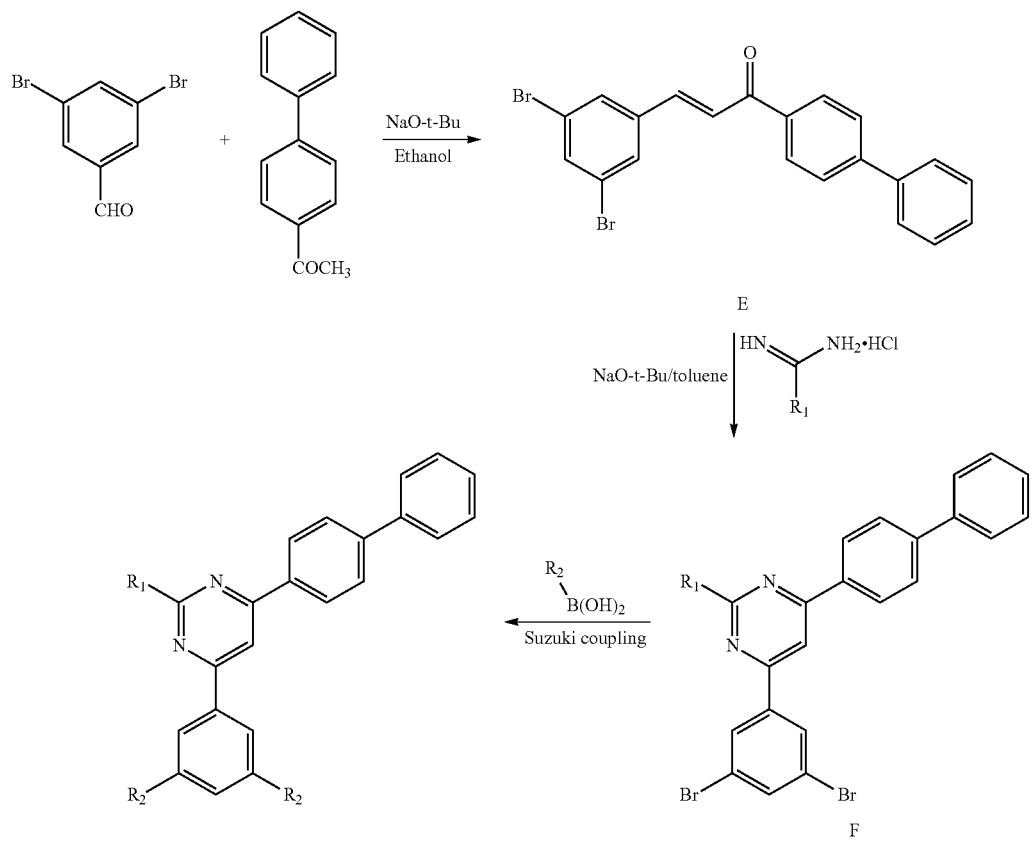
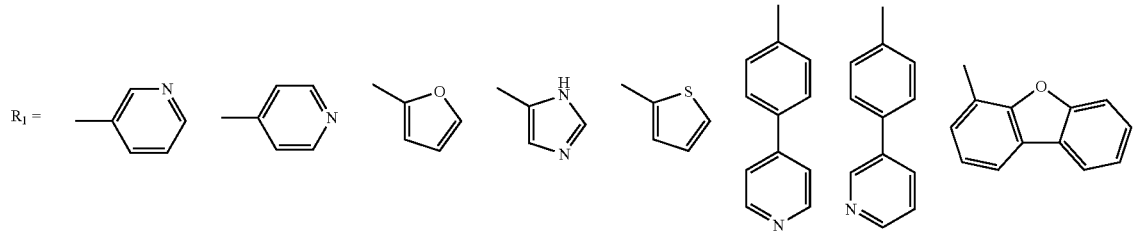

-continued
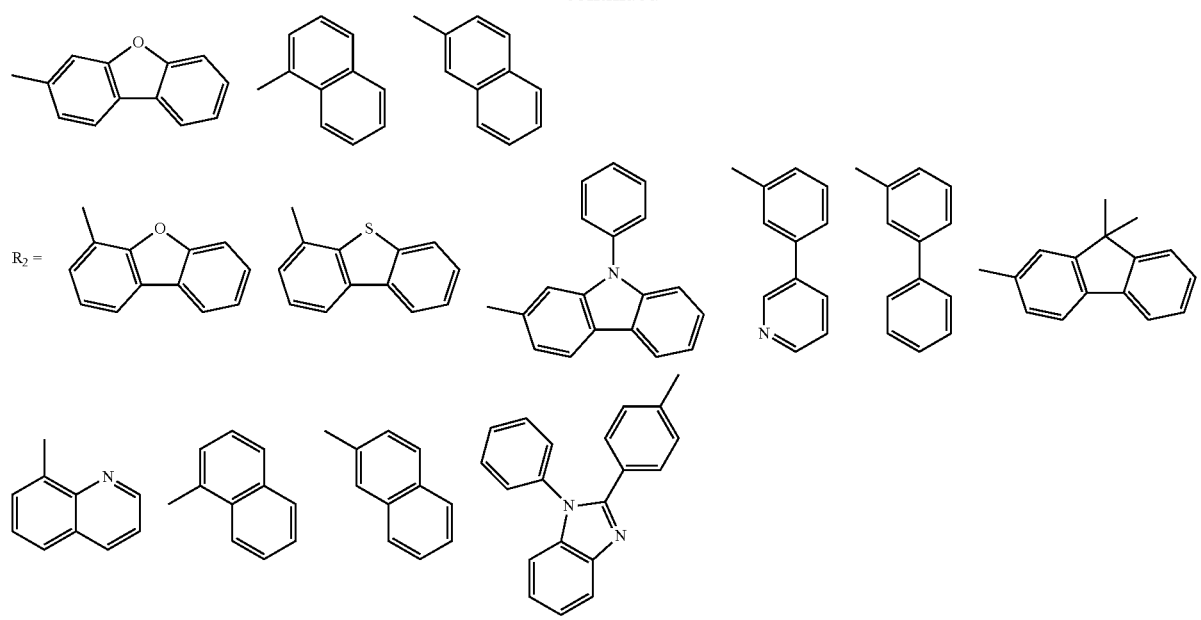
Scheme 4
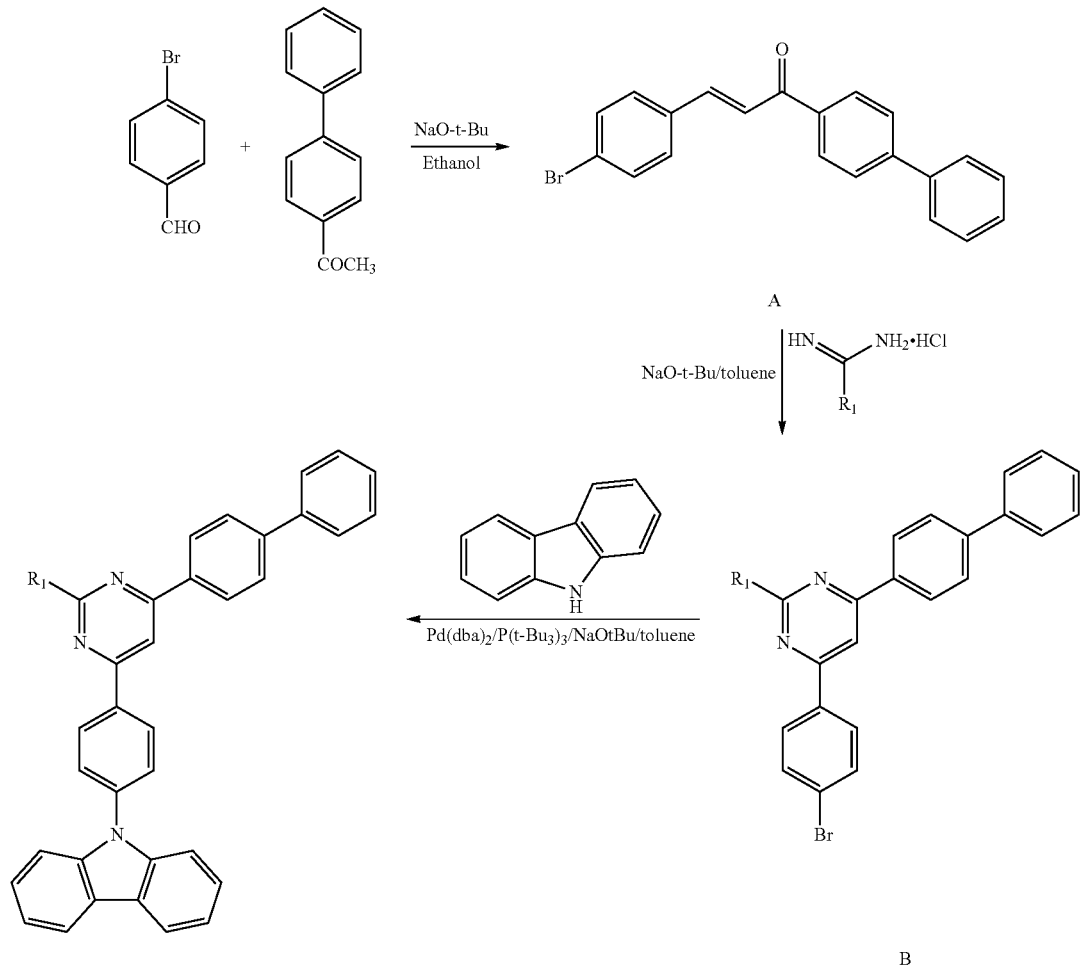

-continued
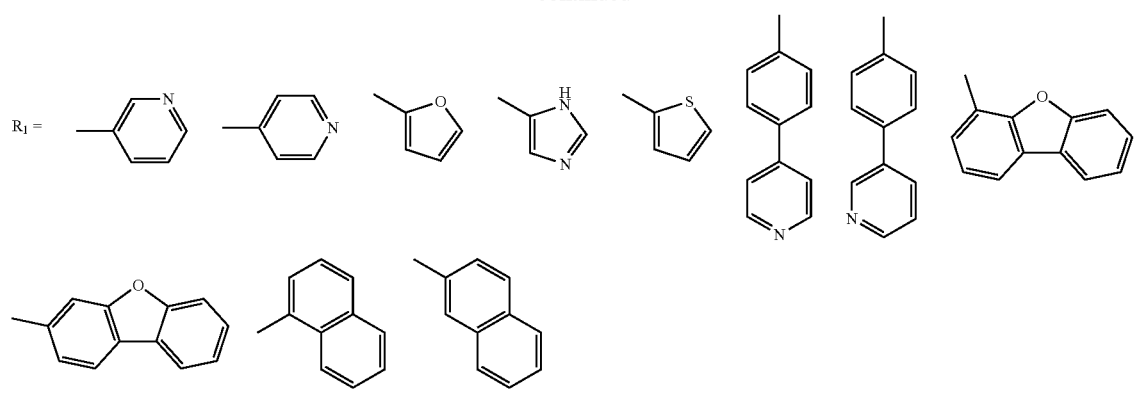
Scheme 5
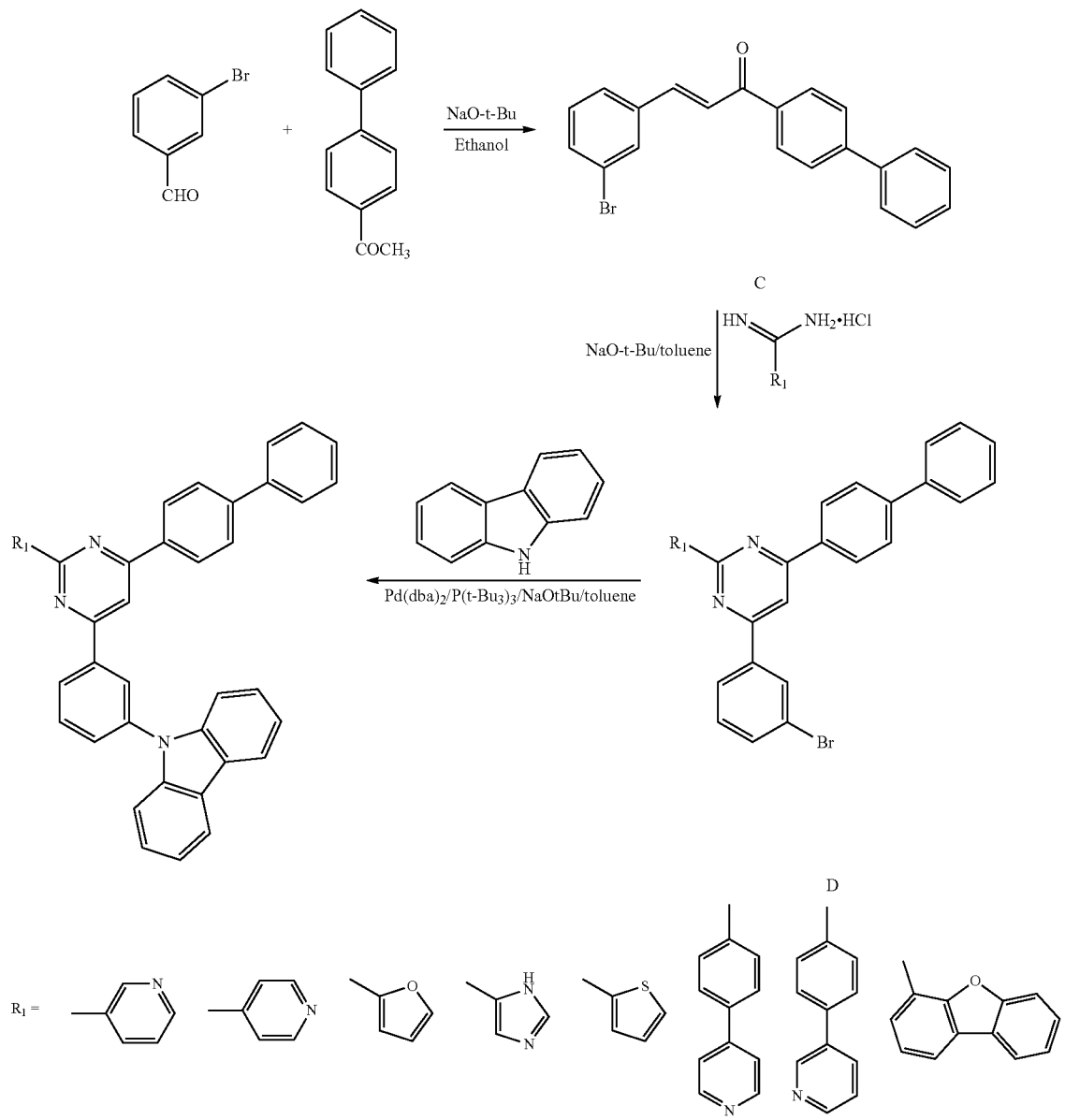

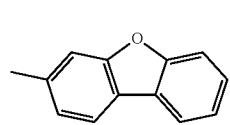 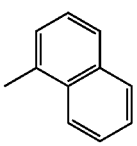 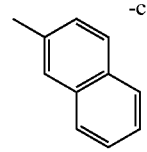
-continued
Scheme 6
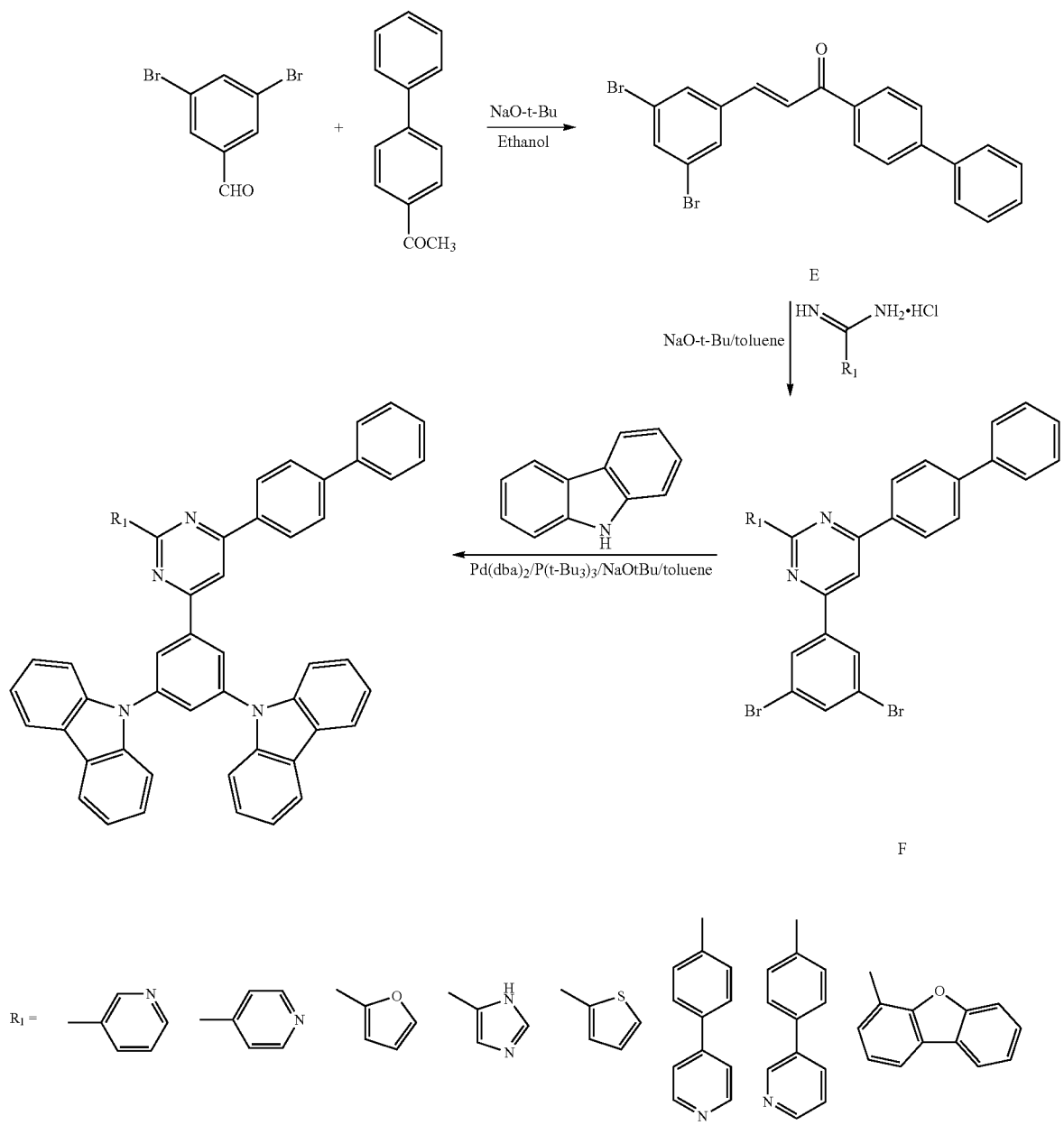
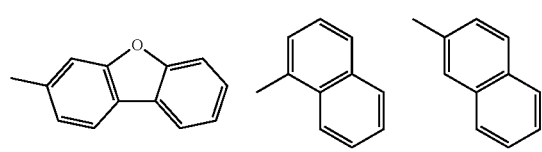

The present disclosure further provides an organic electroluminescent device, comprising a cathode; an anode; and an organic layer disposed between an anode and a cathode, wherein the organic layer comprises the compound of formula (I) of the present disclosure.

The compound of formula (I) can be used for the organic layer of an OLED. Therefore, the OLED of the present disclosure has at least one organic layer interposed between an anode and a cathode on a substrate, and the organic layer includes the aforementioned compound of formula (I). The organic layer may be an emitting layer, a hole block layer, an electron transport layer, an electron injection layer or a hole transport layer. Besides the organic layer, the organic electroluminescent device can further comprises at least one layer selected from the group consisting of an electron transport layer, an electron injection layer, an emitting layer, a hole block layer, and an electron block layer. The organic layer comprising the compound of formula (I) may preferably be an electron transport/injection layer and can be single material of the compound of formula (I), or can be in combination with electrically injecting dopants (n/p type). In an embodiment, the electron transport layer comprises the compound of formula (I).

Electrically conducting dopants to be used for the electron transport layer are preferably organic alkali/alkaline metal complexes, oxides, halides, carbonates, phosphates of alkali/alkaline group metals containing at least one metal selected from lithium and cesium. Such organic metal complexes are known in the aforementioned patent documents and elsewhere and a suitable organic metal complex can be selected from them and used in this disclosure.

Calculated by the weight of the organic layer, the content of the electrically conducting dopant is 0 wt % to 90 wt %. For example, the organic layer is electron transport layer or electron injection layer and the electrically conducting dopant in the electron transport/electron injection layer is preferably in the range of 25 wt % to 75 wt %.

In an embodiment, the organic layer is an electron transport layer.

In an embodiment, the electron transport layer comprises the compound of formula (I) and n-type electrically conducting dopant, and the content of the n-type electrically conducting dopant is more than 0 wt % to 75 wt %.

In an embodiment, calculated by the weight of the organic layer, the content of the compound of formula (I) is 25 wt % to 100 wt %. Besides, the thickness of the organic layer is 1 nm to 500 nm.

In another embodiment, the organic electroluminescent device further comprises at least one layer selected from the group consisting of an electron transport layer, an electron injection layer, an emitting layer, a hole block layer and an electron block layer. The emitting layer further comprises fluorescent or phosphorescent emitters.

In an embodiment, a hole injection layer, a hole transport layer, an emitting layer were further comprised between the anode and the organic layer, and an electron injection layer was further comprised between the organic layer and the cathode, and the organic layer is an electron transport layer.

Further, the compound of formula (I) may be included in the layer between the emitting layer and the electron transport layer. The emitting layer may comprise fluorescent and phosphorescent dopants and their corresponding fluorescent or phosphorescent host emitters, respectively.

Furthermore, the compound of formula (I) may be used in an electron injection/transport layer or a hole block layer and/or an electron block layer.

The structure of the organic electroluminescent device of this disclosure will be explained with reference to the drawing, but not limited thereto.

Figure 2:
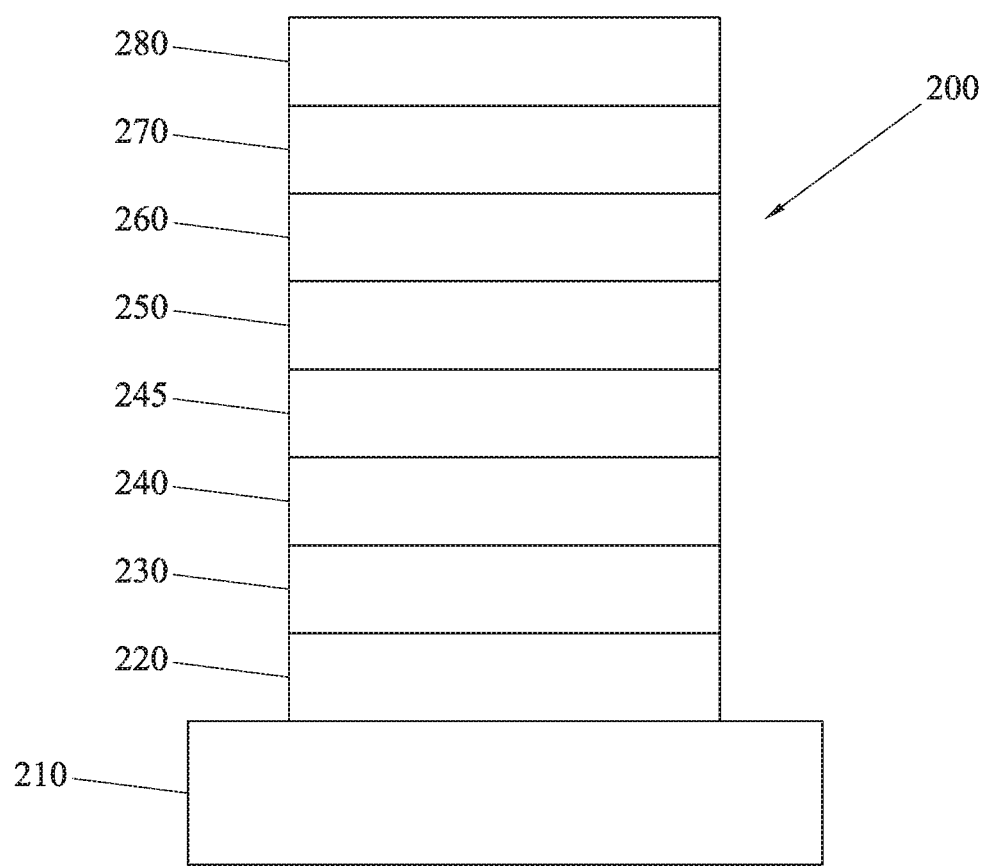
FIG. 2 is a cross-sectional view illustrating an organic electroluminescent device according to another embodiment of the present disclosure.
Figure 3:
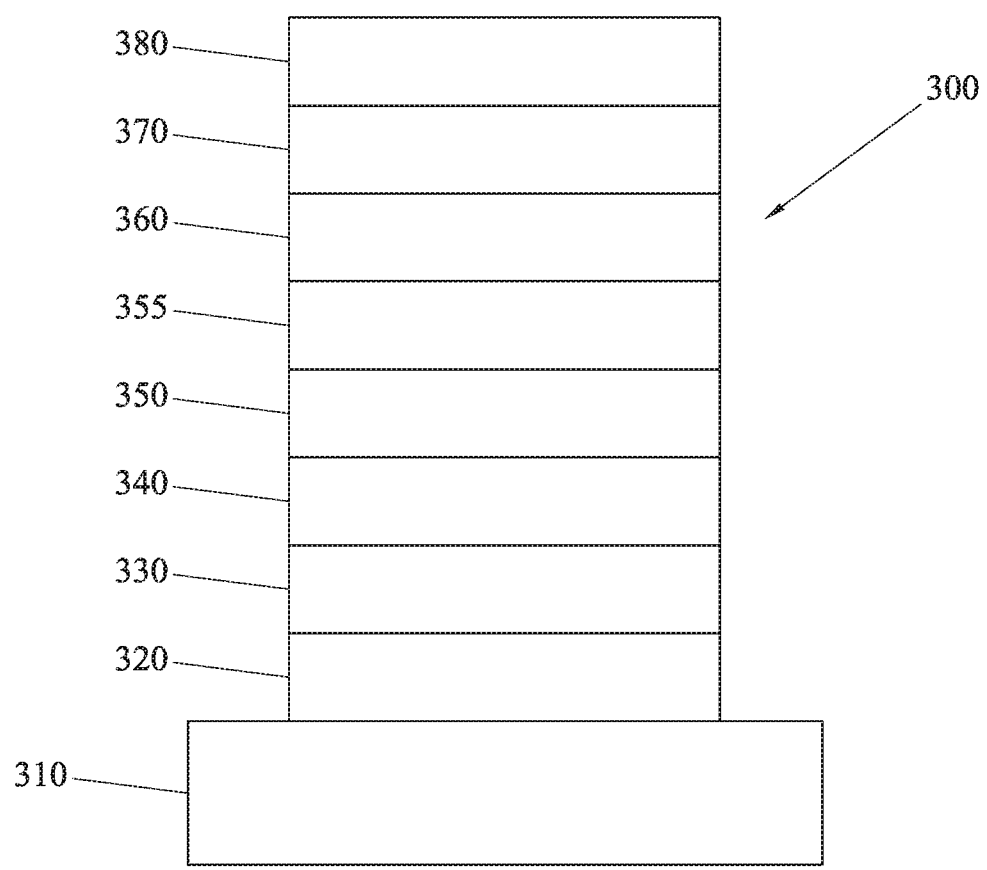
FIG. 3 is a cross-sectional view illustrating an organic electroluminescent device according to yet another embodiment of the present disclosure.

FIG. 1 is a schematic view showing a cross-sectional view of an organic electroluminescent device according to an embodiment of the present disclosure. An organic electroluminescent device 100 comprises a substrate 110, an anode 120, a hole injection layer 130, a hole transport layer 140, an emitting layer 150, an electron transport layer 160, an electron injection layer 170, and a cathode 180. The organic electroluminescent device 100 may be fabricated by depositing the aforementioned layers in order. FIG. 2 is a schematic view showing a cross-sectional view of an organic electroluminescent device according to another embodiment of the present disclosure, which is similar to that of FIG. 1. Besides substrate 210, anode 220, a hole injection layer 230, a hole transport layer 240, an emitting layer 250, an electron transport layer 260, an electron injection layer 270 and a cathode 280, the difference is that an exciton block layer 245 of the organic electroluminescent device of FIG. 2 is interposed between a hole transport layer 240 and an emitting layer 250. FIG. 3 is a schematic view showing a cross-sectional view of an organic electroluminescent device according to another embodiment of the present disclosure, which is also similar to that of FIG. 1. Besides substrate 310, anode 320, a hole injection layer 330, a hole transport layer 340, an emitting layer 350, an electron transport layer 360, an electron injection layer 370 and a cathode 380, the difference is that an exciton block layer 355 of the organic electroluminescent device of FIG. 3 is interposed between an emitting layer 350 and an electron transport layer 360.

Alternatively, the organic electroluminescent device may be fabricated using the reverse structures of the devices shown in FIGS. 1 to 3. In such reverse structures, one or more layer(s) may be added or omitted as needed.

Materials used for a hole injection layer, a hole transport layer, an electron block layer, a hole block layer, an emitting layer, and an electron injection layer may be those conventionally used. For example, an electron-transporting material for forming the electron transport layer differs from that for forming the emitting layer, and has a property of hole-transporting, so as to facilitate hole mobility in the electron transport layer, and to prevent carrier accumulation due to the difference of dissociation energy between the emitting layer and the electron transport layer.

In addition, U.S. Pat. No. 5,844,363 discloses a flexible and transparent substrate in combination with anode, and the entire disclosure of which is incorporated herein by reference. An example of a p-type doped hole transport layer is m-MTDATA doped with $F_4$-TCNQ at a molar ratio of 50:1, as disclosed in US Patent Application Publication No. 20030230980, and the entire disclosure of which is incorporated herein by reference. An example of an n-type doped electron transport layer is BPhen doped with Li at a molar ratio of 1:1, as disclosed in US Patent Application Publication No. 20030230980, and the entire disclosure of which is incorporated herein by reference. The entire disclosures of the exemplary cathodes of U.S. Pat. Nos. 5,703,436 and 5,707,745 are incorporated herein by reference, wherein the cathodes have a thin layer of metal such as Mg:Ag with an overlaying transparent, electrically-conductive, sputter-deposited ITO layer. The theory and use of each block layers is described in U.S. Pat. No. 6,097,147 and US Patent Application Publication No. 20030230980, and the entire disclosures of which are incorporated herein by reference. The entire disclosure of the exemplary of the injection layers of US Patent Application Publication No. 20040174116 and the protective layers described in the same application are incorporated herein by reference.

Structures and materials not specifically described may also be used in the present disclosure, such as the organic electroluminescent device comprising polymeric materials (PLEDs) disclosed in U.S. Pat. No. 5,247,190, and the entire disclosures of which are incorporated herein by reference. Furthermore, the organic electroluminescent device having a single organic layer or the organic electroluminescent device formed by stacking as disclosed in U.S. Pat. No. 5,707,745 may be used, and the entire disclosures of which are incorporated herein by reference.

Unless otherwise specified, any layers of the various embodiments may be deposited by any suitable method. For the organic layers, preferred methods include such as thermal evaporation and jet printing described in U.S. Pat. Nos. 6,013,982 and 6,087,196, herein incorporated by reference in its entirety; organic vapor phase deposition (OVPD) described in U.S. Pat. No. 6,337,102, herein incorporated by reference in its entirety; and deposition by organic vapor jet printing (OVJP) described in U.S. patent application Ser. No. 10/233,470, herein incorporated by reference in its entirety. Other suitable deposition methods include spin coating and other solution-based processes. It is preferable to conduct solution-based processes in environment containing nitrogen or inert gas. For the other layers, preferred methods include thermal evaporation. Preferred patterning methods include such as deposition through a mask followed by cold welding and the processes of patterning and deposition by integrated ink-jet and OVJD described in U.S. Pat. Nos. 6,294,398 and 6,468,819, herein incorporated by reference in their entirety. Certainly, other methods may be used. The materials to be deposited may be modified to be compatible with the particular deposition method.

The compound of formula (I) of the present disclosure may be used to fabricate amorphous thin layers applied to an organic electroluminescent device by vacuum deposition or spin coating. When the compound is used in any of the organic layers described above, it exhibits a longer lifetime and better thermal stability with high efficiency and low driving voltage.

An organic electroluminescent device of the present disclosure is applicable to a single device, which is a device with its structure arranged in array, or a device having the anode and the cathode arranged in an X-Y coordinates of the array. The present disclosure can provide an organic electroluminescent device with significantly improved luminous efficiency and driving stability over the conventional devices. Besides, when combining with phosphorescent dopants in the emitting layer, the organic electroluminescent device of the present disclosure can perform better and emits white light while applying to full-color or multicolor display panels.

Several properties and effects of the present disclosure will be described in more detail below with reference to the examples. However, these detailed examples are merely used to illustrate the properties of the present disclosure; the present disclosure will not be limited to these examples.

Synthesis Example 1 (Synthesis of Compound 1-4)

Into the reaction flask, 4-biphenyl-4-yl-6-(4-bromophenyl)-2-pyridin-3-yl-pyrimidine (10 g, 21.5 mmol) and 3-(3-pyridyl)phenylboronic acid (5.14 g, 25.8 mmol) were added, and 100 mL of toluene was added thereto. $K_2CO_3$ (4.46 g, 32.3 mmol) was dissolved in 40 mL of dd$H_2O$ and added into the reaction flask. Pd(PPh$_3$)$_4$ (0.371 g, 0.3 mmol) was added thereto followed by the addition of 20 mL of alcohol. The mixture was stirred and refluxed at 80° C. for 16 hr. After the reaction was completed, 150 mL of dd$H_2O$ was added thereto and the mixture was stirred until cooling to room temperature. The reactant was filtered and the solid residue was obtained and washed with dd$H_2O$ and acetone. The mixed solution (200 mL of dd$H_2O$, 50 mL of methanol and 50 mL of acetone) was added to the solid residue, and the mixture was stirred for 30 min and filtered, repeated 2 times. The solid was oven-dried and redissolved in 1000 mL of toluene by heating and passed through a silica gel column. The eluent was concentrated by distillation, and then 300 mL of methanol was added thereto and stirred for 30 min. After the mixture was filtered and oven-dried, compound 1-4 was obtained as a white solid (4.7 g, 40.5% yield).

$^1$H NMR (400 MHz, CDCl$_3$, δ): 9.943 (s, 1H); 9.001-8.981 (d, H); 8.944 (s, 1H); 8.776-8.763 (d, 1H); 8.647-8.640 (d, 1H); 8.436-8.391 (t, 4H); 8.167 (s, 1H); 7.982-7.961 (d, 1H); 7.878-7.813 (m, 5H); 7.741-7.633 (m, 5H); 7.526-7.419 (m, 5H).

Synthesis Example 2 (Synthesis of Compound 1-5)

Into the reaction flask, 4-biphenyl-4-yl-6-(4-bromophenyl)-2-pyridin-3-yl-pyrimidine (10 g, 21.5 mmol) and 3-biphenyl boronic acid (5.12 g, 25.8 mmol) were added, and 100 mL of toluene was added thereto. $K_2CO_3$ (4.46 g, 32.3 mmol) was dissolved in 40 mL of dd$H_2O$ and added into the reaction flask. Pd(PPh$_3$)$_4$ (0.371 g, 0.3 mmol) was added thereto and followed by the addition of 20 mL of alcohol. The mixture was stirred and refluxed at 80° C. for 16 hr. After the reaction was completed, 150 mL of dd$H_2O$ was added thereto and the mixture was stirred until cooling to room temperature. The reactant was filtered and the solid residue was obtained and washed with dd$H_2O$ and acetone. The mixed solution (200 mL of dd$H_2O$, 50 mL of methanol and 50 mL of acetone) was added to the solid residue, and the mixture was stirred for 30 min and filtered, repeated 2 times. The solid was oven-dried and redissolved in 1000 mL of toluene by heating and passed through a silica gel column. The eluent was concentrated by distillation, and then 300 mL of methanol was added thereto and stirred for 30 min. After the mixture was filtered and oven-dried, compound 1-5 was obtained as a white solid (5.8 g, 50.0% yield).

$^1$H NMR (400 MHz, CDCl$_3$, δ): 9.946-9.943 (d, 1H); 8.996-8.976 (d, 1H); 8.777-8.760 (d, 1H); 8.423-8.388 (t, 4H); 8.161 (s, 1H); 7.910-7.811 (m, 5H); 7.718-7.632 (m, 6H); 7.595-7.558 (t, 1H); 7.526-7.476 (m, 5H); 7.439-7.382 (m, 2H).

Synthesis Example 3 (Synthesis of Compound 1-6)

Into the reaction flask, 4-biphenyl-4-yl-6-(4-bromophenyl)-2-pyridin-3-yl-pyrimidine (10 g, 21.5 mmol) and dibenzofuran-4-boronic acid (5.48 g, 25.8 mmol) were added, and 100 mL of toluene was added thereto. $K_2CO_3$ (4.46 g, 32.3 mmol) was dissolved in 40 mL of dd$H_2O$ and added into the reaction flask. Pd(PPh$_3$)$_4$ (0.371 g, 0.3 mmol) was added thereto and followed by the addition of 20 mL of alcohol. The mixture was stirred and refluxed at 80° C. for 16 hr. After the reaction was completed, 150 mL of dd$H_2O$ was added thereto and the mixture was stirred until cooling to room temperature. The reactant was filtered and the solid residue was obtained and washed with dd$H_2O$ and acetone. The mixed solution (200 mL of dd$H_2O$, 50 mL of methanol and 50 mL of acetone) was added to the solid residue, and the mixture was stirred for 30 min and filtered, repeated 2 times. The solid was oven-dried and redissolved in 1000 mL of toluene by heating and passed through a silica gel column. The eluent was concentrated by distillation, and then 300 mL of methanol was added thereto and stirred for 30 min. After the mixture was filtered and oven-dried, compound 1-6 was obtained as a white solid (7.2 g, 60.6% yield).

$^1$H NMR (400 MHz, CDCl$_3$, δ): 9.965-9.961 (s, 1H); 9.028-8.998 (d, 1H); 8.784-8.768 (d, 1H); 8.507-8.486 (d, 2H); 8.424-8.403 (d, 2H); 8.208 (s, 1H); 8.177-8.155 (d, 2H); 8.037-7.997 (t, 2H); 7.842-7.821 (d, 2H); 7.733-7.705 (d, 3H); 7.658-7.637 (d, 1H); 7.530-7.475 (m, 5H); 7.439-7.377 (m, 2H).

Synthesis Example 4 (Synthesis of Compound 1-7)

Into the reaction flask, 4-biphenyl-4-yl-6-(4-bromophenyl)-2-pyridin-3-yl-pyrimidine (10 g, 21.5 mmol) and dibenzothiophene-4-boronic acid (5.89 g, 25.8 mmol) were added, and 100 mL of toluene was added thereto. K$_2$CO$_3$ (4.46 g, 32.3 mmol) was dissolved in 40 mL of ddH$_2$O and added into the reaction flask. Pd(PPh$_3$)$_4$ (0.371 g, 0.3 mmol) was added thereto and followed by the addition of 20 mL of alcohol. The mixture was stirred and refluxed at 80° C. for 16 hr. After the reaction was completed, 150 mL of ddH$_2$O was added thereto and the mixture was stirred until cooling to room temperature. The reactant was filtered and the solid residue was obtained and washed with ddH$_2$O and acetone. The mixed solution (200 mL of ddH$_2$O, 50 mL of methanol and 50 mL of acetone) was added to the solid residue, and the mixture was stirred for 30 min and filtered, repeated 2 times. The solid was oven-dried and redissolved in 1000 mL of toluene by heating and passed through a silica gel column. The eluent was concentrated by distillation, and then 300 mL of methanol was added thereto and stirred for 30 min. After the mixture was filtered and oven-dried, compound 1-7 was obtained as a white solid (7.1 g, 58.0% yield).

$^1$H NMR (400 MHz, CDCl$_3$, δ): 9.965-9.959 (d, 1H); 9.015-8.996 (m, 1H); 8.787-8.772 (m, 1H); 8.469-8.407 (m, 4H); 8.231-8.203 (m, 3H); 7.995-7.974 (d, 2H); 7.883-7.822 (m, 3H); 7.726-7.703 (d, 2H); 7.641-7.578 (m, 2H); 7.531-7.403 (m, 6H).

Synthesis Example 5 (Synthesis of Compound 1-10)

Into the reaction flask, 4-biphenyl-4-yl-6-(4-bromophenyl)-2-pyridin-3-yl-pyrimidine (10 g, 21.5 mmol) and 4-(1-phenyl-1H-benzo[d]imidazol-2-yl)phenylboronic acid (8.12 g, 25.8 mmol) were added, and 100 mL of toluene was added thereto. K$_2$CO$_3$ (4.46 g, 32.3 mmol) was dissolved in 40 mL of ddH$_2$O and added into the reaction flask. Pd(PPh$_3$)$_4$ (0.371 g, 0.3 mmol) was added thereto and followed by the addition of 20 mL of alcohol. The mixture was stirred and refluxed at 80° C. for 16 hr. After the reaction was completed, 150 mL of ddH$_2$O was added thereto and the mixture was stirred until cooling to room temperature. The reactant was filtered and the solid residue was obtained and washed with ddH$_2$O and acetone. The mixed solution (200 mL of ddH$_2$O, 50 mL of methanol and 50 mL of acetone) was added to the solid residue, and the mixture was stirred for 30 min and filtered, repeated 2 times. The solid was oven-dried and redissolved in 1000 mL of toluene by heating and passed through a silica gel column. The eluent was concentrated by distillation, and then 300 mL of methanol was added thereto and stirred for 30 min. After the mixture was filtered and oven-dried, compound 1-10 was obtained as a white solid (3.1 g, 43.0% yield).

$^1$H NMR (400 MHz, CDCl$_3$, δ): 9.931 (s, 1H); 8.992-8.969 (d, 1H); 8.757 (d, 1H); 8.369-8.362 (d, 4H); 8.148 (s, 1H); 7.929-7.910 (d, 1H); 7.822-7.802 (d, 4H); 7.729-7.644 (m, 7H); 7.565-7.487 (m, 7H); 7.433-7.386 (m, 4H).

Synthesis Example 6 (Synthesis of Compound 2-6)

Into the reaction flask, 4-biphenyl-4-yl-6-(4-bromophenyl)-2-pyridin-4-yl-pyrimidine (10 g, 21.5 mmol) and dibenzofuran-4-boronic acid (5.48 g, 25.8 mmol) were added, and 100 mL of toluene was added thereto. K$_2$CO$_3$ (4.46 g, 32.3 mmol) was dissolved in 40 mL of ddH$_2$O and added into the reaction flask. Pd(PPh$_3$)$_4$ (0.371 g, 0.3 mmol) was added thereto and followed by the addition of 20 mL of alcohol. The mixture was stirred and refluxed at 80° C. for 16 hr. After the reaction was completed, 150 mL of ddH$_2$O was added thereto and the mixture was stirred until cooling to room temperature. The reactant was filtered and the solid residue was obtained and washed with ddH$_2$O and acetone. The mixed solution (200 mL of ddH$_2$O, 50 mL of methanol and 50 mL of acetone) was added to the solid residue, and the mixture was stirred for 30 min and filtered, repeated 2 times. The solid was oven-dried and redissolved in 1000 mL of toluene by heating and passed through a silica gel column. The eluent was concentrated by distillation, and then 300 mL of methanol was added thereto and stirred for 30 min. After the mixture was filtered and oven-dried, compound 2-6 was obtained as a white solid (9.6 g, 80.9% yield).

$^1$H NMR (400 MHz, CDCl$_3$, δ): 8.868-8.853 (d, 2H); 8.617-8.602 (d, 2H); 8.514-8.487 (d, 2H); 8.424-8.403 (d, 2H); 8.248 (s, 1H); 8.187-8.160 (d, 2H); 8.038-8.005 (t, 2H); 7.852-7.825 (d, 2H); 7.734-7.703 (m, 3H); 7.656-7.637 (d, 1H); 7.534-7.478 (m, 4H); 7.448-7.380 (m, 2H).

Synthesis Example 7 (Synthesis of Compound 2-10)

Into the reaction flask, 4-biphenyl-4-yl-6-(4-bromophenyl)-2-pyridin-4-yl-pyrimidine (10 g, 21.5 mmol) and 4-(1-phenyl-1H-benzo[d]imidazol-2-yl)phenylboronic acid (8.12 g, 25.8 mmol) were added, and 100 mL of toluene was added thereto. K$_2$CO$_3$ (4.46 g, 32.3 mmol) was dissolved in 40 mL of ddH$_2$O and added into the reaction flask. Pd(PPh$_3$)$_4$ (0.371 g, 0.3 mmol) was added thereto and followed by the addition of 20 mL of alcohol. The mixture was stirred and refluxed at 80° C. for 16 hr. After the reaction was completed, 150 mL of ddH$_2$O was added thereto and the mixture was stirred until cooling to room temperature. The reactant was filtered and the solid residue was obtained and washed with ddH$_2$O and acetone. The mixed solution (200 mL of ddH$_2$O, 50 mL of methanol and 50 mL of acetone) was added to the solid residue, and the mixture was stirred for 30 min and filtered, repeated 2 times. The solid was oven-dried and redissolved in 1000 mL of toluene by heating and passed through a silica gel column. The eluent was concentrated by distillation, and then 300 mL of methanol was added thereto and stirred for 30 min. After the mixture was filtered and oven-dried, compound 2-10 was obtained as a white solid (11 g, 78.0% yield).

$^1$H NMR (400 MHz, CDCl$_3$, δ): δ 8.847-8.833 (d, 2H); 8.574-8.559 (d, 2H); 8.390-8.359 (m, 4H); 8.168 (s, 1H); 7.932-7.912 (d, 1H); 7.823-7.791 (m, 4H); 7.730-7.687 (t, 4H); 7.656-7.635 (d, 2H); 7.586-7.486 (m, 5H); 7.436-7.346 (m, 4H); 7.314-7.258 (t, 2H).

Synthesis Example 8 (Synthesis of Compound 12-4)

Into the reaction flask, 4-biphenyl-4-yl-6-(3-bromophenyl)-2-pyridin-3-yl-pyrimidine (10 g, 21.5 mmol) and 3-(3- pyridyl)phenylboronic acid (5.14 g, 25.8 mmol) were added, and 100 mL of toluene was added thereto. $K_2CO_3$ (4.46 g, 32.3 mmol) was dissolved in 40 mL of dd$H_2O$ and added into the reaction flask. Pd(PPh$_3$)$_4$ (0.371 g, 0.3 mmol) was added thereto and followed by the addition of 20 mL of alcohol. The mixture was stirred and refluxed at 80° C. for 16 hr. After the reaction was completed, 150 mL of dd$H_2O$ was added thereto and the mixture was stirred until cooling to room temperature. The reactant was filtered and the solid residue was obtained and washed with dd$H_2O$ and acetone. The mixed solution (200 mL of dd$H_2O$, 50 mL of methanol and 50 mL of acetone) was added to the solid residue, and the mixture was stirred for 30 min and filtered, repeated 2 times. The solid was oven-dried and redissolved in 1000 mL of toluene by heating and passed through a silica gel column. The eluent was concentrated by distillation, and then 300 mL of methanol was added thereto and stirred for 30 min. After the mixture was filtered and oven-dried, compound 12-4 was obtained as a white solid (8.7 g, 75.0% yield).

$^1$H NMR (400 MHz, CDCl$_3$, δ): 9.933-9.937 (s, 1H); 8.987-8.950 (t, 2H); 8.766-8.755 (d, 1H); 8.644-8.632 (d, 1H); 8.531 (s, 1H); 8.403-8.382 (d, 2H); 8.314-8.294 (d, 1H); 8.167 (s, 1H); 7.987-7.966 (d, 1H); 7.888 (s, 1H); 7.847-7.638 (m, 9H); 7.518-7.400 (m, 5H).

Synthesis Example 9 (Synthesis of Compound 12-6)

Into the reaction flask, 4-biphenyl-4-yl-6-(3-bromophenyl)-2-pyridin-3-yl-pyrimidine (10 g, 21.5 mmol) and dibenzofuran-4-boronic acid (5.48 g, 25.8 mmol) were added, and 100 mL of toluene was added thereto. $K_2CO_3$ (4.46 g, 32.3 mmol) was dissolved in 40 mL of dd$H_2O$ and added into the reaction flask. Pd(PPh$_3$)$_4$ (0.371 g, 0.3 mmol) was added thereto and followed by the addition of 20 mL of alcohol. The mixture was stirred and refluxed at 80° C. for 16 hr. After the reaction was completed, 150 mL of dd$H_2O$ was added thereto and the mixture was stirred until cooling to room temperature. The reactant was filtered and the solid residue was obtained and washed with dd$H_2O$ and acetone. The mixed solution (200 mL of dd$H_2O$, 50 mL of methanol and 50 mL of acetone) was added to the solid residue, and the mixture was stirred for 30 min and filtered, repeated 2 times. The solid was oven-dried and redissolved in 1000 mL of toluene by heating and passed through a silica gel column. The eluent was concentrated by distillation, and then 300 mL of methanol was added thereto and stirred for 30 min. After the mixture was filtered and oven-dried, compound 12-6 was obtained as a white solid (8.1 g, 68.0% yield).

$^1$H NMR (400 MHz, CDCl$_3$, δ): 9.970 (d, 1H); 9.022-8.992 (d, 1H); 8.848-8.840 (t, 1H); 8.770-8.761 (d, 1H); 8.415-8.394 (d, 2H); 8.362-8.342 (d, 1H); 8.209 (s, 1H); 8.139-8.121 (d, 1H); 8.046-8.008 (t, 2H); 7.824-7.641 (m, 4H); 7.534-7.466 (m, 5H); 7.431-7.378 (m, 2H).

Synthesis Example 10 (Synthesis of Compound 12-10)

Into the reaction flask, 4-biphenyl-4-yl-6-(3-bromophenyl)-2-pyridin-3-yl-pyrimidine (10 g, 21.5 mmol) and 4-(1-phenyl-1H-benzo[d]imidazol-2-yl)phenylboronic acid (8.12 g, 25.8 mmol) were added, and 100 mL of toluene was added thereto. $K_2CO_3$ (4.46 g, 32.3 mmol) was dissolved in 40 mL of dd$H_2O$ and added into the reaction flask. Pd(PPh$_3$)$_4$ (0.371 g, 0.3 mmol) was added thereto and followed by the addition of 20 mL of alcohol. The mixture was stirred and refluxed at 80° C. for 16 hr. After the reaction was completed, 150 mL of dd$H_2O$ was added thereto and the mixture was stirred until cooling to room temperature. The reactant was filtered and the solid residue was obtained and washed with dd$H_2O$ and acetone. The mixed solution (200 mL of dd$H_2O$, 50 mL of methanol and 50 mL of acetone) was added to the solid residue, and the mixture was stirred for 30 min and filtered, repeated 2 times. The solid was oven-dried and redissolved in 1000 mL of toluene by heating and passed through a silica gel column. The eluent was concentrated by distillation, and then 300 mL of methanol was added thereto and stirred for 30 min. After the mixture was filtered and oven-dried, compound 12-10 was obtained as a white solid (7.8 g, 55.4% yield).

$^1$H NMR (400 MHz, CDCl$_3$, δ):
9.925 (s, 1H); 8.977-8.959 (d, 1H); 8.767-8.757 (d, 1H); 8.490 (s, 1H); 8.398-8.377 (d, 1H); 8.272-8.251 (d, 1H); 8.140 (s, 1H); 7.931-7.911 (d, 1H); 7.823-7.776 (t, 3H); 7.748-7.631 (m, 8H); 7.583-7.471 (m, 7H); 7.433-7.346 (m, 4H).

Synthesis Example 11 (Synthesis of Compound 23-6)

Into the reaction flask, 4-biphenyl-4-yl-6-(3,5-dibromophenyl)-2-pyridin-3-yl-pyrimidine (10 g, 18.4 mmol) and dibenzofuran-4-boronic acid (8.6 g, 40.6 mmol) were added, and 100 mL of toluene was added thereto. $K_2CO_3$ (4.46 g, 32.3 mmol) was dissolved in 40 mL of dd$H_2O$ and added into the reaction flask. Pd(PPh$_3$)$_4$ (0.371 g, 0.3 mmol) was added thereto and followed by the addition of 20 mL of alcohol. The mixture was stirred and refluxed at 80° C. for 16 hr. After the reaction was completed, 150 mL of dd$H_2O$ was added thereto and the mixture was stirred until cooling to room temperature. The reactant was filtered and the solid residue was obtained and washed with dd$H_2O$ and acetone. The mixed solution (200 mL of dd$H_2O$, 50 mL of methanol and 50 mL of acetone) was added to the solid residue, and the mixture was stirred for 30 min and filtered, repeated 2 times. The solid was oven-dried and redissolved in 1000 mL of toluene by heating and passed through a silica gel column. The eluent was concentrated by distillation, and then 300 mL of methanol was added thereto and stirred for 30 min. After the mixture was filtered and oven-dried, compound 23-6 was obtained as a white solid (7.2 g, 54.4% yield).

$^1$H NMR (400 MHz, CDCl$_3$, δ): δ 10.009-10.003 (d, 1H); 9.053-9.033 (d, 1H); 8.887-8.883 (s, 2H); 8.778-8.766 (d, 1H); 8.627 (t, 1H); 8.440-8.418 (d, 2H); 8.302 (s, 1H); 8.064-8.045 (d, 1H); 7.854-7.807 (m, 4H); 7.707-7.651 (m, 4H); 7.572-7.469 (m, 7H); 7.423-7.387 (m, 3H).

Synthesis Example 12 (Synthesis of Compound 23-8)

Into the reaction flask, 4-biphenyl-4-yl-6-(3,5-dibromophenyl)-2-pyridin-3-yl-pyrimidine (10 g, 18.4 mmol) and naphthalen-1-ylboronic acid (7.9 g, 45.9 mmol) were added, and 100 mL of toluene was added thereto. $K_2CO_3$ (4.46 g, 32.3 mmol) was dissolved in 40 mL of dd$H_2O$ and added into the reaction flask. Pd(PPh$_3$)$_4$ (0.371 g, 0.3 mmol) was added thereto and followed by the addition of 20 mL of alcohol. The mixture was stirred and refluxed at 80° C. for 16 hr. After the reaction was completed, 150 mL of dd$H_2O$ was added thereto and the mixture was stirred until cooling to room temperature. The reactant was filtered and the solid residue was obtained and washed with dd$H_2O$ and acetone. The mixed solution (200 mL of dd$H_2O$, 50 mL of methanol and 50 mL of acetone) was added to the solid residue, and the mixture was stirred for 30 min and filtered, repeated 2 times. The solid was oven-dried and redissolved in 1000 mL of toluene by heating and passed through a silica gel column. The eluent was concentrated by distillation, and then 300 mL of methanol was added thereto and stirred for 30 min. After the mixture was filtered and oven-dried, compound 23-8 was obtained as a white solid (11 g, 94.0% yield).

$^1$H NMR (400 MHz, CDCl$_3$, δ): 9.905 (d, 1H); 8.928-8.923 (d, 1H); 8.720 (d, 1H); 8.503 (s, 2H); 8.383-8.352 (d, 2H); 8.192 (s, 1H); 8.123-8.103 (d, 2H); 7.977-7.941 (t, 4H); 7.869 (d, 1H); 7.790-7.759 (d, 2H); 7.684-7.380 (m, 14H).

Synthesis Example 13 (Synthesis of Compound 36-1)

Into the reaction flask, 4-biphenyl-4-yl-6-(3,5-dibromophenyl)-2-pyridin-3-yl-pyrimidine (10 g, 18.4 mmol), carbazole (7.1 g, 42.4 mmol) and STB (13.116 g, 13.6 mmol) were added, and 150 mL of toluene was added thereto and stirred. Pd(dba)$_2$ (0.673 g, 1.17 mmol) and P(t-butyl)$_3$ (0.662 g, 0.312 mmol) were added thereto. The mixture was stirred and refluxed at 115° C. for 18 hr. After the reaction was completed, 150 mL of ddH$_2$O was added thereto and the mixture was stirred until cooling to room temperature. The reactant was filtered and the solid residue was obtained and washed with ddH$_2$O and acetone. The mixed solution (200 mL of ddH$_2$O, 50 mL of methanol and 50 mL of acetone) was added to the solid residue, and the mixture was stirred for 30 min and filtered, repeated 2 times. The solid was oven-dried and redissolved in 1000 mL of toluene by heating and passed through a silica gel column. The eluent was concentrated by distillation, and then 300 mL of methanol was added thereto and stirred for 30 min. After the mixture was filtered and oven-dried, compound 36-1 was obtained as a yellowish solid (6.3 g, 48.0%/o yield).

$^1$H NMR (400 MHz, CDCl$_3$, δ): 9.898-9.894 (d, 1H); 8.940-8.910 (d, 1H); 8.752-8.736 (d, 1H); 8.640-8.635 (d, 2H); 8.380-8.354 (d, 2H); 8.219-8.200 (d, 4H); 8.163 (s, 1H); 8.038-8.028 (t, 1H); 7.799-7.768 (d, 2H); 7.682-7.631 (m, 6H); 7.519-7.345 (m, 12H).

Example 1 (Fabrication of Organic Electroluminescent Device)

The substrate was degreased and cleaned with solvents and UV ozone before it was loaded into the evaporation system. The substrate was then transferred into a vacuum deposition chamber for deposition of all layers on top of the substrate. By evaporation from a heated boat under a vacuum of approximately 10$^{-6}$ Torr, the following layers were deposited in the following sequence, as shown in FIG. 2:

a) a hole injection layer, 20 nm thick, HAT-CN;
   b) a hole transport layer, 60 nm thick, HT;
   c) an emitting layer, 30 nm thick, comprising BH doped with 3% BD by volume (BH and BD are product names from E-ray Optoelectronics Tech Co. Ltd, Taiwan);
   d) an electron transport layer, 25 nm thick, including compound 1-4 and doped quinolinolato-lithium (Liq);
   e) an electron injection layer, 1 nm thick, lithium fluoride (LiF); and
   f) a cathode: approximately 150 nm thick, including compound Al.

The device structure may be denoted as: ITO/HAT-CN (20 nm)/HT (60 nm)/BH-3% BD (30 nm)/compound 1-4 (25 nm):Liq (1 nm)/LiF (1 nm)/Al (150 nm).

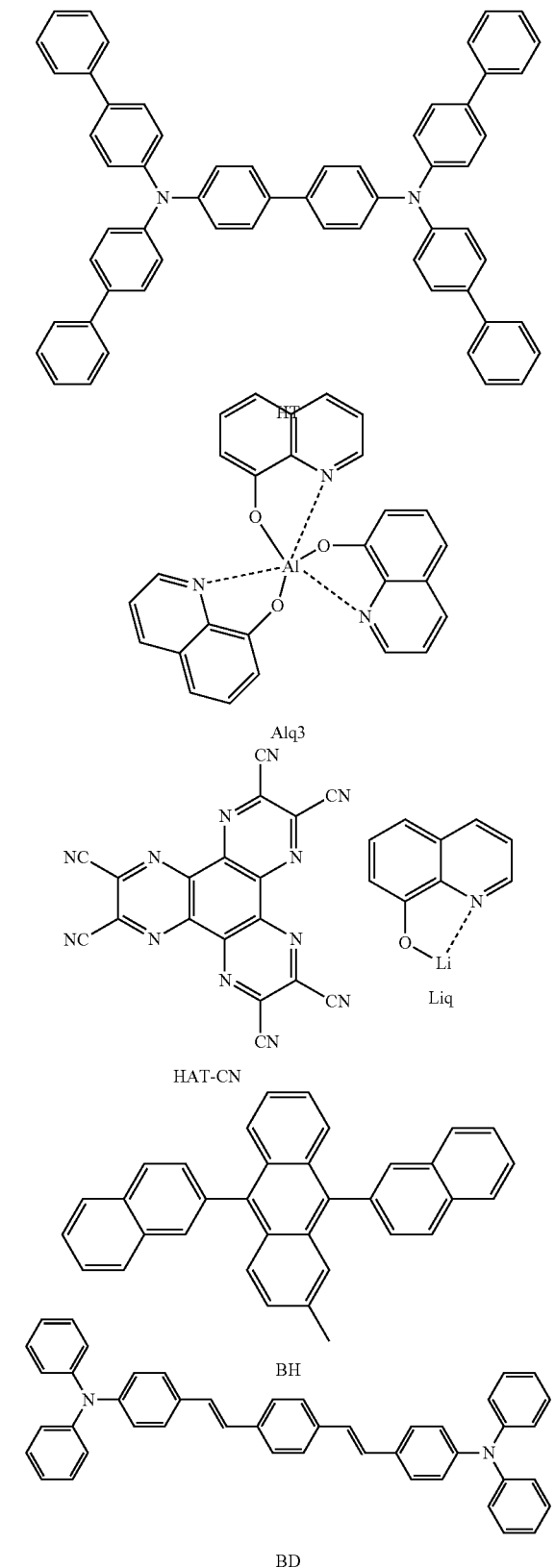

After the deposition of these layers, the device was transferred from the deposition chamber into a dry box for encapsulation, and were subsequently encapsulated using an UV-curable epoxy and a glass lid containing a moisture getter. The organic electroluminescent device has an emission area of 3 mm$^2$. The organic electroluminescent device was connected to an outside power source, and was operated under direct current voltage. The characteristics of the emission of light were confirmed and shown in Table 1 below.

The electroluminescent characteristics of all the fabricated organic electroluminescent devices were evaluated using a constant current source (KEITHLEY 2400 Source Meter, made by Keithley Instruments, Inc., Cleveland, Ohio) and a photometer (PHOTO RESEARCH SpectraScan PR 650, made by Photo Research, Inc., Chatsworth, Calif.) at room temperature.

Operational lifetime (or stability) of the devices were tested at room temperature and at various initial luminance depending on the color of the emitting layer by driving a constant current through the devices. The color was reported using Commission Internationale de l'Eclairage (CIE) coordinates.

Examples 2-6 (Fabrication of Organic Electroluminescent Device)

Except for replacing the compound 1-4 of the electron transport layer of Example 1 by compounds 1-6, 1-7, 12-6, 23-8 and 36-1, Example 2, Example 3, Example 4, Example 5, and Example 6 have the layer structure as shown in Example 1.

Comparative Example 1 (Fabrication of Organic Electroluminescent Device)

The organic electroluminescent device of Comparative Example was fabricated similar to the layer structure as Example 1, except for ET was used in place of compound 1-4 in the electron transport layer of Example 1. The device structure of Comparative Example 1 may be denoted as: ITO/HAT-CN (20 nm)/HT (60 nm)/BH-3% BD (30 nm)/ET: Liq (20 nm)/LiF (1 nm)/Al (150 nm).

Figure 4:
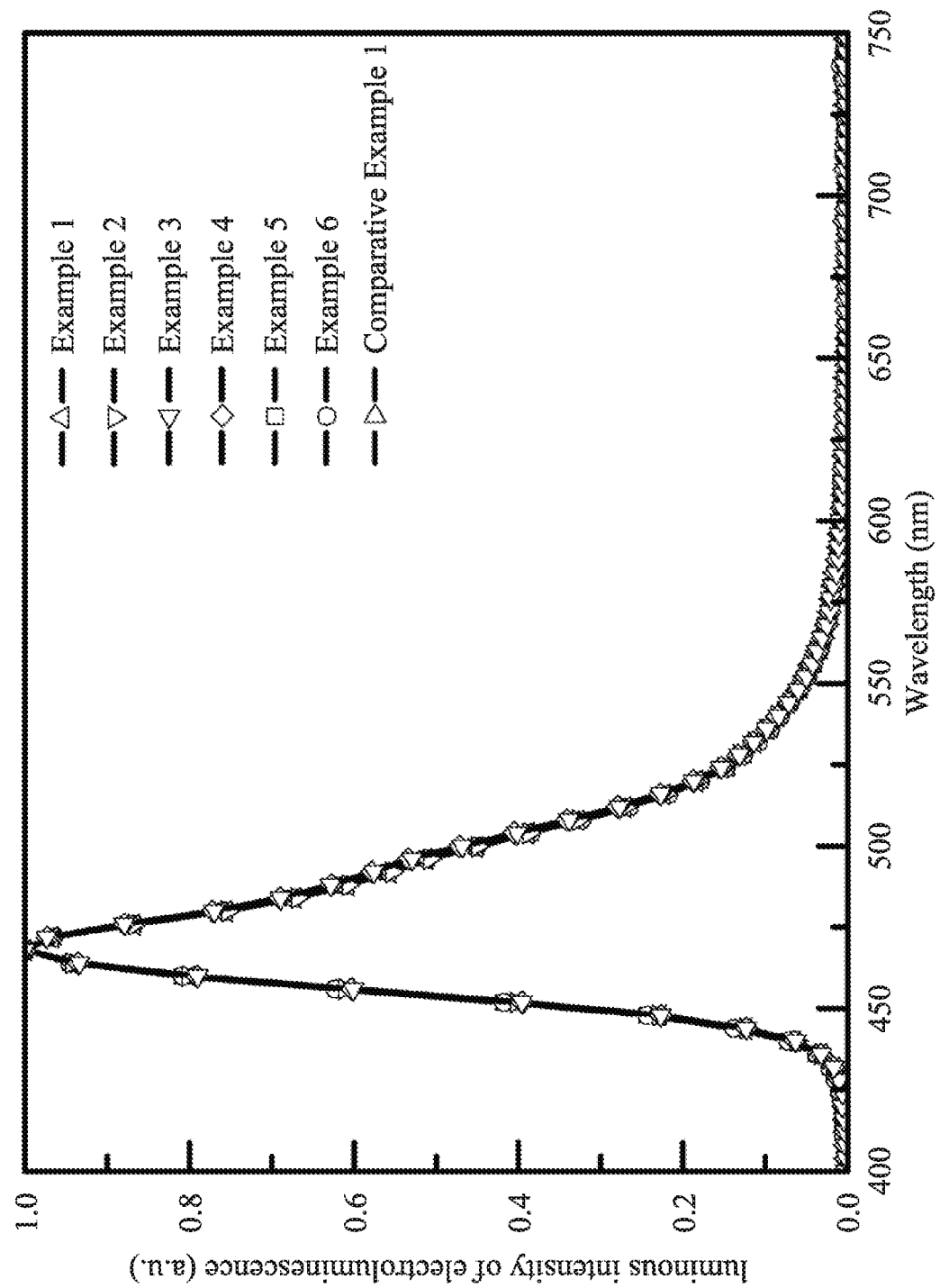
FIG. 4 shows the electroluminescent spectrum of an organic electroluminescent device according to the present disclosure.

The peak wavelength of the emitted light, maximum luminance efficiency, driving voltage, and stability of the organic electroluminescent devices fabricated in the examples are shown in Table 1. The electroluminescent spectra of the organic electroluminescent device are shown in FIG. 4.

The disclosure shall not be limited by the above described embodiment, method and examples, but by all embodiments and methods within the scope and spirit of the disclosure as claimed.

APPLICABILITY

As described above in detail, the organic electroluminescent device of the present disclosure comprising the material for the electroluminescent device can achieve the property of long lifetime and has high luminous efficiency and remains low driving voltage. Therefore, the organic electroluminescent device of the present disclosure is applicable to flat panel displays, mobile phone displays, light sources utilizing the characteristics of planar light emitters, signboards and has a high technical value.

The invention claimed is:
1. A compound represented by formula (I):

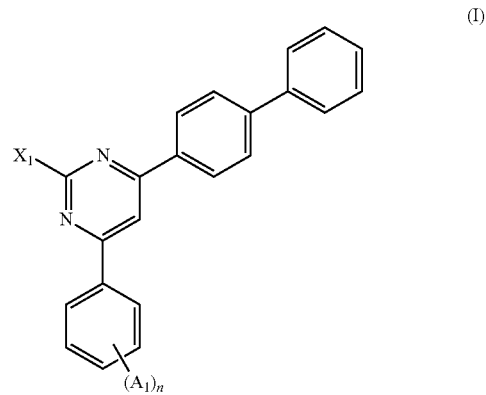

wherein
$X_1$ is selected from the group consisting of

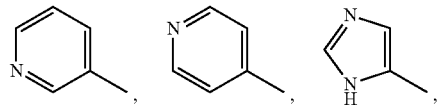

TABLE 1

| | compound (concentration %) | peak wavelength of the emitted light (nm) | driving voltage (V) | maximum luminance efficiency (cd/A) @ 10 mA/cm$^2$ | power efficiency (lm/W) | stability $T^{97}$ (hr) @$L_0$ = 1000 units |
|---|---|---|---|---|---|---|
| Example 1 | compound 1-4 (4) | 468 | 4.57 | 9.51 | 6.54 | 62.5 |
| Example 2 | compound 1-6 (4) | 468 | 4.78 | 9.68 | 6.36 | 62.0 |
| Example 3 | compound 1-7 (4) | 468 | 4.62 | 9.83 | 6.69 | 75.0 |
| Example 4 | compound 12-6 (4) | 468 | 4.74 | 10.26 | 6.80 | 50.0 |
| Example 5 | compound 23-8 (4) | 468 | 5.01 | 10.85 | 6.80 | 42.5 |
| Example 6 | compound 36-1 (4) | 468 | 5.39 | 8.38 | 4.89 | 75.0 |
| Comparative Example 1 | ET (4) | 468 | 4.75 | 9.85 | 6.52 | 24.6 |

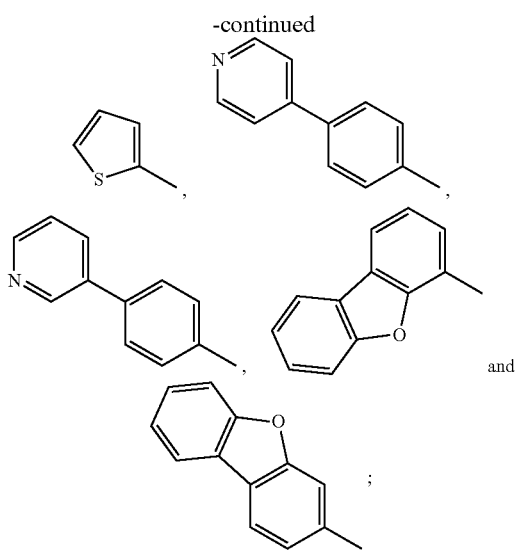

A¹ represent a substituted or unsubstituted (C6-C30) aryl, or a substituted or unsubstituted 5- to 30-membered heteroaryl; and n is an integer of 1 or 2.

2. The compound of claim 1, wherein $X_1$ and $A_1$ are the same.

3. The compound of claim 1, wherein $X_1$ and $A_1$ are different from each other.

4. The compound of claim 1, wherein when n is 2, each of $A_1$ is the same.

5. The compound of claim 1, wherein when n is 2, each of $A_1$ is different from each other.

6. The compound of claim 1, wherein $A_1$ is represented by a compound of formula (II) or (III):

formula (II)

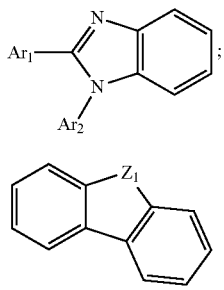

formula (III)

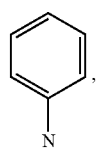

wherein
each of $Ar_1$ and $Ar_2$ independently represents unsubstituted (C6-C20) aryl(ene), and the compound of formula (II) binds to the compound of formula (I) or forms a fused ring with the compound of formula (I) by $Ar_1$ or $Ar_2$; and
$Z_1$ represents N,

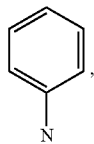

O, S, CMe₂ or CH₂, wherein when $Z_1$ is N, the compound of formula (III) binds to the compound of formula (I) by $Z_1$, and when $Z_1$ is

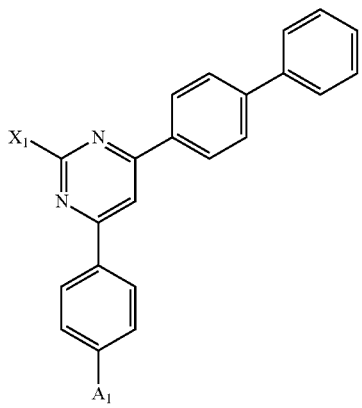

O, S, CMe₂ or CH₂, the compound of formula (III) binds to the compound of formula (I) by the phenyl group thereof.

7. The compound of claim 1, wherein when n is 1, the compound of formula (I) is represented by formula (I-1) or (I-2):

(I-1)

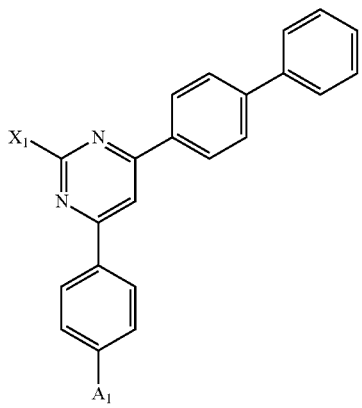

(I-2)

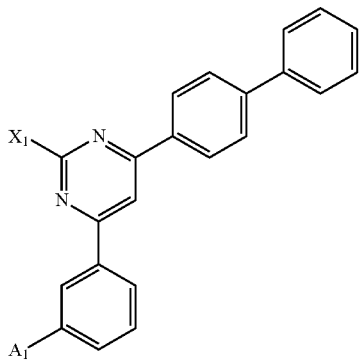

8. The compound of claim 1, wherein when n is 2, the compound of formula (I) is represented by formula (I-3):

(I-3)

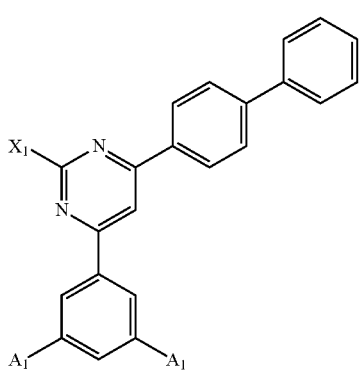

9. The compound of claim 1, wherein $A_1$ is selected from the group consisting of

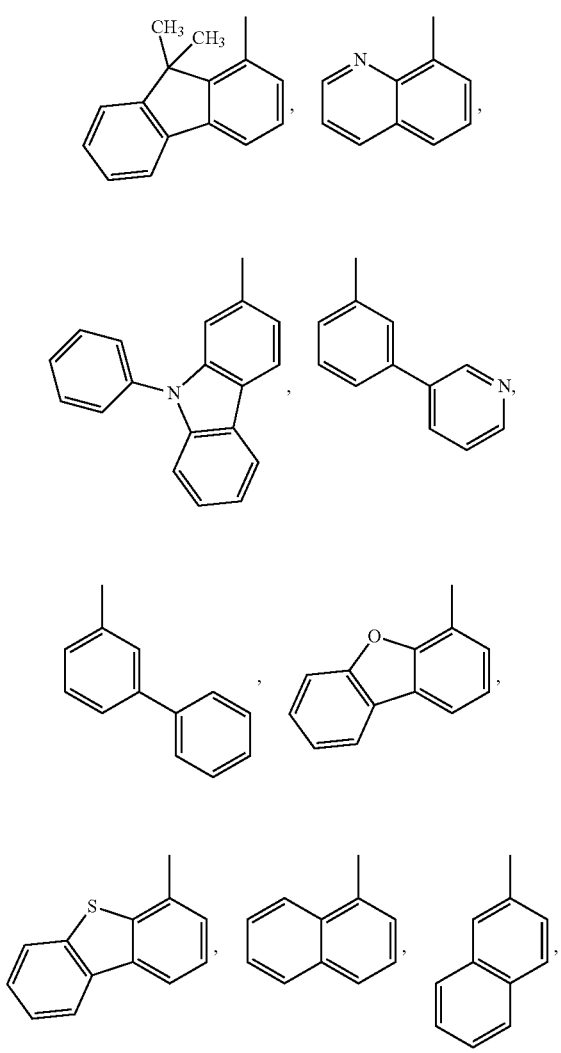

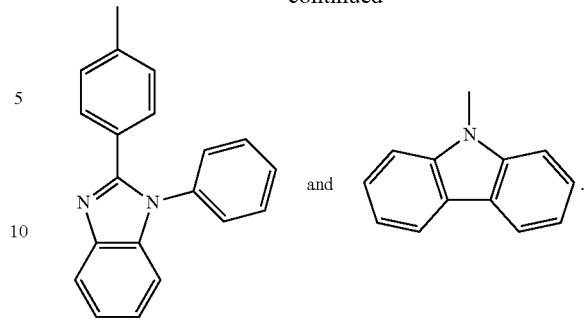

10. An organic electroluminescent device, comprising:
a cathode;
an anode; and
an organic layer disposed between the cathode and the anode, wherein the organic layer comprises the compound of formula (I) according to claim 1.

11. The organic electroluminescent device of claim 10, wherein based on a weight of the organic layer, an amount of the compound of formula (I) is from 25 wt % to 100 wt %.

12. The organic electroluminescent device of claim 10, wherein a thickness of the organic layer is from 1 nm to 500 nm.

13. The organic electroluminescent device of claim 10, wherein the organic layer is an electron transport layer comprising the compound of formula (I).

14. The organic electroluminescent device of claim 13, wherein the electron transport layer further comprises n-type electrically conducting dopants.

15. The organic electroluminescent device of claim 14, wherein an amount of the n-type electrically conducting dopants is from 0 wt % to 75 wt %.

16. The organic electroluminescent device of claim 10, wherein the organic layer is an electron transport layer, an electron injection layer, an emitting layer, a hole block layer or an electron block layer, and the emitting layer comprises fluorescent or phosphorescent emitters.

* * * * *